(12) United States Patent
Thom et al.

(10) Patent No.: US 6,903,085 B1
(45) Date of Patent: Jun. 7, 2005

(54) SUBSTITUTED PIPERIDINE COMPOUNDS USEFUL AS MODULATORS OF CHEMOKINE RECEPTOR ACTIVITY

(75) Inventors: Stephen Thom, Loughborough (GB); Andrew Baxter, Loughborough (GB); Nicholas Kindor, Loughborough (GB); Thomas McInally, Loughborough (GB); Brian Springthorpe, Loughborough (GB); Matthew Perry, Loughborough (GB); David Harden, Loughborough (GB); Richard Evans, Loughborough (GB); David Marriott, Loughborough (GB)

(73) Assignee: AstraZeneca, AB (CH)

( * ) Notice: Subject to any disclaimer, the term of this patent is extended or adjusted under 35 U.S.C. 154(b) by 0 days.

(21) Appl. No.: 10/069,215

(22) PCT Filed: Aug. 18, 2000

(86) PCT No.: PCT/GB00/03179

§ 371 (c)(1),
(2), (4) Date: Mar. 19, 2002

(87) PCT Pub. No.: WO01/14333

PCT Pub. Date: Mar. 1, 2001

(30) Foreign Application Priority Data

Aug. 24, 1999  (SE) ................................................ 9902987

(51) Int. Cl.[7] ...................... A61K 31/33; A61K 31/445; A61K 31/435; C07D 211/00; C07D 413/00
(52) U.S. Cl. ........................ 514/183; 514/277; 514/315; 514/318; 514/333; 514/336; 514/340; 514/364; 514/247; 514/383; 546/184; 546/193; 546/210; 546/223; 546/236; 546/269.1; 548/125; 548/131
(58) Field of Search ................................ 514/183, 247, 514/277, 315, 318, 333, 336, 340, 364, 383; 346/184, 193, 219, 223, 236, 269.1; 548/125, 131

(56) References Cited

U.S. PATENT DOCUMENTS

| | | | |
|---|---|---|---|
| 3,203,992 A | 8/1965 | Kunz et al. | 514/254.08 |
| 3,577,432 A | 5/1971 | Helsley et al. | 548/538 |
| 3,755,584 A | 8/1973 | Plotnikoff et al. | 514/292 |
| 3,818,017 A | 6/1974 | Janssen et al. | 546/199 |
| 3,894,030 A | 7/1975 | Janssen et al. | 546/199 |
| 4,029,801 A | 6/1977 | Cavalla et al. | 514/329 |
| 4,105,666 A | 8/1978 | Ward | 546/224 |
| 4,105,771 A | 8/1978 | Archibald et al. | 514/329 |
| 4,166,119 A | 8/1979 | Effland et al. | 514/278 |
| 4,246,267 A | 1/1981 | Vincent et al. | 514/329 |
| 4,264,613 A | 4/1981 | Regnier et al. | 514/322 |
| 4,338,323 A | 7/1982 | Regnier et al. | 514/318 |
| 5,576,321 A | 11/1996 | Krushinski, Jr. et al. | 514/254.09 |
| 5,614,523 A | 3/1997 | Audia et al. | 514/254.08 |
| 5,614,533 A | 3/1997 | Anderson et al. | 514/314 |
| 5,627,196 A | 5/1997 | Audia et al. | 514/323 |
| 5,688,960 A | 11/1997 | Shankar | 546/202 |
| 5,696,267 A | 12/1997 | Reichard et al. | 546/217 |
| 5,741,789 A | 4/1998 | Hibschman et al. | 514/212.02 |
| 5,789,402 A | 8/1998 | Audia et al. | 514/212.02 |
| 5,840,725 A | 11/1998 | Reichard et al. | 514/254.01 |

FOREIGN PATENT DOCUMENTS

| | | |
|---|---|---|
| DE | 37 23 568 A1 | 1/1989 |
| DE | 197 03 131 A1 | 7/1998 |
| DE | 197 55 268 A1 | 6/1999 |
| EP | 0 095 454 | 11/1983 |
| EP | 0 128 007 | 12/1984 |
| EP | 0 354 568 A2 | 2/1990 |
| EP | 0 407 217 A1 | 1/1991 |
| EP | 0 445 862 B1 | 9/1991 |
| EP | 0 457 686 B1 | 11/1991 |
| EP | 0 496 691 A1 | 7/1992 |
| EP | 0 587 311 A1 | 3/1994 |
| EP | 0 625 507 B1 | 11/1994 |
| EP | 0 643 057 A1 | 3/1995 |
| EP | 0 722 941 A2 | 7/1996 |
| EP | 0 903 349 A2 | 3/1999 |
| EP | 1013276 A1 | 6/2000 |
| FR | 2 190 430 | 2/1974 |
| GB | 1368012 | 9/1974 |
| GB | 1 404 868 | 9/1975 |
| GB | 1425354 | 2/1976 |
| GB | 1 532 671 | 11/1978 |
| GB | 1 538 542 | 1/1979 |
| GB | 1 544 191 | 4/1979 |

(Continued)

OTHER PUBLICATIONS

Chemical ASbstract DN 129:310895, also cited as Jp10259176.*
Chemical Abstract DN 120:30773, also cited as WO 9313083.*
Granata et al, PubMed Abstract 12876405, also cited as Int Arch Allergy Immunol., 131/3, 153–63(2003).*

(Continued)

*Primary Examiner*—Richard L. Raymond
*Assistant Examiner*—Sudhgaker B. Patel
(74) *Attorney, Agent, or Firm*—Fish & Richardson, P.C.

(57) ABSTRACT

The invention provides compounds of formula (I) wherein $R^1$, $R^2$, $R^3$, $R^6$, Z, Q, m, n, $X^1$, $X^2$, $X^3$, $X^4$ and T are as defined in the specification, processes for their preparation, pharmaceutical compositions containing them, and their use in therapy, especially for the treatment of chemokine receptor related diseases and conditions

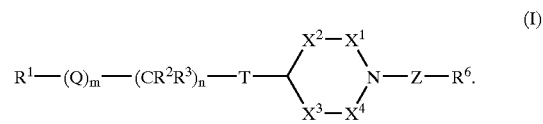

6 Claims, No Drawings

FOREIGN PATENT DOCUMENTS

| | | |
|---|---|---|
| JP | 63-264525 | 11/1988 |
| JP | 10259176 * | 6/1998 |
| JP | 10259176 * | 9/1998 |
| WO | WO 92/15579 | 9/1992 |
| WO | 9313083 * | 7/1993 |
| WO | WO 93/25528 | 12/1993 |
| WO | WO 94/27967 | 12/1994 |
| WO | WO 95/11880 | 5/1995 |
| WO | WO 96/26205 | 8/1996 |
| WO | WO 96/34857 | 11/1996 |
| WO | WO 96/39386 | 12/1996 |
| WO | WO 97/10207 | 3/1997 |
| WO | WO 97/19060 A1 | 5/1997 |
| WO | WO 97/23458 | 7/1997 |
| WO | WO 97/42956 | 11/1997 |
| WO | WO 97/47299 | 12/1997 |
| WO | WO 98/02151 A2 | 1/1998 |
| WO | WO 98/08826 | 3/1998 |
| WO | WO 98/31364 | 7/1998 |
| WO | WO 98/31366 | 7/1998 |
| WO | WO 98/32442 | 7/1998 |
| WO | WO 98/51311 | 11/1998 |
| WO | WO 99/04794 A1 | 2/1999 |
| WO | WO 99/04794 | 2/1999 |
| WO | WO 99/25686 | 5/1999 |
| WO | WO 99/27928 | 6/1999 |
| WO | WO 99/27929 | 6/1999 |
| WO | WO 99/28314 | 6/1999 |
| WO | WO 99/31092 | 6/1999 |
| WO | WO 99/37304 | 7/1999 |
| WO | WO 99/37619 A1 | 7/1999 |
| WO | WO 99/38514 | 8/1999 |
| WO | WO 99/64394 | 12/1999 |
| WO | WO 99/65895 | 12/1999 |
| WO | WO 00/08013 | 2/2000 |
| WO | WO 00/21948 | 4/2000 |
| WO | WO 00/21952 | 4/2000 |
| WO | WO 00/23076 | 4/2000 |
| WO | WO 00/35449 | 6/2000 |
| WO | WO 00/35451 | 6/2000 |
| WO | WO 00/39108 | 7/2000 |
| WO | WO 00/53600 | 9/2000 |
| WO | WO 00/58305 | 10/2000 |
| WO | WO 00/61559 | 10/2000 |
| WO | WO 00/69820 | 11/2000 |
| WO | WO 00/76513 A1 | 12/2000 |
| WO | WO 00/76973 A1 | 12/2000 |
| WO | WO 01/14333 A1 | 3/2001 |
| WO | WO 01/43744 | 6/2001 |
| WO | WO 01/44227 | 6/2001 |
| WO | WO 01/92227 A1 | 12/2001 |

OTHER PUBLICATIONS

Scott et al,PubMed Abstract 12783578, also cited as Expert Opin Ther. Targets, 7/3,427–40(2003).*

Craig Gerard, "Chemokine Receptors and Ligand Specificity: Understanding the Enigma" vol. 13, No. 72 (C–570), 21–31, Feb. 17, 1999.

Patent Abstracts of Japan, Medicine Composition Containing Piperazine Derivative and Having Active Oxygen Production Inhibiting And Active Oxygen Removing Action (Nov. 1, 1988).

Derwent Abstract 2000–587420/55, (2003), corresponding to Foreign Patent Document WO 00/53600, published Sep. 14, 2000 (Reference AT above).

Derwent Abstract 97–212513/19, (2003), corresponding to Foreign Patent Document WO 97/10207 A1, published Mar. 20, 1997 (Reference AQ Above).

Derwent Abstract 98–351249/49, (2003), corresponding to Foreign Patent Document JP 63–264525, published Nov. 1, 1988 (Reference AU above).

J. Hesselgesser et al., Journal of Biological Chemistry, vol. 273, No. 25, "Identification and Characterisation of Small Molecule Funtional Antagonisty of the CCR1 Chemokine Receptor" 15687–15692, (1998).

Howard P. Ng et al., Journal of Medicinal Chemistry, vol. 42, "Discovery of Novel Non–Peptide CCR1 Receptor Antagonists" 4680–4694, (1999).

Xavier Emodns–Alt et al., Bioorganic & Medicinal Chemistry Letters, vol. 3, No. 5, "Pharmacological Profile and Chemical Synthesis of SR 48968, a Non–Peptide Antagonist of the Neurokinin A ($NK_2$) Receptor" 925–930, (1993).

U.S. Appl. No. 10/276,430, Burrows et al., filed Dec. 10, 2002.

U.S. Appl. No. 10/468,179, Broush et al., filed Aug. 18, 2003.

U.S. Appl. No. 10/469,361, Burrows et al., filed Aug. 26, 2003.

U.S. Appl. No. 10/472,350, Burrows et al., filed Sep. 18, 2003.

U.S. Appl. No. 10/473,258, Burrows et al., filed Sep. 29, 2003.

U.S. Appl. No. 10/495,196, Tucker, filed May 11, 2004.

U.S. Appl. No. 10/495,410, Cummins et al., filed May 13, 2004.

U.S. Appl. No. 10/495,405, Cummins et al., May 12, 2004.

Archibald et al., "Antihypertensive Ureidopiperidines", J. Med. Chem. 23:857–861 (1980).

Archibald et al., "Antiinflammatory 4–acylaminopiperidines", CAPLUS 77:34355 (1972).

CAPLUS accession No. 1978:22640, document No. 88:22640, Yoshitomi Pharmaceutical Industries Ltd.: "Urea and thiourea derivatives" & JO A2, 52085174, 19700715.

CAPLUS, accession No. 1990:558675, document No. 113:158675, Yoshitomi Pharmaceutical Industries, Ltd.: Dihydroxycinnamic acid amide derivatives and their pharmaceutical compositions for enhancement of nerve growth factor (NGF) production & JP, A2, 02104568, 19900417.

Cattanach et al., "Studies in the Indole Series. Part IV, Tetrahydro–1H–pyrido [4,3–b]–indoles as Serotonin Antagonists", J. Chem. Soc. (C) 10:1235–1243 (1968).

Cohen et al., "Cytokine function: A study in biologic diversity", CAPLUS 125:31527 (1996).

Derwent Abstract 54050W/33 corresponding to Belgium Application BE 826994.

Derwent Abstract 93–339628/29 corresponding to PCT Application WO 00/23437 A1.

Derwent Abstract 96–136185/14 corresponding to Japanese Patent Application JP 08026999.

Derwent Abstract 96–136186/14 corresponding to Japanese Patent Application JP 08027000–A.

Derwent Abstract 96–136187/14 corresponding to Japanese Patent Application JP 08027001–A.

Derwent Abstract 99–040684/04 corresponding to Japanese Patent Application JP 10298180–A/2.

Friebe et al., "Piperidinopropyl dervatives and pharmaceutical compositions containing them ", CAPLUS 94:103172 (1981).

Hesselgesser et al., "Identification and Characterization of Small Molecule Functional Antagonists of the CCRI Chemokine Receptor", *J. Biol. Chem.* 273(25):15687–15692 (1998).

Howard et al., "Chemokines: progress toward identifying molecular targets for therapeutic agents", *Trends in Biotechnology* 14:46–51 (1996).

Janda, "A Soluble Polymer Approach to the "Fishing Out" Principle: Synthesis and Purification of β–Amino Alcohols", *J. Org. Chem.* 63:889–894 (1998).

Komai et al., "Structure–Activity Relationships of HIV–1 PR Inhibitors Containing AHPBA–II. Modification of Pyrrolidine Ring at P1'Proline", *Bioorganic & Medical Chemistry* 4(8):1365–1377 (1996).

Lawrence et al., "Automated Synthesis and Purification of Amides: Exploitation of Automated Solid Phase Extraction in Organic Synthesis", *Synthesis* 553–558, see table 1, (May 1997).

Leclerc et al., "Derivatives Related to Betaxolol with α–and β–Adrenergic Activities", *Arzneim.–Forsch/Drug. Res.* 35(11):1357–1367 (1985).

Mensonides–Harsema et al., "Synthesis and in Vitro and in Vivo Functional Studies of *Ortho*–Substituted Phenylpiperazine and N–Substituted 4–N–(o–Methoxyphenyl)aminopiperidine Analogues of W A Y 100635", *J. Med. Chem.* 43:432–439 (2000).

Meurer et al., "Discovery of potent human CCR5 antagonists for the treatment of HIV–1 infection—II.", *CAPLUS* 2000:331722 (2000).

Navas III et al., "The Design and Synthesis of a Haupten 1192U90, A Potential Atypical Antopsychotic Agent", *Syntheic Communications* 26(7):1411–1421 (1996).

Naya et al., "Design, Synthesis, and Discovery of a Novel CCR1 Antagonist", *J. Med. Chem.* 44:1429–1435 (2001).

Payard et al., "N–Aminomethylated Derivatives of Some Hydroxamic Acids as Anti–Inflammatories", *Eur. J. Med. Chem.* pp. 1–10 (1975).

Rubini et al., "Synthesis of Isosteric Methylene–Ony Pseudodipeptide Analogues as Novel Amide Bond Surrogate Units", *Tetrahedron* 42(21):6039–6045 (1986).

Srulevitch et al., "4–Phenylamidopiperidines: synthesis, pharmacological testing and SAR analysis", *Acta Pharm. Jugosl.* 41:89–106 (1991).

Srulevitch et al., "Design, Synthesis and SAR of Analgesics", QSAR: Quantitative Structure–Activity Relationships in Drug Design, pp. 377–381 (1989).

Stefano et al., "Human neutrophil and macrophage chemokinesis induced by cardiopulmonary bypass: Loss of DAME and IL–1 chemotaxis", *Journal of Neuroimmunology* 47:189–198 (1993).

Timmermans et al., "Hypotensive Properties of Benzodioxane Derivitaves Structurally Related to R 28935. Comparison of Activity with some Receptor Affinities", *Arch. int. Pharmacodyn.* 255:321–334 (1982).

Wade et al., "Application of Base Cleavable Safety Catch Linkers to Solid Phase Library Production", *J. Comb. Chem.* 2:266–275, see page 269 scheme 3 and table 4, compounds 32 a–m (2000).

Wright et al., "Discovery of Selective Dopamine D4 Receptor Antagonists: 1–Aryloxy–3–(4–Aryloxypiperidinyl)–2–Propanols", *Bioorganic & Medicinal Chemistry Letters* 7(11):1377–1380 (1997).

* cited by examiner

SUBSTITUTED PIPERIDINE COMPOUNDS USEFUL AS MODULATORS OF CHEMOKINE RECEPTOR ACTIVITY

This application is a 371 of PCT/GB00/3179 filed Aug. 18, 2000, which claims benefit of Sweden 9902987-8 filed Aug. 24, 1999.

The present invention relates to substituted piperidine compounds, processes for their preparations, pharmaceutical compositions containing them and their use in therapy.

Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8–14 kDa proteins characterised by a conserved four cysteine motif. The chemokine superfamily can be divided into two main groups exhibiting characteristic structural motifs, the Cys-X-Cys (C-X-C) and Cys—Cys (C—C) families. These are distinguished on the basis of a single amino acid insertion between the NH-proximal pair of cysteine residues and sequence similarity.

The C-X-C chemokines include several potent chemoattractants and activators of neutrophils such as interleukin-8 (IL-8) and neutrophil-activating peptide 2 (NAP-2).

The C—C chemokines include potent chemoattractants of monocytes and lymphocytes but not neutrophils such as human monocyte chemotactic proteins 1–3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

The present invention provides a compound of formula (I):

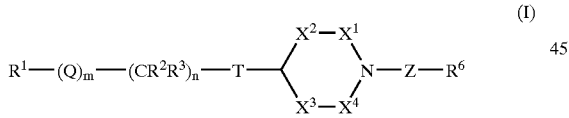

wherein

Z is $CR^4R^5$, $C(O)$ or $CR^4R^5-Z^1$;

$Z^1$ is $C_{1-4}$ alkylene (such as $CH_2$), $C_{2-4}$ alkenylene (such as CH=CH) or C(O)NH;

$R^1$ represents a $C_1$–$C_{12}$ alkyl group optionally substituted by one or more substituents independently selected from cyano, hydroxyl, $C_1$–$C_4$ alkoxy (such as methoxy or ethoxy), $C_1$–$C_6$ alkylthio (such as methylthio), $C_{3-7}$ cycloalkyl (such as cyclopropyl), $C_1$–$C_6$ alkoxycarbonyl (such as methoxycarbonyl) and phenyl (itself optionally substituted by one or more of halogen, nitro, cyano, $C_1$–$C_6$ alkyl, $C_1$–$C_6$ haloalkyl (such as $CF_3$), phenyl($C_1$–$C_6$ alkyl) (such as benzyl), $C_1$–$C_6$ alkoxy, $C_1$–$C_6$ haloalkoxy, $S(O)_2(C_1$–$C_6$ alkyl), $C(O)NH_2$, carboxy or $C_1$–$C_6$ alkoxycarbonyl); or $R^1$ represents $C_2$–$C_6$ alkenyl optionally substituted by phenyl (itself optionally substituted by one or more of halogen, nitro, cyano, $C_1$–$C_6$ alkyl, $C_1$–$C_6$ haloalkyl, phenyl($C_1$–$C_6$ alkyl), $C_1$–$C_6$ alkoxy, $C_1$–$C_6$ haloalkoxy, $S(O)_2(C_1$–$C_6$ alkyl), $C(O)NH_2$, carboxy or $C_1$–$C_6$ alkoxycarbonyl); or $R^1$ represents a 3- to 14-membered saturated or unsaturated ring system which optionally comprises up to two ring carbon atoms that form carbonyl groups and which optionally further comprises up to 4 ring heteroatoms independently selected from nitrogen, oxygen and sulphur, wherein the ring system is optionally substituted by one or more substituents independently selected from: halogen, cyano, nitro, oxo, hydroxyl, $C_1$–$C_8$ alkyl, $C_1$–$C_6$ hydroxyalkyl, $C_1$–$C_6$ haloalkyl, $C_{1-6}$ alkoxy($C_1$–$C_6$ alkyl), $C_3$–$C_7$ cycloalkyl($C_1$–$C_6$ alkyl), $C_1$–$C_6$ alkylthio($C_1$–$C_6$ alkyl), $C_1$–$C_6$ alkylcarbonyloxy($C_1$–$C_6$ alkyl), $C_1$–$C_6$ alkylS(O)$_2$($C_1$–$C_6$ alkyl), aryl($C_1$–$C_6$ alkyl), heterocyclyl($C_1$–$C_6$ alkyl), arylS(O)$_2$($C_1$–$C_6$ alkyl), heterocyclylS(O)$_2$($C_1$–$C_6$ alkyl), aryl($C_1$–$C_6$ alkyl)S(O)$_2$, heterocyclyl($C_1$–$C_6$ alkyl)S(O)$_2$, $C_2$–$C_6$ alkenyl, $C_1$–$C_6$ alkoxy, carboxy-substituted $C_1$–$C_6$ alkoxy, $C_1$–$C_4$ haloalkoxy, $C_1$–$C_6$ hydroxyalkoxy, $C_1$–$C_6$ alkylcarboxy-substituted $C_1$–$C_6$ alkoxy, aryloxy, heterocyclyloxy, $C_1$–$C_6$ alkylthio, $C_3$–$C_7$ cycloalkyl($C_1$–$C_6$ alkylthio), $C_3$–$C_6$ alkynylthio, $C_1$–$C_6$ alkylcarbonylamino, $C_1$–$C_6$ haloalkylcarbonylamino, SO$_3$H, —NR$^7$R$^8$, —C(O)NR$^{23}$R$^{24}$, S(O)$_2$NR$^{18}$R$^{19}$, S(O)$_2$R$^{20}$, R$^{25}$C(O), carboxyl, $C_1$–$C_6$ alkoxycarbonyl, aryl and heterocyclyl;

wherein the foregoing aryl and heterocyclyl moieties are optionally substituted by one or more of halogen, oxo, hydroxy, nitro, cyano, $C_1$–$C_6$ alkyl, $C_1$–$C_6$ haloalkyl, phenyl($C_1$–$C_6$ alkyl), $C_1$–$C_6$ alkoxy, $C_1$–$C_6$ haloalkoxy, $S(O)_2(C_1$–$C_6$ alkyl), $C(O)NH_2$, carboxy or $C_1$–$C_6$ alkoxycarbonyl;

m is 0 or 1;

Q represents an oxygen or sulphur atom or a group $NR^9$, $C(O)$, $C(O)NR^9$, $NR^9C(O)$ or CH=CH;

n is 0, 1, 2, 3, 4, 5 or 6 provided that when n is 0, then m is 0;

each $R^2$ and $R^3$ independently represents a hydrogen atom or a $C_1$–$C_4$ alkyl group, or $(CR^2R^3)_n$ represents $C_3$–$C_7$ cycloalkyl optionally substituted by $C_1$–$C_4$ alkyl;

T represents a group $NR^{10}$, $C(O)NR^{10}$, $NR^{11}C(O)NR^{10}$ or $C(O)NR^{10}NR^{11}$;

$X^1$, $X^2$, $X^3$ and $X^4$ are, independently, $CH_2$, $CHR^{12}$ {wherein each $R^{12}$ is, independently, $C_1$–$C_4$ alkyl or $C_3$–$C_7$ cycloalkyl($C_1$–$C_4$ alkyl)} or C=O; or, when they are $CHR^{12}$, the $R^{12}$ groups of $X^1$ and $X^3$ or $X^4$, or, $X^2$ and $X^3$ or $X^4$ join to form a two or three atom chain which is $CH_2CH_2$, $CH_2CH_2CH_2$, $CH_2OCH_2$ or $CH_2SCH_2$; provided always that at least two of $X^1$, $X^2$, $X^3$ and $X^4$ are $CH_2$;

$R^4$ and $R^5$ each independently represent a hydrogen atom or a $C_1$–$C_4$ alkyl group;

$R^6$ is aryl or heterocyclyl, both optionally substituted by one or more of: halogen, cyano, nitro, oxo, hydroxyl, $C_1$–$C_8$ alkyl, $C_1$–$C_6$ hydroxyalkyl, $C_1$–$C_6$ haloalkyl, $C_{1-6}$ alkoxy($C_1$–$C_6$ alkyl), $C_3$–$C_7$ cycloalkyl($C_1$–$C_6$ alkyl), $C_1$–$C_6$ alkylthio($C_1$–$C_6$ alkyl), $C_1$–$C_6$ alkylcarbonyloxy($C_1$–$C_6$ alkyl), $C_1$–$C_6$ alkylS(O)$_2$($C_1$–$C_6$ alkyl), aryl($C_1$–$C_6$ alkyl), heterocyclyl($C_1$–$C_6$ alkyl), arylS(O)$_2$($C_1$–$C_6$ alkyl), heterocyclylS(O)$_2$($C_1$–$C_6$ alkyl), aryl($C_1$–$C_6$ alkyl)S(O)$_2$, heterocyclyl($C_1$–$C_6$ alkyl)S(O)$_2$, $C_2$–$C_6$ alkenyl, $C_1$–$C_6$ alkoxy, carboxy-substituted $C_1$–$C_6$ alkoxy, $C_1$–$C_6$ haloalkoxy, $C_1$–$C_6$ hydroxyalkoxy, $C_1$–$C_6$ alkylcarboxy-substituted $C_1$–$C_6$ alkoxy, aryloxy, heterocyclyloxy, $C_1$–$C_6$ alkylthio, $C_3$–$C_7$ cycloalkyl($C_1$–$C_6$ alkylthio), $C_3$–$C_6$ alkynylthio, $C_1$–$C_6$ alkylcarbonylamino, $C_1$–$C_6$ haloalkylcarbonylamino, $SO_3H$, —$NR^{16}R^{17}$, —$C(O)NR^{21}R^{22}$, $S(O)_2NR^{13}R^{14}$, $S(O)_2R^{15}$, $R^{26}C(O)$, carboxyl, $C_1$–$C_6$ alkoxycarbonyl, aryl and heterocyclyl; wherein the foregoing aryl and heterocyclyl moieties are optionally substituted by one or more of halogen, nitro, cyano, $C_1$–$C_6$ alkyl, $C_1$–$C_6$ haloalkyl, phenyl($C_1$–$C_6$ alkyl), $C_1$–$C_6$ alkoxy, $C_1$–$C_6$ haloalkoxy, $S(O)_2(C_1$–$C_6$ alkyl), $C(O)NH_2$, carboxy or $C_1$–$C_6$ alkoxycarbonyl;

$R^7$, $R^8$, $R^9$, $R^{10}$, $R^{11}$, $R^{13}$, $R^{14}$, $R^{16}$, $R^{17}$, $R^{18}$, $R^{19}$, $R^{21}$, $R^{22}$, $R^{23}$ and $R^{24}$ are, independently, hydrogen, $C_1$–$C_6$ alkyl, $C_1$–$C_6$ haloalkyl, $C_1$–$C_6$ hydroxyalkyl, $C_3$–$C_7$ cycloalkyl, $C_3$–$C_7$ cycloalkyl($C_1$–$C_4$ alkyl) or phenyl ($C_1$–$C_6$ alkyl); and, $R^{15}$ and $R^{20}$ are, independently, $C_1$–$C_6$ alkyl, $C_1$–$C_6$ hydroxyalkyl, $C_3$–$C_6$ cycloalkyl, $C_3$–$C_7$ cycloalkyl ($C_1$–$C_4$ alkyl) or $C_1$–$C_6$ alkyl optionally substituted by phenyl;

$R^{25}$ and $R^{26}$ are, independently, $C_1$–$C_6$ alkyl or phenyl (optionally substituted by one or more of halogen, nitro, cyano, $C_1$–$C_6$ alkyl, $C_1$–$C_6$ haloalkyl, phenyl ($C_1$–$C_6$ alkyl), $C_1$–$C_6$ alkoxy, $C_1$–$C_6$ haloalkoxy, $S(O)_2(C_1$–$C_6$ alkyl), $C(O)NH_2$, carboxy or $C_1$–$C_6$ alkoxycarbonyl);

or a pharmaceutically acceptable salt thereof, or solvate thereof, or a solvate of a salt thereof;

provided that when T is $C(O)NR^{10}$ and $R^1$ is optionally substituted phenyl then n is not 0.

Certain compounds of formula (I) are capable of existing in isomeric forms (for example as tautomers, enantiomers, geometric isomers or diastereomers). The present invention encompasses all such isomers and mixtures thereof in all proportions.

Hydroxyalkyl is, for example, 2-hydroxyeth-1-yl. Haloalkyl is, for example, $CF_3$. Alkoxy is, for example, methoxy or ethoxy. Alkoxy($C_1$–$C_6$ alkyl) is, for example, methoxymethyl or ethoxyethyl. Cycloalkyl is, for example, cyclopropyl or cyclohexyl. Cycloalkyl($C_1$–$C_6$ alkyl) is, for example, cyclopropylmethyl. Alkylthio is, for example, methylthio or ethylthio. Alkylthio($C_1$–$C_6$ alkyl) is, for example, methylthiomethyl. Alkylcarbonyloxy($C_1$–$C_6$ alkyl) is, for example, $CH_3C(O)OCH_2$. $S(O)_2$(alkyl) is, for example, $CH_3S(O)_2$. AlkylS$(O)_2(C_1$–$C_6$ alkyl) is, for example, $CH_3S(O)_2CH_2$. Aryl($C_1$–$C_6$ alkyl) is, for example, benzyl, 2-phenyleth-1-yl or 1-phenyleth-1-yl. Heterocyclyl ($C_1$–$C_6$ alkyl) is, for example, heterocyclylmethyl. ArylS $(O)_2$ ($C_1$–$C_6$ alkyl) is, for example, phenylS$(O)_2CH_2$. HeterocyclylS$(O)_2(C_1$–$C_6$ alkyl) is, for example, heterocyclylS$(O)_2CH_2$. Aryl($C_1$–$C_6$ alkyl)S$(O)_2$ is, for example, benzylS$(O)_2$. Heterocyclyl($C_1$–$C_6$ alkyl)S$(O)_2$ is, for example, heterocyclylCH$_2$S$(O)_2$. Alkenyl is, for example, vinyl or allyl. Carboxy-substituted $C_1$–$C_6$ alkoxy is, for example, HOC(O)CH$_2$CH$_2$O. Haloalkoxy is, for example, $OCF_3$. Hydroxyalkoxy is, for example, HOCH$_2$CH$_2$O. Alkylcarboxy-substituted $C_1$–$C_6$ alkoxy is, for example, $CH_3OC(O)CH_2CH_2O$. Aryloxy is, for example, phenoxy.

Heterocyclyloxy is, for example, pyridinyloxy or pyrimidinyloxy. $C_3$–$C_7$ cycloalkyl($C_1$–$C_6$ alkylthio) is, for example, cyclopropylCH$_2$S. Alkynylthio is, for example, propargylthio. Alkylcarbonylamino is, for example, acylamino. Haloalkylcarbonylamino is, for example, ClCH$_2$C(O)NH. Alkoxycarbonyl is, for example, $CH_3OC(O)$.

Aryl is a carbocyclic aromatic ring optionally fused to one or more carbocyclic rings. Aryl is, for example, phenyl, naphthyl or indanyl.

Heterocyclyl is an aromatic or non-aromatic ring system preferably comprising up to 6 (preferably up to 4) heteroatoms selected from the group comprising nitrogen, oxygen and sulphur, and preferably comprising one, two or three 5- or 6-membered rings. Heterocyclyl is, for example, furyl, thienyl, pyrrolyl, 2,5-dihydropyrrolyl, thiazolyl, pyrazolyl, oxazolyl, isoxazolyl, imidazolyl, 1,2,4-oxadiazolyl, 1,3,4-oxadiazolyl, 1,2,3-triazolyl, 1,2,4-triazolyl, tetrazolyl, pyrrolidinyl, piperidinyl, piperazinyl, morpholinyl, pyridinyl (for example 2-pyridinyl, 3-pyridinyl or 4-pyridinyl), pyrimidinyl (for example 2-pyrimidinyl or 4-pyrimidinyl), pyrazinyl, pyridazinyl, indolyl, 2,3-dihydroindolyl, benzo [b]furyl, benz[b]thienyl, 2,3-dihydrobenz[b]thienyl (for example 1-dioxo-2,3-dihydrobenz[b]thienyl), benzimidazolyl, benztriazolyl, benzoxazolyl, benzthiazolyl, 2,3-dihydrobenzthiazolyl (for example 2,3-dihydrobenzthiazol-2-onyl which is also known as 2-oxo-1,3-benzothiazol-3(2H)-yl), 1,2,3-benzothiadiazolyl, 1,2,3-benzoxadiazolyl, 2,1,3-benzothiadiazolyl, 2,1,3-benzoxadiazolyl, quinoxalinyl, dihydro-1-benzopyryliumyl (for example a coumarinyl or a chromenonyl), 1,3-benzodioxolyl (also known as 1,2-methylenedioxyphenyl), 3,4-dihydro-1H-2,1-benzothiazinyl (for example 2-dioxo-3,4-dihydro-1H-2,1-benzothiazinyl), purine (for example 1H-purine or 9H-purine), 1H-pyrazolo[3,4-d]pyrimidinyl, thieno[2,3-d]pyrimidinyl, thieno[3,2-d]pyrimidinyl, quinolinyl (for example 2-quinolinyl, 3-quinolinyl or 4-quinolinyl), isoquinolinyl, quinazolinyl or dibenzothiophenyl; or a ring as shown below:

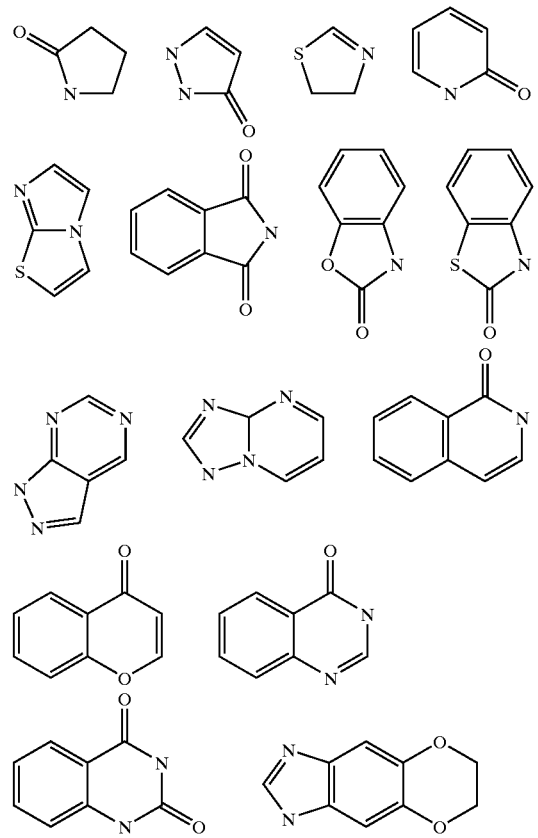

The group $R^1$ may represent an optionally substituted 3- to 14-membered (especially 5- to 10-membered) saturated or unsaturated ring system which optionally comprises one or two ring carbon atoms that form carbonyl groups and which optionally further comprises one, two, three or four ring heteroatoms independently selected from nitrogen, oxygen and sulphur. Examples of $R^1$ ring systems, which can be monocyclic or polycyclic, include cyclopropyl, cyclobutyl, cyclopentyl, cyclohexyl, phenyl, naphthyl, indanyl, furyl, thienyl, pyrrolyl, 2,5-dihydropyrrolyl, thiazolyl, pyrazolyl, oxazolyl, isoxazolyl, imidazolyl, 1,2,4-oxadiazolyl, 1,3,4-oxadiazolyl, 1,2,3-triazolyl, 1,2,4-triazolyl, tetrazolyl, pyrrolidinyl, piperidinyl, piperazinyl, morpholinyl, pyridinyl (for example 2-pyridinyl, 3-pyridinyl or 4-pyridinyl), pyrimidinyl (for example 2-pyrimidinyl or 4-pyrimidinyl), pyrazinyl, pyridazinyl, indolyl, 2,3-dihydroindolyl, benzo[b]furyl, benz[b]thienyl, 2,3-dihydrobenz[b]thienyl (for example 1-dioxo-2,3-dihydrobenz[b]thienyl), benzimidazolyl, benztriazolyl, benzoxazolyl, benzthiazolyl, 2,3-dihydrobenzthiazolyl (for example 2,3-dihydrobenzthiazol-2-onyl which is also known as 2-oxo-1,3-benzothiazol-3(2H)-yl), 1,2,3-benzothiadiazolyl, 1,2,3-benzoxadiazolyl, 2,1,3-benzothiadiazolyl, 2,1,3-benzoxadiazolyl, quinoxalinyl, dihydro-1-benzopyryliumyl (for example a coumarinyl or a chromenonyl), 1,3-benzodioxolyl (also known as 1,2-methylenedioxyphenyl), 3,4-dihydro-1H-2,1-benzothiazinyl (for example 2-dioxo-3,4-dihydro-1H-2,1-benzothiazinyl), purine (for example 1H-purine or 9H-purine), 1H-pyrazolo[3,4-d]pyrimidinyl, thieno[2,3-d]pyrimidinyl, thieno[3,2-d]pyrimidinyl, quinolinyl (for example 2-quinolinyl, 3-quinolinyl or 4-quinolinyl), isoquinolinyl, quinazolinyl or dibenzothiophenyl; or a ring as shown below:

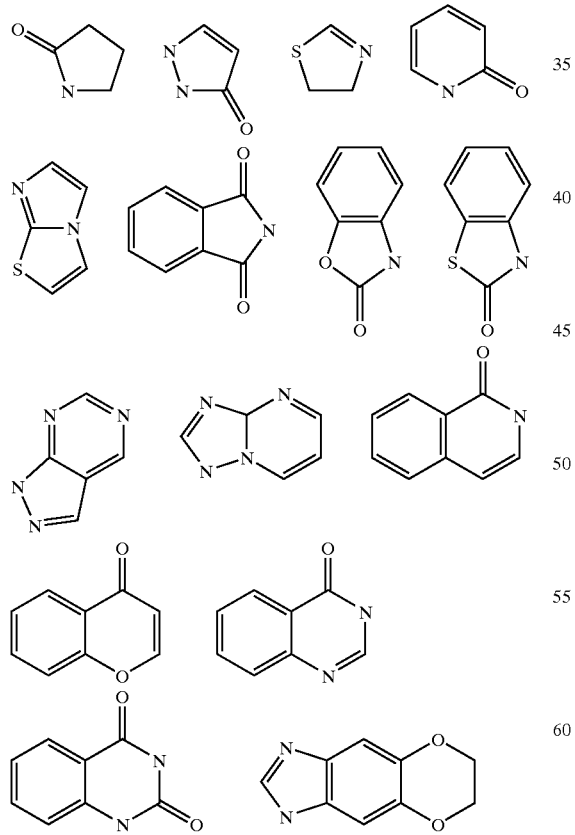

In one aspect the present invention provides a compound of formula (Ia):

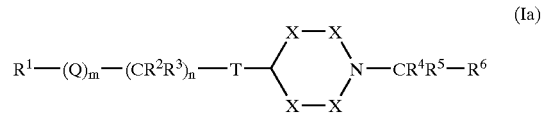

wherein $R^1$ represents a $C_1$–$C_{12}$ alkyl group optionally substituted by one or more substituents independently selected from cyano, hydroxyl, $C_1$–$C_6$ alkoxy, $C_1$–$C_6$ alkylthio and $C_1$–$C_6$ alkoxycarbonyl, or $R^1$ represents a 3- to 10-membered saturated or unsaturated ring system which optionally comprises up to two ring carbon atoms that form carbonyl groups and which optionally further comprises up to 4 ring heteroatoms independently selected from nitrogen, oxygen and sulphur, wherein the ring system is optionally substituted by one or more substituents independently selected from halogen, cyano, nitro, hydroxyl, carboxyl, $C_1$–$C_6$ alkyl, $C_1$–$C_6$ hydroxyalkyl, $C_1$–$C_6$ haloalkyl, $C_1$C$_6$ alkoxy, carboxy-substituted $C_1$–$C_6$ alkoxy, $C_1$–$C_6$ alkylthio, $C_1$–$C_6$ alkylthiomethyl, $C_1$–$C_6$ alkylcarbonylamino, —$NR^7R^8$, —$C(O)NR^7R^8$, $C_1$–$C_6$ alkylcarbonyloxymethyl, $C_1$–$C_6$ alkoxycarbonyl, $C_1$–$C_6$ alkoxycarbonylpiperazinyl, furyl, phenyl, pyridinyl, pyrazinyl, halophenyl, thienyl, thienylmethyl, $C_1$–$C_6$ alkylbenzyl and

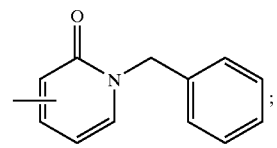

m is 0 or 1;

Q represents an oxygen or sulphur atom or a group $NR^9$, $C(O)$, $C(O)NR^9$ or $NR^9C(O)$;

n is 0, 1, 2, 3 or 4, provided that when n is 0, then m is 0;

each $R^2$ and $R^3$ independently represents a hydrogen atom or a $C_1$–$C_4$ alkyl group;

T represents a group $NR^{10}$, $C(O)NR^{10}$ or $NR^{11}C(O)NR^{10}$;

each X independently represents a group $CH_2$, $CHR^{12}$ or C=O, provided that at least two groups X simultaneously represent $CH_2$;

$R^4$ and $R^5$ each independently represent a hydrogen atom or a $C_1$–$C_4$ alkyl group;

$R^6$ represents a phenyl group optionally substituted by one or more substituents independently selected from halogen, amino (—$NH_2$), nitro, cyano, sulphonyl (—$SO_3H$), sulphonamido (—$SO_2NH_2$), $C_1$–$C_6$ alkyl, $C_1$–$C_6$ haloalkoxy and $C_1$–$C_6$ alkylsulphonyl;

$R^7$ and $R^8$ each independently represent a hydrogen atom or a group selected from $C_1$–$C_6$ hydroxyalkyl, $C_3$–$C_6$ cycloalkyl and $C_1$–$C_6$ alkyl optionally substituted by phenyl; $R^9$, $R^{10}$ and $R^{11}$ each independently represent a hydrogen atom, or a $C_1$–$C_4$ alkyl or cyclopropylmethyl group; and each $R^{12}$ independently represents a $C_1$–$C_4$ alkyl or cyclopropylmethyl group;

or a pharmaceutically acceptable salt or solvate thereof.

In the context of the present specification, unless otherwise indicated an alkyl substituent or an alkyl moiety in a substituent group may be linear or branched. Examples of alkyl groups/moieties containing up to twelve carbon atoms include methyl, ethyl, n-propyl, iso-propyl, n-butyl, iso-butyl, tert-butyl, n-pentyl, n-hexyl, n-heptyl, n-octyl, n-nonyl, n-decyl, n-undecyl and n-dodecyl groups. A $C_1$–$C_6$ hydroxyalkyl group will comprise at least one hydroxyl group (e.g. one, two or three hydroxyl groups) which may be attached to an internal or terminal carbon atom of the alkyl chain. Similarly, a carboxy-substituted $C_1$–$C_6$ alkoxy group will comprise at least one carboxyl group (e.g. one, two or three carboxyl groups) which may be attached to an internal or terminal carbon atom of the alkyl chain. A $C_1$–$C_6$ haloalkyl or $C_1$–$C_6$ haloalkoxy group will comprise at least one halogen atom (e.g. one, two, three or four halogen atoms independently selected from fluorine, chlorine, bromine and iodine) which may be attached to an internal or terminal carbon atom of the alkyl chain. A halophenyl group will comprise from 1 to 5 halogen atoms independently selected from fluorine, chlorine, bromine and iodine. A $C_1$–$C_6$ alkylbenzyl group will comprise at least one $C_1$–$C_6$ alkyl group (e.g. one, two or three $C_1$–$C_6$ alkyl groups) attached to the phenyl ring of the benzyl moiety. If there is more than one $C_1$–$C_6$ alkyl group attached to the phenyl ring, the groups may be the same or different. In a $C_1$–$C_6$ alkoxycarbonylpiperazinyl substituent group, the piperazinyl moiety is attached through a nitrogen atom to the carbonyl moiety. When T represents $C(O)NR^9$, it should be understood that the nitrogen atom is attached directly to the six-membered heterocyclic ring in formula (I).

The group $R^1$ may represent a $C_1$–$C_{12}$, preferably $C_1$–$C_{10}$, more preferably $C_1$–$C_6$, alkyl group optionally substituted by one or more (e.g. one, two, three or four) substituents independently selected from cyano, hydroxyl, $C_1$–$C_6$, preferably $C_1$–$C_4$, alkoxy, $C_1$–$C_6$, preferably $C_1$–$C_4$, alkylthio and $C_1$–$C_6$ alkoxycarbonyl, preferably $C_1$–$C_4$ alkoxycarbonyl.

The group $R^1$ may alternatively represent an optionally substituted 3- to 10-membered saturated or unsaturated ring system which optionally comprises one or two ring carbon atoms that form carbonyl groups and which optionally further comprises one, two, three or four ring heteroatoms independently selected from nitrogen, oxygen and sulphur. Examples of ring systems that may be used which can be monocyclic or polycyclic include cyclopropyl, cyclobutyl, cyclopentyl, cyclohexyl, phenyl, pyrazolyl, furyl, thienyl, imidazolyl, quinolinyl (e.g. 2-quinolinyl, 3-quinolinyl or 4-quinolinyl), pyridinyl (e.g. 2-pyridinyl, 3-pyridinyl or 4-pyridinyl), 1,3-benzodioxolyl, thiazolyl, benzimidazolyl, oxadiazolyl (e.g. 1,2,4-oxadiazolyl), triazolyl (such as 1,2,3-triazolyl or 1,2,4-triazolyl), benzothiazolyl, pyrimidinyl (e.g. 2-pyrimidinyl or 4-pyrimidinyl), benzothienyl,

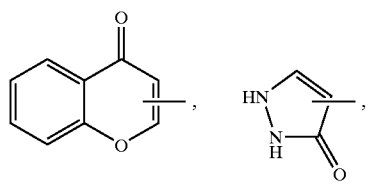

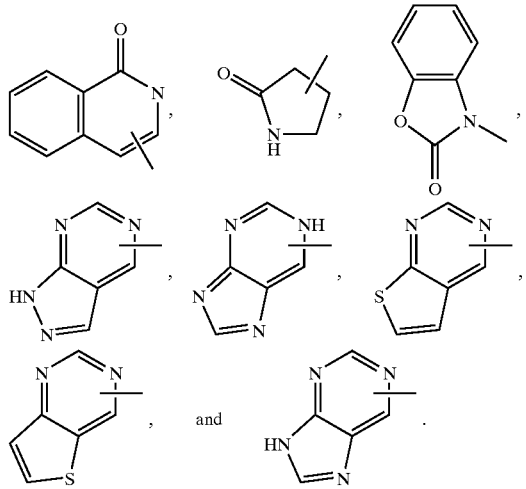

In a further aspect of the invention the ring system of $R^1$ may be optionally substituted by one or more (e.g. one, two, three or four) substituents independently selected from halogen (e.g. fluorine, chlorine, bromine or iodine); cyano; nitro; hydroxyl; carboxyl; $C_1$–$C_6$, preferably $C_1$–$C_4$, alkyl (especially methyl or ethyl); $C_1$–$C_6$, preferably $C_1$–$C_4$, hydroxyalkyl; $C_1$–$C_6$, preferably $C_1$–$C_4$, haloalkyl (e.g. trifluoromethyl); $C_1$–$C_6$, preferably $C_1$–$C_4$, alkoxy (especially methoxy, ethoxy, n-propoxy or isopropoxy); carboxy-substituted $C_1$–$C_6$, preferably $C_1$–$C_4$, alkoxy; $C_1$–$C_6$, preferably $C_1$–$C_4$, alkylthio (especially methylthio, ethylthio, n-propylthio and tert-butylthio); $C_1$–$C_6$, preferably $C_1$–$C_4$, alkylthiomethyl (particularly methylthiomethyl); $C_1$–$C_6$, preferably $C_1$–$C_4$, alkylcarbonylamino (especially methylcarbonylamino); —$NR^7R^8$; —$C(O)NR^7R^8$; $C_1$–$C_6$, preferably $C_1$–$C_4$, alkylcarbonyloxymethyl (particularly methylcarbonyloxymethyl); $C_1$–$C_6$, preferably $C_1$–$C_4$, alkoxycarbonyl (especially methoxycarbonyl or ethoxycarbonyl); $C_1$–$C_6$, preferably $C_1$–$C_4$, alkoxycarbonylpiperazinyl; furyl; phenyl; pyridinyl; pyrazinyl; halophenyl (especially chlorophenyl); thienyl; thienylmethyl; $C_1$–$C_6$, preferably $C_1$–$C_4$, alkylbenzyl (particularly methylbenzyl); and

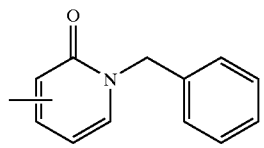

In a further aspect $R^1$ is an aromatic 5-membered heterocyclyl having 2, 3 or 4 ring nitrogen atoms (for example 1,2,4-triazole, 1,2,4-oxadiazole, 1,3,4-oxadiazole or tetrazole) substituted by one heteroaromatic ring (such as pyridine or pyrazole) which is itself optionally substituted by halogen or $C_1$–$C_4$ alkyl; or $R^1$ is halophenyl (for example phenyl optionally substituted (such as in the 4-position) by fluoro or chloro; such as 4-chlorophenyl or 4-fluorophenyl).

In a further aspect of the invention Q is oxygen or m is 0. In another aspect of the invention Q represents a sulphur atom or a group NH, C(O) or NHC(O).

In yet another aspect of the invention n is 1 or 2.

In a further aspect of the invention T represents a group NH, C(O)NH or NHC(O)NH. In another aspect of the invention T represents a NH or C(O)NH group. In a further aspect T is C(O)NH.

In one aspect $X^1$, $X^2$, $X^3$ and $X^4$ are all $CH_2$ or $CHR^{12}$, wherein the $R^{12}$ groups of $X^1$ and $X^3$ or $X^4$, or, $X^2$ and $X^3$ or $X^4$ join to form $CH_2CH_2$; provided always that at least two of $X^1$, $X^2$, $X^3$ and $X^4$ are $CH_2$. In a still further aspect $X^1$, $X^2$, $X^3$ and $X^4$ are all $CH_2$. Preferably, all four groups X represent $CH_2$.

It is preferred that each $R^2$ and $R^3$ independently represents a hydrogen atom or a methyl group, especially a hydrogen atom.

In one aspect $R^4$ and $R^5$ are hydrogen or $C_1$–$C_4$ alkyl. In another aspect $R^4$ and $R^5$ preferably each represent a hydrogen atom.

In another aspect of the invention $R^6$ represents a phenyl group optionally substituted by one or more (e.g. one, two, three or four) substituents independently selected from halogen (e.g. fluorine, chlorine, bromine or iodine), amino, nitro, cyano, sulphonyl, sulphonamido, $C_1$–$C_6$, preferably $C_1$–$C_4$, alkyl, $C_1$–$C_6$, preferably $C_1$–$C_4$, haloalkoxy, methylenedioxy and $C_1$–$C_6$, preferably $C_1$–$C_4$, alkylsulphonyl.

In another aspect of the invention $R^6$ represents a phenyl group optionally substituted by one or more (e.g. one, two, three or four) substituents independently selected from halogen (e.g. fluorine, chlorine, bromine or iodine), amino, nitro, cyano, sulphonyl, sulphonamido, $C_1$–$C_6$, preferably $C_1$–$C_4$, alkyl, $C_1$–$C_6$, preferably $C_1$–$C_4$, haloalkoxy and $C_1$–$C_6$, preferably $C_1$–$C_4$, alkylsulphonyl.

In a further aspect $R^6$ is phenyl optionally substituted by halogen or methylenedioxy. In a still further aspect $R^6$ is most preferably a phenyl group substituted by halogen. Examples of $R^6$ include 3-chlorophenyl, 4-chlorophenyl or, especially, 3,4-dichlorophenyl.

$R^7$ and $R^8$ each independently represent a hydrogen atom or a group selected from $C_1$–$C_6$, preferably $C_1$–$C_4$, hydroxyalkyl, $C_3$–$C_6$ cycloalkyl (cyclopropyl, cyclobutyl, cyclopentyl or cyclohexyl) and $C_1$–$C_6$, preferably $C_1$–$C_4$, alkyl optionally substituted by phenyl (e.g. one or two phenyl groups).

Most preferably, $R^7$ and $R^8$ each independently represent a hydrogen atom, or a group selected from $C_2$ hydroxyalkyl, cyclopropyl and $C_1$–$C_2$ alkyl optionally substituted by phenyl.

Compounds of the invention include all the Examples below, some of which are:

N-[1-(3,4-Dichlorobenzyl)-4-piperidinyl]-N-(4-methylbenzyl)amine,
N-[4-({[1-(3,4-Dichlorobenzyl)-4-piperidinyl]amino}methyl)phenyl]acetamide,
3-({[1-(3,4-Dichlorobenzyl)-4-piperidinyl]amino}methyl)phenol,
N-[(4-Chloro-1-methyl-1H-pyrazol-3-yl)methyl]-1-(3,4-dichlorobenzyl)-4-piperidinamine,
N-[1-(3,4-Dichlorobenzyl)-4-piperidinyl]-N-[(5-methyl-2-furyl)methyl]amine,
N-[1-(3,4-Dichlorobenzyl)-4-piperidinyl]-N-(4-nitrobenzyl)amine,
N-Benzyl-1-(3,4-dichlorobenzyl)-4-piperidinamine,
N-[1-(3,4-Dichlorobenzyl)-4-piperidinyl]-N-(4-fluorobenzyl)amine,
N-(2,6-Dichlorobenzyl)-1-(3,4-dichlorobenzyl)-4-piperidinamine,
N,1-Bis(3,4-dichlorobenzyl)-4-piperidinamine,
N-[1-(3,4-Dichlorobenzyl)-4-piperidinyl]-N-(2-pyridinylmethyl)amine,
N-[1-(3,4-Dichlorobenzyl)-4-piperidinyl]-N-[(3-methyl-2-thienyl)methyl]amine,
N-[1-(3,4-Dichlorobenzyl)-4-piperidinyl]-N-[(5-methyl-2-thienyl)methyl]amine,
5-({[1-(3,4-Dichlorobenzyl)-4-piperidinyl]amino}methyl)-2-methoxyphenol,
4-({[1-(3,4-Dichlorobenzyl)-4-piperidinyl]amino}methyl)-2-nitrophenol,
3-({[1-(3,4-Dichlorobenzyl)-4-piperidinyl]amino}methyl)-4H-chromen-4-one,
N-[(5-Chloro-1,3-dimethyl-1H-pyrazol-4-yl)methyl]-1-(3,4-dichlorobenzyl)-4-piperidinamine,
N-[(4-Chloro-1H-pyrazol-3-yl)methyl]-1-(3,4-dichlorobenzyl)-4-piperidinamine,
N-[1-(3,4-Dichlorobenzyl)-4-piperidinyl]-N-{[1-(4-methylbenzyl)-1H-pyrazol-5-yl]methyl}amine,
N-[1-(3,4-Dichlorobenzyl)-4-piperidinyl]-N-[(2-phenyl-1H-imidazol-4-yl)methyl]amine,
N-[(2-Chloro-3-quinolinyl)methyl]-1-(3,4-dichlorobenzyl)-4-piperidinamine,
N-[1-(3,4-Dichlorobenzyl)-4-piperidinyl]-N-[(6-methyl-2-pyridinyl)methyl]amine,
N-[1-(3,4-Dichlorobenzyl)-4-piperidinyl]-N-(3-quinolinylmethyl)amine,
[5-({[1-(3,4-Dichlorobenzyl)-4-piperidinyl]amino}methyl)-2-furyl]methyl acetate,
4-({[1-(3,4-Dichlorobenzyl)-4-piperidinyl]amino}methyl)-1,5-dimethyl-2-phenyl-1,2-dihydro-3H-pyrazol-3-one,
N-[1-(3,4-Dichlorobenzyl)-4-piperidinyl]-N-(4-pyridinylmethyl)amine,
5-({[1-(3,4-Dichlorobenzyl)-4-piperidinyl]amino}methyl)-2-nitrophenol,
N-[2-(tert-Butylsulfanyl)benzyl]-1-(3,4-dichlorobenzyl)-4-piperidinamine,
N-[1-(3,4-Dichlorobenzyl)-4-piperidinyl]-N-(4-ethylbenzyl)amine,
5-({[1-(3,4-Dichlorobenzyl)-4-piperidinyl]amino}methyl)-2-hydroxybenzoic acid,
N-(1,3-Benzodioxol-4-ylmethyl)-1-(3,4-dichlorobenzyl)-4-piperidinamine,
N-[1-(3,4-Dichlorobenzyl)-4-piperidinyl]-N-(1,3-thiazol-2-ylmethyl)amine,
N-[1-(3,4-Dichlorobenzyl)-4-piperidinyl]-N-[(5-ethyl-2-furyl)methyl]amine,
N-[1-(3,4-Dichlorobenzyl)-4-piperidinyl]-N-(2-quinolinylmethyl)amine,
N-[1-(3,4-Dichlorobenzyl)-4-piperidinyl]-N-(4-quinolinylmethyl)amine,
5-({[1-(3,4-Dichlorobenzyl)-4-piperidinyl]amino}methyl)-2-hydroxy-3-methoxybenzoic acid,
N-[(4-Bromo-1H-pyrazol-3-yl)methyl]-1-(3,4-dichlorobenzyl)-4-piperidinamine,
2-[2-({[1-(3,4-Dichlorobenzyl)-4-piperidinyl]amino}methyl)-6-methoxyphenoxy]acetic acid,
N-[(4-Bromo-1-methyl-1H-pyrazol-3-yl)methyl]-1-(3,4-dichlorobenzyl)-4-piperidinamine,
N-[1-(3,4-Dichlorobenzyl)-4-piperidinyl]-N-(4-iodobenzyl)amine,
3-({[1-(3,4-Dichlorobenzyl)-4-piperidinyl]amino}methyl)-6,7-dimethyl-4H-chromen-4-one,
N-[1-(3,4-Dichlorobenzyl)-4-piperidinyl]-N-(4-isopropoxybenzyl)amine,
N-[1-(3,4-Dichlorobenzyl)-4-piperidinyl]-N-[(1-methyl-1H-benzimidazol-2-yl)methyl]amine,
N-[1-(3,4-Dichlorobenzyl)-4-piperidinyl]-N-(3-methylbenzyl)amine,
N-[1-(3,4-Dichlorobenzyl)-4-piperidinyl]-N-(3-pyridinylmethyl)amine,
N-[1-(3,4-Dichlorobenzyl)-4-piperidinyl]-N-(2,4-dimethylbenzyl)amine, Ethyl 5-({[1-(3,4-dichlorobenzyl)-4-piperidinyl]amino}methyl)-2-methyl-3-furoate,
N-[1-(3,4-Dichlorobenzyl)-4-piperidinyl]-3-furamide,
N-[1-(3,4-Dichlorobenzyl)-4-piperidinyl]-4-[3-(4-pyridinyl)-1,2,4-oxadiazol-5-yl]butanamide,
2-{[5-(1-Benzyl-2-oxo-1,2-dihydro-3-pyridinyl)-4-methyl-4H-1,2,4-triazol-3-yl]sulfanyl}-N-[1-(3,4-dichlorobenzyl)-4-piperidinyl]propanamide,
N-[1-(3,4-Dichlorobenzyl)-4-piperidinyl]-6-methoxy-4-quinolinecarboxamide,
N-[1-(3,4-Dichlorobenzyl)-4-piperidinyl]-2-(2-furyl)-4-quinolinecarboxamide,
N-[1-(3,4-Dichlorobenzyl)-4-piperidinyl]-4-(2-methyl-1-oxo-1,2-dihydro-3-isoquinolinyl)butanamide,
3-(1,3-Benzothiazol-2-ylsulfanyl)-N-[1-(3,4-dichlorobenzyl)-4-piperidinyl]propanamide,
N-[1-(3,4-Dichlorobenzyl)-4-piperidinyl]-2-(3,5-dimethoxyphenyl)acetamide,
N-[1-(3,4-Dichlorobenzyl)-4-piperidinyl]-2-(2-methoxyphenyl)acetamide,
2-[5-Chloro-2-oxo-1,3-benzothiazol-3(2H)-yl]-N-[1-(3,4-dichlorobenzyl)-4-piperidinyl]acetamide,
N-[1-(3,4-Dichlorobenzyl)-4-piperidinyl]-2-[(4,6-dimethyl-2-pyrimidinyl)sulfanyl]acetamide,
2-(1-Benzothiophen-3-yl)-N-[1-(3,4-dichlorobenzyl)-4-piperidinyl]acetamide,
N-[1-(3,4-Dichlorobenzyl)-4-piperidinyl]-4-(3,4-dimethoxyphenyl)butanamide,
5-Cyclohexyl-N-[1-(3,4-dichlorobenzyl)-4-piperidinyl]pentanamide,
N-[1-(3,4-Dichlorobenzyl)-4-piperidinyl]-3-fluoro-2-methylbenzamide,
$N^1$-[1-(3,4-Dichlorobenzyl)-4-piperidinyl]-$N^2$-(1-phenylethyl)phthalamide,
2-Cyclopentyl-N-[1-(3,4-dichlorobenzyl)-4-piperidinyl]acetamide,
4-Chloro-N-[1-(3,4-dichlorobenzyl)-4-piperidinyl]-2-nitrobenzamide,
2,2-Dichloro-N-[1-(3,4-dichlorobenzyl)-4-piperidinyl]-1-methylcyclopropanecarboxamide,
tert-Butyl 4-[5-({[1-(3,4-dichlorobenzyl)-4-piperidinyl]amino}carbonyl)-2-methoxyphenyl]-1-piperazinecarboxylate,
N-[1-(3,4-Dichlorobenzyl)-4-piperidinyl]-5-oxo-1-(2-thienylmethyl)-3-pyrrolidinecarboxamide,
N-[1-(3,4-Dichlorobenzyl)-4-piperidinyl]-3-[2-oxo-1,3-benzoxazol-3(2H)-yl]propanamide,
N-[1-(3,4-Dichlorobenzyl)-4-piperidinyl]-4-fluorobenzamide,
N-[1-(3,4-Dichlorobenzyl)-4-piperidinyl]-2-methylbenzamide,
N-[1-(3,4-Dichlorobenzyl)-4-piperidinyl]-3-methylbenzamide,
N-[1-(3,4-Dichlorobenzyl)-4-piperidinyl]-4-(hydroxymethyl)benzamide,
$N^1$-[1-(3,4-Dichlorobenzyl)-4-piperidinyl]-$N^2$-{2-[(methylsulfanyl)methyl]-4-pyrimidinyl}-1,2-ethanediamine,
$N^1$-[1-(3,4-Dichlorobenzyl)-4-piperidinyl]-$N^2$-[2-(methylsulfanyl)-6-(trifluoromethyl)-4-pyrimidinyl]-1,2-ethanediamine,
$N^1$-[1-(3,4-Dichlorobenzyl)-4-piperidinyl]-$N^2$-[5-methoxy-2-(methylsulfanyl)-4-pyrimidinyl]-1,2-ethanediamine,
2-({4-[(2-{[1-(3,4-Dichlorobenzyl)-4-piperidinyl]amino}ethyl)amino]-2-pyrimidinyl}amino)-1-ethanol,
$N^4$-(2-{[1-(3,4-Dichlorobenzyl)-4-piperidinyl]amino}ethyl)-6-methyl-2,4-pyrimidinediamine,
$N^4$-(2-{[1-(3,4-Dichlorobenzyl)-4-piperidinyl]amino}ethyl)-$N^2$,6-dimethyl-2,4-pyrimidinediamine,
2-Chloro-$N^4$-cyclopropyl-$N^6$-(2-{[1-(3,4-dichlorobenzyl)-4-piperidinyl]amino}ethyl)-4,6-pyrimidinediamine,
$N^1$-[1-(3,4-Dichlorobenzyl)-4-piperidinyl]-$N^2$-(4-phenyl-2-pyrimidinyl)-1,2-ethanediamine,
$N^1$-[1-(3,4-Dichlorobenzyl)-4-piperidinyl]-$N^2$-[4-(trifluoromethyl)-2-pyrimidinyl]-1,2-ethanediamine,
$N^1$-[1-(3,4-Dichlorobenzyl)-4-piperidinyl]-$N^2$-[4-(propylsulfanyl)-2-pyrimidinyl]-1,2-ethanediamine,
$N^2$-(2-{[1-(3,4-Dichlorobenzyl)-4-piperidinyl]amino}ethyl)-$N^4$,6-dimethyl-2,4-pyrimidinediamine,
$N^4$-Cyclopropyl-$N^2$-(2-{[1-(3,4-dichlorobenzyl)-4-piperidinyl]amino}ethyl)-2,4-pyrimidinediamine,
$N^1$-[1-(3,4-Dichlorobenzyl)-4-piperidinyl]-$N^2$-[4-(3-pyridinyl)-2-pyrimidinyl]-1,2-ethanediamine,
$N^1$-[1-(3,4-Dichlorobenzyl)-4-piperidinyl]-$N^2$-[4-(2-thienyl)-2-pyrimidinyl]-1,2-ethanediamine,
$N^1$-[1-(3,4-Dichlorobenzyl)-4-piperidinyl]-$N^2$-[4-(2-thienyl)-2-pyrimidinyl]-1,2-ethanediamine,
$N^1$-[1-(3,4-Dichlorobenzyl)-4-piperidinyl]-$N^2$-(1-methyl-1H-pyrazolo[3,4-d]pyrimidin-4yl)-1,2-ethanediamine,
$N^1$-[1-(3,4-Dichlorobenzyl)-4-piperidinyl]-$N^2$-(1H-purin-6-yl)-1,2-ethanediamine,
$N^1$-[1-(3,4-Dichlorobenzyl)-4-piperidinyl]-$N^2$-(5-methylthieno[2,3-d]pyrimidin-4-yl)-1,2-ethanediamine,
$N^1$-[1-(3,4-Dichlorobenzyl)-4-piperidinyl]-$N^2$-(7-methylthieno[3,2-d]pyrimidin-4-yl)-1,2-ethanediamine,
$N^1$-[1-(3,4-Dichlorobenzyl)-4-piperidinyl]-$N^2$-(9-methyl-9H-purin-6-yl)-1,2-ethanediamine,
N-[1-(3,4-Dichlorobenzyl)-4-piperidinyl]-2-{[5-(trifluoromethyl)-2-pyridinyl]sulfanyl}acetamide,
N-[1-(3,4-Dichlorobenzyl)-4-piperidinyl]-2-(5-methyl-1-phenyl-1H-pyrazol-4-yl)acetamide,
N-[1-(3,4-Dichlorobenzyl)-4-piperidinyl]-5-oxo-5-phenylpentanamide,
2-[2-(4-Chlorophenyl)-5-methyl-1,3-thiazol-4-yl]-N-[1-(3,4-dichlorobenzyl)-4-piperidinyl]acetamide,
N-[1-(3,4-Dichlorobenzyl)-4-piperidinyl]-2-(phenylsulfanyl)acetamide,
N-[1-(3,4-Dichlorobenzyl)-4-piperidinyl]-2-(4-fluorophenyl)acetamide,
N-[1-(3,4-Dichlorobenzyl)-4-piperidinyl]-2-[2-(2-pyrazinyl)-1,3-thiazol-4-yl]acetamide,
N-[1-(3,4-Dichlorobenzyl)-4-piperidinyl]-2-[(5-phenyl-2-pyrimidinyl)sulfanyl]acetamide,
N-[1-(3,4-Dichlorobenzyl)-4-piperidinyl]-3-[3-(2-pyridinyl)-1,2,4-oxadiazol-5-yl]propanamide,
N-[1-(3,4-Dichlorobenzyl)-4-piperidinyl]-1H-benzimidazol-2-amine,
2-{[1-(3,4-Dichlorobenzyl)-4-piperidinyl]amino}-N-(3-methoxyphenyl)acetamide, dihydrochloride salt,
N-[1-(3,4-Dichlorobenzyl)-4-piperidinyl]-N'-(3,4-dichlorophenyl)urea,
N-[1-(3,4-Dichlorobenzyl)-4-piperidinyl]-N'-(3-methoxyphenyl)urea, and
N-[1-(3,4-Dichlorobenzyl)-4-piperidinyl]-N-(4-methoxybenzyl)amine, dihydrochloride salt.

The present invention further provides a process for the preparation of a compound of formula (I) or (Ia) which comprises:

(a) when n is at least 1, the $CR^2R^3$ group attached directly to T is $CHR^3$ and T is $NR^{10}$, reacting a compound of formula $$R^1-(Q)_m-(CR^2R^3)_{n'}-\overset{O}{\underset{R^3}{C}} \tag{II}$$

wherein n' is 0 or an integer from 1 to 3 and $R^1$, $R^2$, $R^3$, m and Q are as defined above, with a compound of formula $$R^{10}\underset{H}{N}-\overset{X^2-X^1}{\underset{X^3-X^4}{\diagdown}}N-Z-R^6 \tag{III}$$

or a salt thereof, wherein $X^1$, $X^2$, $X^3$, $X^4$, Z, $R^6$ and $R^{10}$ are as defined above, in the presence of a reducing agent; or (b) when n is at least 1, the $CR^2R^3$ group attached directly to T is $C(C_1-C_4 \text{ alkyl})_2$ and T is $NR^{10}$, reacting a compound of formula $$R^1-(Q)_m-(CR^2R^3)_{n'}-\overset{R^{2'}}{\underset{R^{3'}}{C}}-NHR^{10} \tag{IV}$$

wherein n' is 0 or an integer from 1 to 3, $R^{2'}$ and $R^{3'}$ each independently represent a $C_1-C_4$ alkyl group, and $R^1$, $R^2$, $R^3$, $R^{10}$, m and Q are as defined above, with a compound of formula $$O=\underset{X^3-X^4}{\overset{X^2-X^1}{\diagdown}}N-Z-R^6 \tag{V}$$

wherein $X^1$, $X^2$, $X^3$, $X^4$, Z and $R^6$ are as defined above, in the presence of a reducing agent; or (c) when T is $C(O)NR^{10}$, reacting a compound of formula $$R^1-(Q)_m-(CR^2R^3)_n-\overset{O}{\underset{OH}{C}} \tag{VI}$$

wherein $R^1$, $R^2$, $R^3$, Q, m and n are as defined above, with a compound of formula (III) or a salt thereof as defined in (a) above; or (d) when m is 1 and Q is $NR^9$, reacting a compound of formula (VII), $R^1-L^1$, wherein $L^1$ represents a leaving group (e.g. a halogen atom) and $R^1$ is as defined above, with a compound of formula $$NHR^9-(CR^2R^3)_n-T-\underset{X^3-X^4}{\overset{X^2-X^1}{\diagdown}}N-Z-R^6 \tag{VIII}$$

or a salt thereof, wherein n, T, $X^1$, $X^2$, $X^3$, $X^4$, Z, $R^2$, $R^3$, $R^6$ and $R^9$ are as defined above; or (e) when at least one of $R^4$ and $R^5$ represents a hydrogen atom, reacting a compound of formula $$R^1-(Q)_m-(CR^2R^3)_n-T-\underset{X^3-X^4}{\overset{X^2-X^1}{\diagdown}}NH \tag{IX}$$

or a salt thereof, wherein $R^1$, $R^2$, $R^3$, Q, m, n, $X^1$, $X^2$, $X^3$, $X^4$ and T are as defined above, with a compound of general formula (X), $R^6-C(O)-R^{20}$, wherein $R^{20}$ represents a hydrogen atom or a $C_1-C_4$ alkyl group and $R^6$ is as defined above, in the presence of a reducing agent; or (f) reacting a compound of formula (IX) as defined in (e) above, with a compound of formula $$\underset{R^6}{\overset{L^2}{\diagdown}}Z \tag{XI}$$

wherein $L^2$ represents a leaving group (e.g. a halogen atom) and Z and $R^6$ are as defined above; or (g) when T is $NR^{10}$, reacting a compound of formula $$R^1-(Q)_m-(CR^2R^3)_n-L^3 \tag{XII}$$

wherein $L^3$ represents a leaving group (e.g. a halogen atom) and $R^1$, $R^2$, $R^3$, m, n and Q are as defined above, with a compound of formula (III) or a salt thereof as defined in (a) above; or (h) when T is $NHC(O)NR^{10}$, reacting a compound of formula $$R^1-(Q)_m-(CR^2R^3)_n-N=C=O \tag{XIII}$$

wherein $R^1$, $R^2$, $R^3$, Q, m and n are as defined above, with a compound of formula (III) or a salt thereof as defined in (a) above; or (i) when T is C(O)NH, Z is $CH_2$, n is 1, $R^2$ and $R^3$ are hydrogen or $C_1-C_4$ alkyl and Q is oxygen or sulphur, reacting a compound of formula (XIV):

$$Hal-\overset{R^2}{\underset{R^3}{C}}-\overset{O}{C}-\underset{H}{N}-\overset{X^2-X^1}{\underset{X^3-X^4}{\diagdown}}N-Z-R^6 \tag{XIV}$$

wherein Hal is a suitable halogen (such as bromo or chloro), $R^2$, $R^3$, $X^1$, $X^2$, $X^3$, $X^4$, Z and $R^6$ are as defined above, with $R^1OH$ or $R^1SH$ in the presence of a suitable base (such as potassium carbonate or sodium or potassium hydroxide);

and optionally after (a), (b), (c), (d), (e), (f), (g), (h) or (i) forming a pharmaceutically acceptable salt or solvate of the compound of formula (I) or (Ia)obtained.

Compounds of formulae (II) to (XIV) are either commercially available, or are known in the literature or may be prepared using known techniques.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I) or (Ia) may involve, at an appropriate stage, the addition and subsequent removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of the invention and intermediates may be isolated from their reaction mixtures, and if necessary further purified, by using standard techniques.

The compounds of formula (I) and (Ia) have activity as pharmaceuticals, in particular as modulators of chemokine receptor activity. More particularly, the compounds have utility as modulators of the activity of chemokine receptors CCR1 and/or CCR3.

A further aspect of the invention involves the use of a compound of formula (I) or (Ia) in the treatment of conditions or diseases in which modulation of chemokine receptor activity is beneficial.

Thus, compounds of formula (I) or (Ia) may be used in the treatment of autoimmune, inflammatory, proliferative and hyperproliferative diseases and immunologically-mediated diseases including rejection of transplanted organs or tissues and Acquired Immunodeficiency Syndrome (AIDS). Examples of these conditions include:

(1) (the respiratory tract) obstructive airways diseases including chronic obstructive pulmonary disease (COPD); asthma, such as bronchial, allergic, intrinsic, extrinsic and dust asthma, particularly chronic or inveterate asthma (e.g. late asthma and airways hyperresponsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, osteoarthritis, seronegative spondyloarthropathies (including ankylosing spondylitis, psoriatic arthritis and Reiter's disease), Behcet's disease, Sjogren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;

(4) (gastrointestinal tract) Coeliac disease, proctitis, eosinopilic gastro-enteritis, mastocytosis, Crohn's disease, inflammatory bowel disease, irritable bowel syndrome, ulcerative colitis, food-related allergies which have effects remote from the gut, e.g., migraine, rhinitis and eczema;

(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura; and (6) (allograft rejection) acute and chronic following, for example, transplantation of kidney, heart, liver, lung, bone marrow, skin and cornea; and chronic graft versus host disease.

Thus, the present invention provides a compound of formula (I) or (Ia), or a pharmaceutically acceptable salt thereof, a solvate thereof or a solvate of a salt thereof, as hereinbefore defined for use in therapy.

In a further aspect, the present invention provides the use of a compound of formula (I) or (Ia), or a pharmaceutically acceptable salt thereof, a solvate thereof or a solvate of a salt thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

In another aspect the present invention provides the use of a compound of formula (I), wherein Z is $CR^4R^5$, $C(O)$ or $CR^4R^5-Z^1$; $Z^1$ is $C_{1-4}$ alkylene, $C_{2-4}$ alkenylene or $C(O)NH$: $R^1$ represents a $C_1-C_{12}$ alkyl group optionally substituted by one or more substituents independently selected from cyano, hydroxyl, $C_1-C_6$ alkoxy, $C_1-C_6$ alkylthio, $C_{3-7}$ cycloalkyl, $C_1-C_6$ alkoxycarbonyl and phenyl (itself optionally substituted by one or more of halogen, nitro, cyano, $C_1-C_6$ alkyl, $C_1-C_6$ haloalkyl, phenyl($C_1-C_6$ alkyl), $C_1-C_6$ alkoxy, $C_1-C_6$ haloalkoxy, $S(O)_2(C_1-C_6$ alkyl), $C(O)NH_2$, carboxy or $C_1-C_6$ alkoxycarbonyl); or $R^1$ represents $C_2-C_6$ alkenyl optionally substituted by phenyl (itself optionally substituted by one or more of halogen, nitro, cyano, $C_1-C_6$ alkyl, $C_1-C_6$ haloalkyl, phenyl($C_1-C_6$ alkyl), $C_1-C_6$ alkoxy, $C_1-C_6$ haloalkoxy, $S(O)_2(C_1-C_6$ alkyl), $C(O)NH_2$, carboxy or $C_1-C_6$ alkoxycarbonyl); or $R^1$ represents a 3- to 14-membered saturated or unsaturated ring system which optionally comprises up to two ring carbon atoms that form carbonyl groups and which optionally further comprises up to 4 ring heteroatoms independently selected from nitrogen, oxygen and sulphur, wherein the ring system is optionally substituted by one or more substituents independently selected from: halogen, cyano, nitro, oxo, hydroxy, $C_1-C_8$ alkyl, $C_1-C_6$ hydroxyalkyl, $C_1-C_6$ haloalkyl, $C_{1-6}$ alkoxy ($C_1-C_6$ alkyl), $C_3-C_7$ cycloalkyl($C_1-C_6$ alkyl), $C_1-C_6$ alkylthio($C_1-C_6$ alkyl), $C_1-C_6$ alkylcarbonyloxy($C_1-C_6$ alkyl), $C_1-C_6$ alkylS(O)$_2$($C_1-C_6$ alkyl), aryl($C_1-C_6$ alkyl), heterocyclyl($C_1-C_6$ alkyl), arylS(O)$_2$($C_1-C_6$ alkyl), heterocyclylS(O)$_2$($C_1-C_6$ alkyl), aryl($C_1-C_6$ alkyl)S(O)$_2$, heterocyclyl($C_1-C_6$ alkyl)S(O)$_2$, $C_2-C_6$ alkenyl, $C_1-C_6$ alkoxy, carboxy-substituted $C_1-C_6$ alkoxy, $C_1-C_6$ haloalkoxy, $C_1-C_6$ hydroxyalkoxy, $C_1-C_6$ alkylcarboxy-substituted $C_1-C_6$ alkoxy, aryloxy, heterocyclyloxy, $C_1-C_6$ alkylthio, $C_3-C_7$ cycloalkyl($C_1-C_6$ alkylthio), $C_3-C_6$ alkynylthio, $C_1-C_6$ alkylcarbonylamino, $C_1-C_6$ haloalkylcarbonylamino, $SO_3H$, $-NR^7R^8$, $-C(O)NR^{23}R^{24}$, $S(O)_2NR^{18}R^{19}$, $S(O)_2R^{20}$, $R^{25}C(O)$, carboxyl, $C_1-C_6$ alkoxycarbonyl, aryl and heterocyclyl; wherein the foregoing aryl and heterocyclyl moieties are optionally substituted by one or more of halogen, oxo, hydroxy, nitro, cyano, $C_1-C_6$ alkyl, $C_1-C_6$ haloalkyl, phenyl($C_1-C_6$ alkyl), $C_1-C_6$ alkoxy, $C_1-C_6$ haloalkoxy, $S(O)_2(C_1-C_6$ alkyl), $C(O)NH_2$, carboxy or $C_1-C_6$ alkoxycarbonyl; m is 0 or 1; Q represents an oxygen or sulphur atom or a group $NR^9$, $C(O)$, $C(O)NR^9$, $NR^9C(O)$ or $CH=CH$; n is 0, 1, 2, 3, 4, 5 or 6 provided that when n is 0, then m is 0; each $R^2$ and $R^3$ independently represents a hydrogen atom or a $C_1$–$C_4$ alkyl group, or $(CR^2R^3)_n$ represents $C_3$–$C_7$ cycloalkyl optionally substituted by $C_1$–$C_4$ alkyl; T represents a group $NR^{10}$, $C(O)NR^{10}$, $NR^{11}C(O)NR^{10}$ or $C(O)NR^{10}NR^{11}$; $X^1$, $X^2$, $X^3$ and $X^4$ are, independently, $CH_2$, $CHR^{12}$ {wherein each $R^{12}$ is, independently, $C_1$–$C_4$ alkyl or $C_3$–$C_7$ cycloalkyl($C_1$–$C_4$ alkyl)} or C=O; or, when they are $CHR^{12}$, the $R^{12}$ groups of $X^1$ and $X^3$ or $X^4$, or, $X^2$ and $X^3$ or $X^4$ join to form a two or three atom chain which is $CH_2CH_2$, $CH_2CH_2CH_2$, $CH_2OCH_2$ or $CH_2SCH_2$; provided always that at least two of $X^1$, $X^2$, $X^3$ and $X^4$ are $CH_2$; $R^4$ and $R^5$ each independently represent a hydrogen atom or a $C_1$–$C_4$ alkyl group; $R^6$ is aryl or heterocyclyl, both optionally substituted by one or more of: halogen, cyano, nitro, oxo, hydroxyl, $C_1$–$C_8$ alkyl, $C_1$–$C_6$ hydroxyalkyl, $C_1$–$C_6$ haloalkyl, $C_{1-6}$ alkoxy($C_1$–$C_6$ alkyl), $C_3$–$C_7$ cycloalkyl($C_1$–$C_6$ alkyl), $C_1$–$C_6$ alkylthio($C_1$–$C_6$ alkyl), $C_1$–$C_6$ alkylcarbonyloxy($C_1$–$C_6$ alkyl), $C_1$–$C_6$ alkylS(O)$_2$($C_1$–$C_6$ alkyl), aryl($C_1$–$C_6$ alkyl), heterocyclyl($C_1$–$C_6$ alkyl), arylS(O)$_2$($C_1$–$C_6$ alkyl), heterocyclylS(O)$_2$($C_1$–$C_6$ alkyl), aryl($C_1$–$C_6$ alkyl)S(O)$_2$, heterocyclyl($C_1$–$C_6$ alkyl)S(O)$_2$, $C_2$–$C_6$ alkenyl, $C_1$–$C_6$ alkoxy, carboxy-substituted $C_1$–$C_6$ alkoxy, $C_1$–$C_6$ haloalkoxy, $C_1$–$C_6$ hydroxyalkoxy, $C_1$–$C_6$ alkylcarboxy-substituted $C_1$–$C_6$ alkoxy, aryloxy, heterocyclyloxy, $C_1$–$C_6$ alkylthio, $C_3$–$C_7$ cycloalkyl($C_1$–$C_6$ alkylthio), $C_3$–$C_6$ alkynylthio, $C_1$–$C_6$ alkylcarbonylamino, $C_1$–$C_6$ haloalkylcarbonylamino, $SO_3H$, —$NR^{16}R^{17}$, —C(O)$NR^{21}R^{22}$, $S(O)_2NR^{13}R^{14}$, $S(O)_2R^{15}$, $R^{26}C(O)$, carboxyl, $C_1$–$C_6$ alkoxycarbonyl, aryl and heterocyclyl; wherein the foregoing aryl and heterocyclyl moieties are optionally substituted by one or more of halogen, nitro, cyano, $C_1$–$C_6$ alkyl, $C_1$–$C_6$ haloalkyl, phenyl($C_1$–$C_6$ alkyl), $C_1$–$C_6$ alkoxy, $C_1$–$C_6$ haloalkoxy, $S(O)_2(C_1$–$C_6$ alkyl), $C(O)NH_2$, carboxy or $C_1$–$C_6$ alkoxycarbonyl; $R^7$, $R^8$, $R^9$, $R^{10}$, $R^{11}$, $R^{13}$, $R^{14}$, $R^{16}$, $R^{17}$, $R^{18}$, $R^{19}$, $R^{21}$, $R^{22}$, $R^{23}$ and $R^{24}$ are, independently hydrogen, $C_1$–$C_6$ alkyl, $C_1$–$C_6$ haloalkyl, $C_1$–$C_6$ hydroxyalkyl, $C_3$–$C_7$ cycloalkyl, $C_3$–$C_7$ cycloalkyl($C_1$–$C_4$ alkyl) or phenyl($C_1$–$C_6$ alkyl); $R^{15}$ and $R^{20}$ are, independently, $C_1$–$C_6$ alkyl, $C_1$–$C_6$ hydroxyalkyl, $C_3$–$C_6$ cycloalkyl, $C_3$–$C_7$ cycloalkyl($C_1$–$C_4$ alkyl) or $C_1$–$C_6$ alkyl optionally substituted by phenyl; and, $R^{25}$ and $R^{26}$ are, independently, $C_1$–$C_6$ alkyl or phenyl (optionally substituted by one or more of halogen, nitro, cyano, $C_1$–$C_6$ alkyl, $C_1$–$C_6$ haloalkyl, phenyl($C_1$–$C_6$ alkyl), $C_1$–$C_6$ alkoxy, $C_1$–$C_6$ haloalkoxy, $S(O)_2(C_1$–$C_6$ alkyl), $C(O)NH_2$, carboxy or $C_1$–$C_6$ alkoxycarbonyl); or a pharmaceutically acceptable salt thereof, or solvate thereof, or a solvate of a salt thereof; in the manufacture of a medicament for the modulation of a chemokine receptor (such as CCR1 or CCR3). In a further aspect such medicament is for the treatment of asthma.

The invention also provides a method of treating an inflammatory disease in a person suffering from, or at risk of, said disease, which comprises administering to the person a therapeutically effective amount of a compound of formula (I) or (Ia), or a pharmaceutically acceptable salt thereof, a solvate thereof or a solvate of a salt thereof, as hereinbefore defined.

For the above-mentioned therapeutic uses the dosage administered will, of course, vary with the compound employed, the mode of administration, the treatment desired and the disorder indicated.

A compound of formula (I) or (Ia) or a pharmaceutically acceptable salt, solvate or solvate of a salt, may be used on its own but will generally be administered in the form of a pharmaceutical composition in which the formula (I) or (Ia) compound, salt, solvate or solvate of salt (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I) or (Ia), or a pharmaceutically acceptable salt, solvate or solvate of salt thereof, as hereinbefore defined, in association with a pharmaceutically acceptable adjuvant, diluent or carrier.

The invention further provides a process for the preparation of a pharmaceutical composition of the invention which comprises mixing a compound of formula (I) or (Ia), or a pharmaceutically acceptable salt, solvate or solvate of salt thereof, as hereinbefore defined, with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders, aerosols or granules, or by parenteral administration in the form of solutions or suspensions, or by subcutaneous administration or by rectal administration in the form of suppositories or transdermally.

The present invention will be further explained by reference to the following illustrative examples.

Examples 1–47

(i) tert-Butyl 1-(3,4-dichlorobenzyl)-4-piperidinylcarbamate

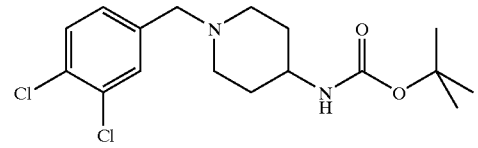

Sodium triacetoxyborohydride (6 g) was added to a stirred solution of 3,4-dichlorobenzaldehyde (4.2 g) and 1,1-dimethylethyl-4-piperidinyl carbamate (4 g) in dichloromethane (50 ml). The mixture was stirred at room temperature for 4 h then partitioned between ethyl acetate and aqueous sodium hydrogencarbonate. The organic layer was washed with water, dried and evaporated under reduced pressure. The residue was triturated with ether to give a white solid (3.5 g). Used directly.

(ii) 1-(3,4-Dichlorobenzyl)-4-piperidinamine, di-trifluoroacetate salt

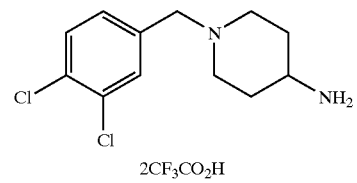

The product from step (i) (3.5 g) was treated with trifluoroacetic acid (10 ml) in dichloromethane (40 ml). After 72 h, the solution was evaporated, the residue triturated with ether and the solid (4.3 g) collected.

MS: APCI(+ve) 259/61 (M+1)

(iii) Examples 1–47

The product from step (ii) (2 mg), the appropriate aldehyde (2 equivalents), sodium triacetoxyborohydride (3 equivalents) and diisopropylethylamine (2 equivalents) in acetonitrile (0.08 ml) and 1-methyl-2-pyrrolidinone (0.12 ml) was left at room temperature for 24 h. The reaction mixture was evaporated to dryness and the residue dissolved in dimethylsuphoxide (0.4 ml).

Example 1

N-[1-(3,4-Dichlorobenzyl)-4-piperidinyl]-N-(4-methylbenzyl)amine

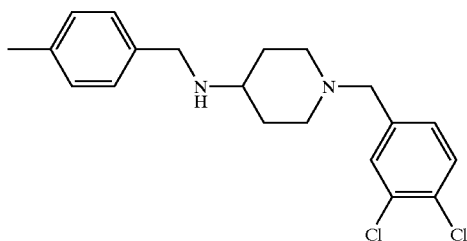

MS: APCI(+ve) 363 (M+1)

Example 2

N-[4-({[1-(3,4-Dichlorobenzyl)-4-piperidinyl]amino}methyl)phenyl]acetamide

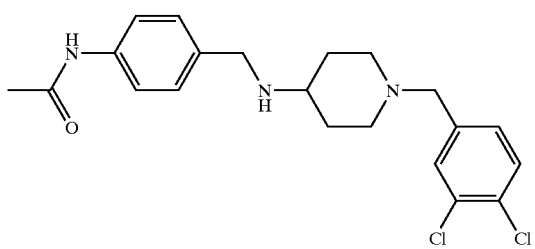

MS: APCI(+ve) 406 (M+1)

Example 3

3-({[1-(3,4-Dichlorobenzyl)-4-piperidinyl]amino}methyl)phenol

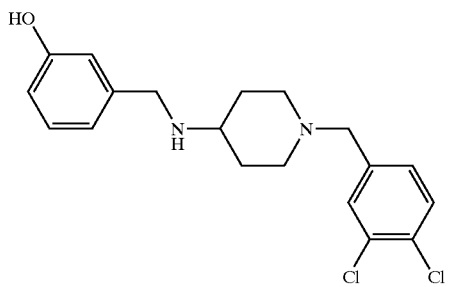

MS: APCI(+ve) 365 (M+1)

Example 4

N-[(4-Chloro-1-methyl-1H-pyrazol-3-yl)methyl]-1-(3,4-dichlorobenzyl)-4-piperidinamine

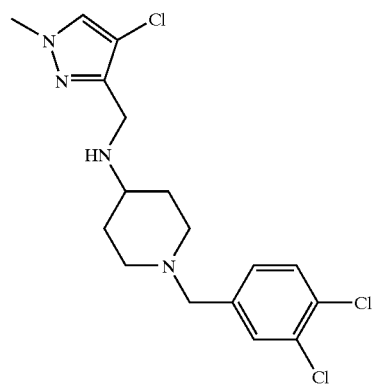

MS: APCI(+ve) 389 (M+1)

Example 5

N-[1-(3,4-Dichlorobenzyl)-4-piperidinyl]-N-[(5-methyl-2-furyl)methyl]amine

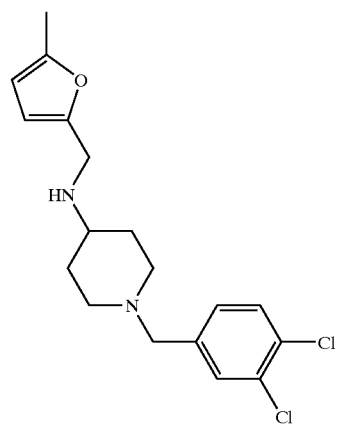

MS: APCI(+ve) 353 (M+1)

Example 6

N-[1-(3,4-Dichlorobenzyl)-4-piperidinyl]-N-(4-nitrobenzyl)amine

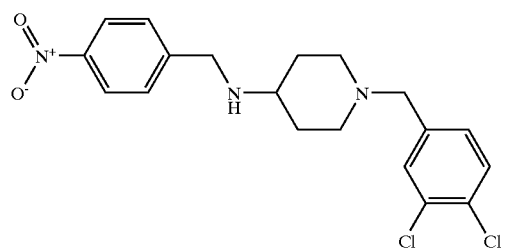

MS: APCI(+ve) 394 (M+1)

Example 7

N-Benzyl-1-(3,4-dichlorobenzyl)-4-piperidinamine

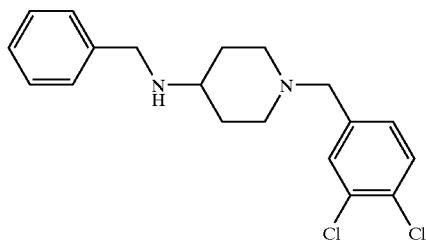

MS: APCI(+ve) 349 (M+1)

Example 8

N-[1-(3,4-Dichlorobenzyl)-4-piperidinyl]-N-(4-fluorobenzyl)amine

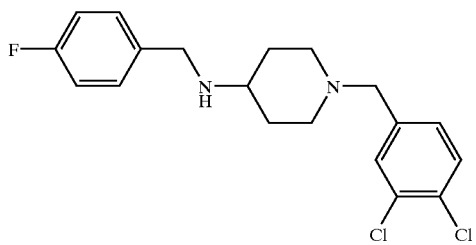

MS: APCI(+ve) 367 (M+1)

Example 9

N-(2,6-Dichlorobenzyl)-1-(3,4-dichlorobenzyl)-4-piperidinamine

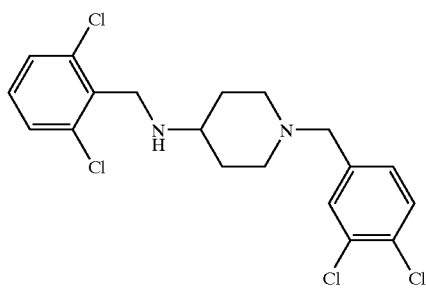

MS: APCI(+ve) 419 (M+1)

Example 10

N,1-Bis(3,4-dichlorobenzyl)-4-piperidinamine

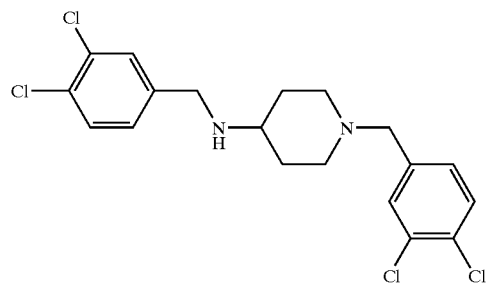

MS: APCI(+ve) 419 (M+1)

Example 11

N-[1-(3,4-Dichlorobenzyl)-4-piperidinyl]-N-(2-pyridinylmethyl)amine

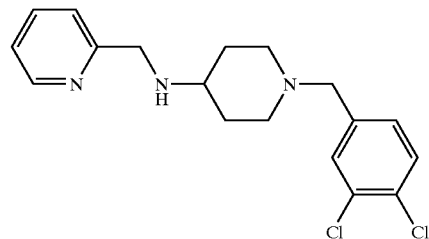

MS: APCI(+ve) 350 (M+1)

Example 12

N-[1-(3,4-Dichlorobenzyl)-4-piperidinyl]-N-[(3-methyl-2-thienyl)methyl]amine

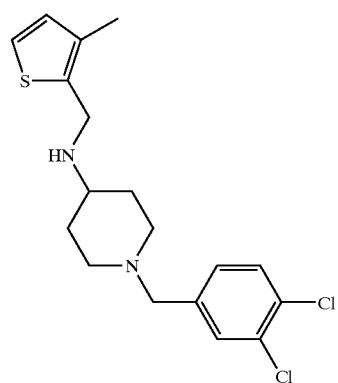

MS: APCI(+ve) 369 (M+1)

Example 13

N-[1-(3,4-Dichlorobenzyl)-4-piperidinyl]-N-[(5-methyl-2-thienyl)methyl]amine

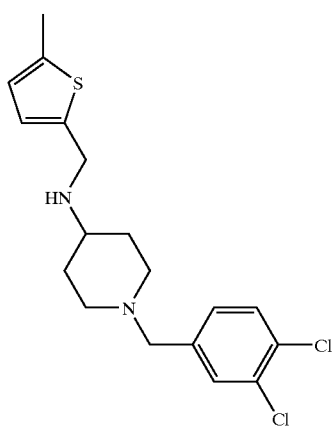

MS: APCI(+ve) 369 (M+1)

Example 14

5-({[1-(3,4-Dichlorobenzyl)-4-piperidinyl]amino}methyl)-2-methoxyphenol

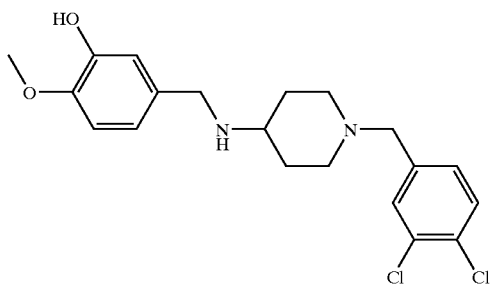

MS: APCI(+ve) 395 (M+1)

Example 15

4-({[1-(3,4-Dichlorobenzyl)-4-piperidinyl]amino}methyl)-2-nitrophenol

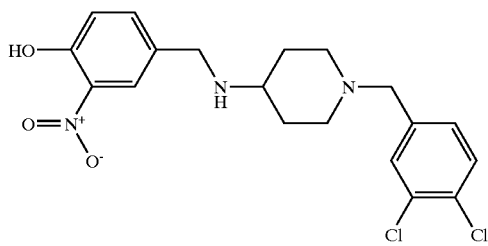

MS: APCI(+ve) 410 (M+1)

Example 16

3-({[1-(3,4-Dichlorobenzyl)-4-piperidinyl]amino}methyl)-4H-chromen-4-one

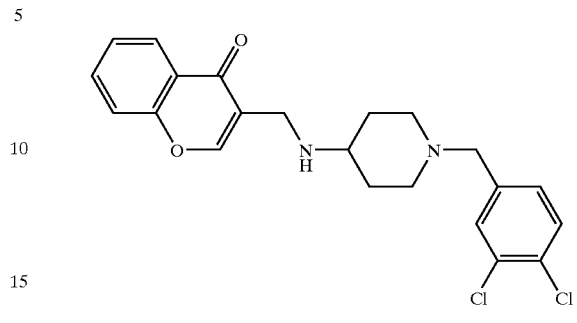

MS: APCI(+ve) 417 (M+1)

Example 17

N-[(5-Chloro-1,3-dimethyl-1H-pyrazol-4-yl)methyl]-1-(3,4-dichlorobenzyl)-4-piperidinamine

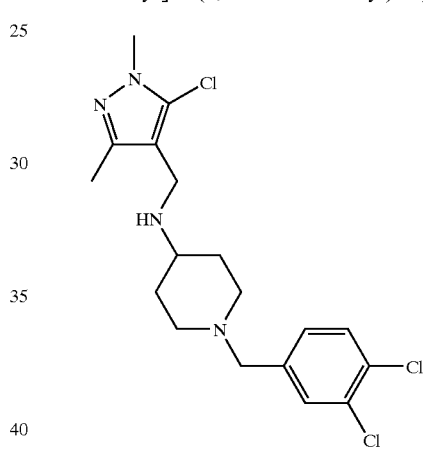

MS: APCI(+ve) 403 (M+1)

Example 18

N-[(4-Chloro-1H-pyrazol-3-yl)methyl]-1-(3,4-dichlorobenzyl)-4-piperidinamine

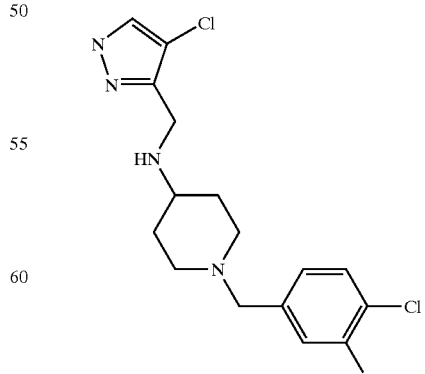

MS: APCI(+ve) 373 (M+1)

Example 19

N-[1-(3,4-Dichlorobenzyl)-4-piperidinyl]-N-{[1-(4-methylbenzyl)-1H-pyrazol-5-yl]methyl}amine

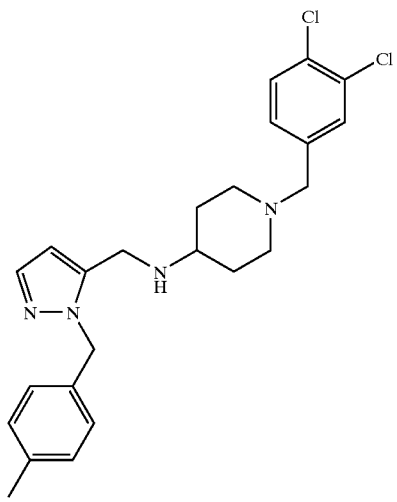

MS: APCI(+ve) 443 (M+1)

Example 20

N-[1-(3,4-Dichlorobenzyl)-4-piperidinyl]-N-[(2-phenyl-1H-imidazol-4-yl)methyl]amine

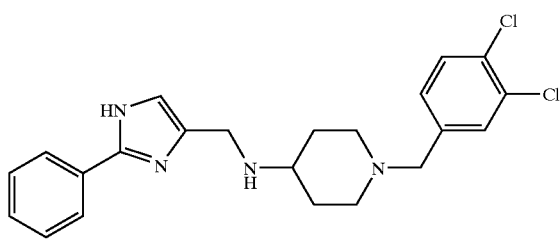

MS: APCI(+ve) 414 (M+1)

Example 21

N-[(2-Chloro-3-quinolinyl)methyl]-1-(3,4-dichlorobenzyl)-4-piperidinamine

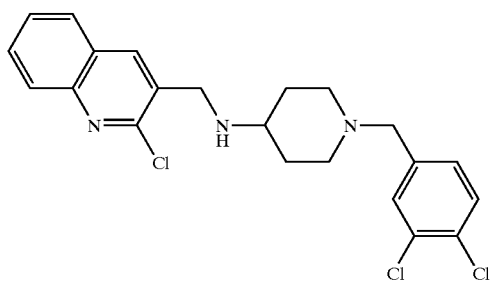

MS: APCI(+ve) 434 (M+1)

Example 22

N-[1-(3,4-Dichlorobenzyl)-4-piperidinyl]-N-[(6-methyl-2-pyridinyl)methyl]amine

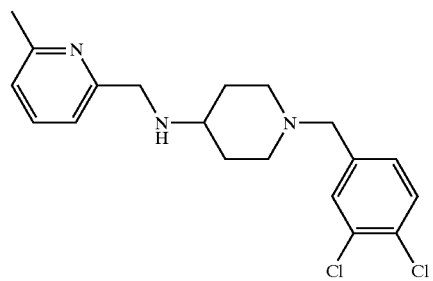

MS: APCI(+ve) 364 (M+1)

Example 23

N-[1-(3,4-Dichlorobenzyl)-4-piperidinyl]-N-(3-quinolinylmethyl)amine

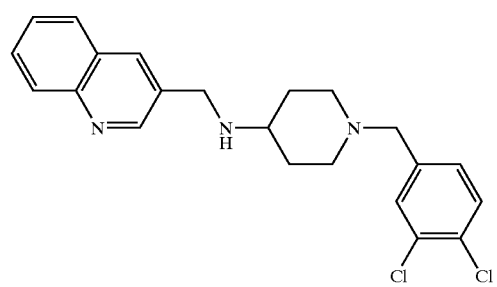

MS: APCI(+ve) 400 (M+1)

Example 24

[5-({[1-(3,4-Dichlorobenzyl)-4-piperidinyl]amino}methyl)-2-furyl]methyl acetate

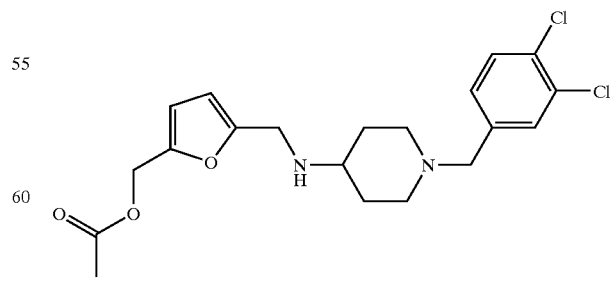

MS: APCI(+ve) 411 (M+1)

Example 25

4-({[1-(3,4-Dichlorobenzyl)-4-piperidinyl]amino}methyl)-1,5-dimethyl-2-phenyl-1,2-dihydro-3H-pyrazol-3-one

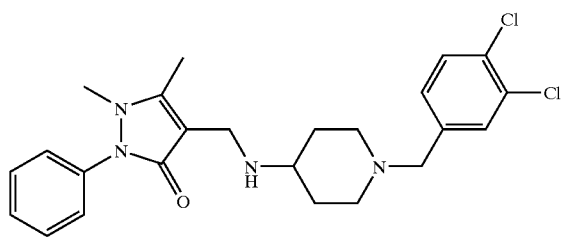

MS: APCI(+ve) 459 (M+1)

Example 26

N-[1-(3,4-Dichlorobenzyl)-4-piperidinyl]-N-(4-pyridinylmethyl)amine

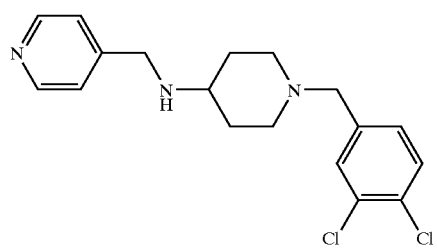

MS: APCI(+ve) 350 (M+1)

Example 27

5-({[1-(3,4-Dichlorobenzyl)-4-piperidinyl]amino}methyl)-2-nitrophenol

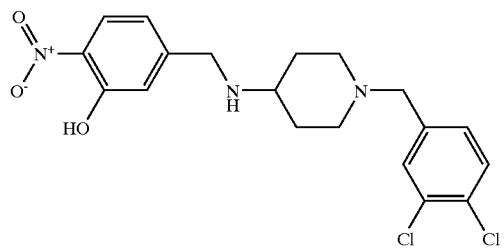

MS: APCI(+ve) 410 (M+1)

Example 28

N-[2-(tert-Butylsulfanyl)benzyl]-1-(3,4-dichlorobenzyl)-4-piperidinamine

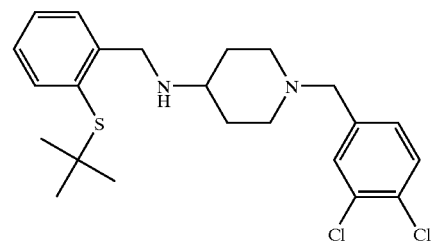

MS: APCI(+ve) 437 (M+1)

Example 29

N-[1-(3,4-Dichlorobenzyl)-4-piperidinyl]-N-(4-ethylbenzyl)amine

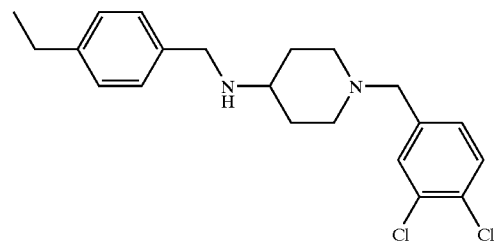

MS: APCI(+ve) 377 (M+1)

Example 30

5-({[1-(3,4-Dichlorobenzyl)-4-piperidinyl]amino}methyl)-2-hydroxybenzoic acid

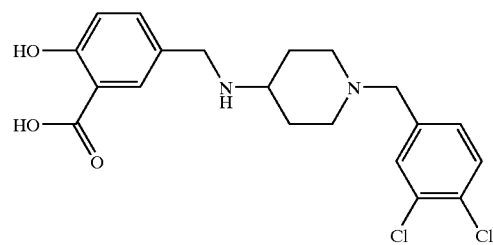

MS: APCI(+ve) 409 (M+1)

Example 31

N-(1,3-Benzodioxol-4-ylmethyl)-1-(3,4-dichlorobenzyl)-4-piperidinamine

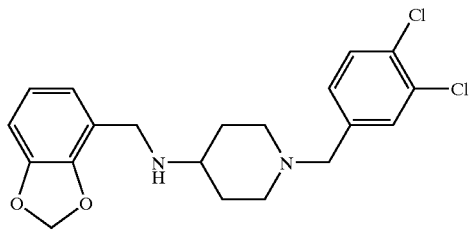

MS: APCI(+ve) 393 (M+1)

Example 32

N-[1-(3,4-Dichlorobenzyl)-4-piperidinyl]-N-(1,3-thiazol-2-ylmethyl)amine

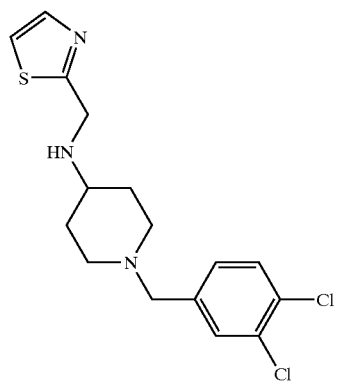

MS: APCI(+ve) 356 (M+1)

Example 33

N-[1-(3,4-Dichlorobenzyl)-4-piperidinyl]-N-[(5-ethyl-2-furyl)methyl]amine

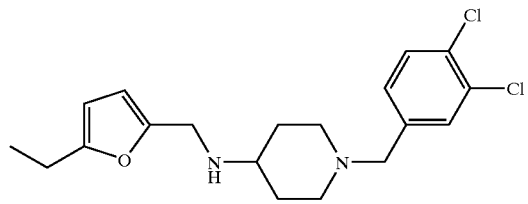

MS: APCI(+ve) 367 (M+1)

Example 34

N-[1-(3,4-Dichlorobenzyl)-4-piperidinyl]-N-(2-quinolinylmethyl)amine

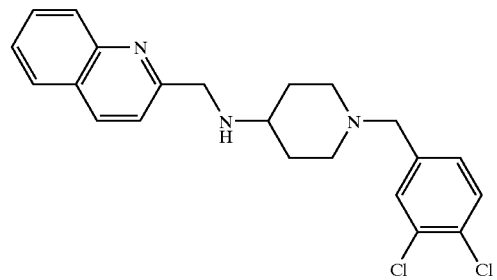

MS: APCI(+ve) 400 (M+1)

Example 35

N-[1-(3,4-Dichlorobenzyl)-4-piperidinyl]-N-(4-quinolinylmethyl)amine

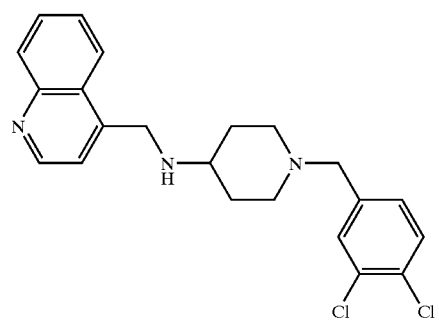

MS: APCI(+ve) 400 (M+1)

Example 36

5-({[1-(3,4-Dichlorobenzyl)-4-piperidinyl]amino}methyl)-2-hydroxy-3-methoxybenzoic acid

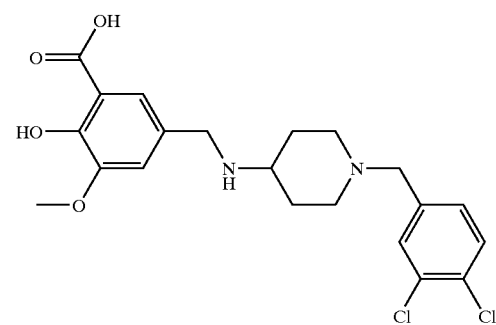

MS: APCI(+ve) 439 (M+1)

Example 37

N-[(4-Bromo-1H-pyrazol-3-yl)methyl]-1-(3,4-dichlorobenzyl)-4-piperidinamine

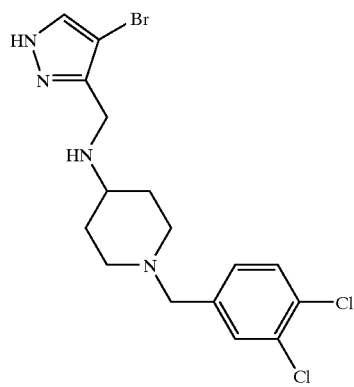

MS: APCI(+ve) 419 (M+1)

Example 38

2-[2-({[1-(3,4-Dichlorobenzyl)-4-piperidinyl]amino}methyl)-6-methoxyphenoxy]acetic acid

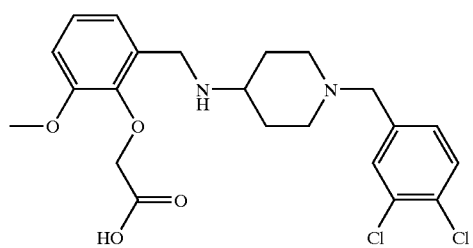

MS: APCI(+ve) 453 (M+1)

Example 39

N-[(4-Bromo-1-methyl-1H-pyrazol-3-yl)methyl]-1-(3,4-dichlorobenzyl)-4-piperidinamine

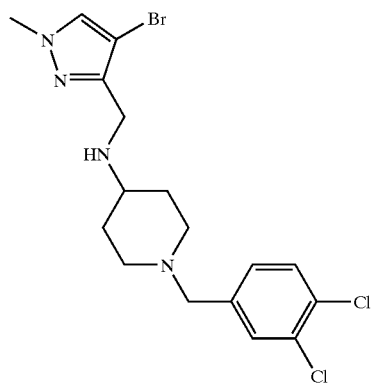

MS: APCI(+ve) 433 (M+1)

Example 40

N-[1-(3,4-Dichlorobenzyl)-4-piperidinyl]-N-(4-iodobenzyl)amine

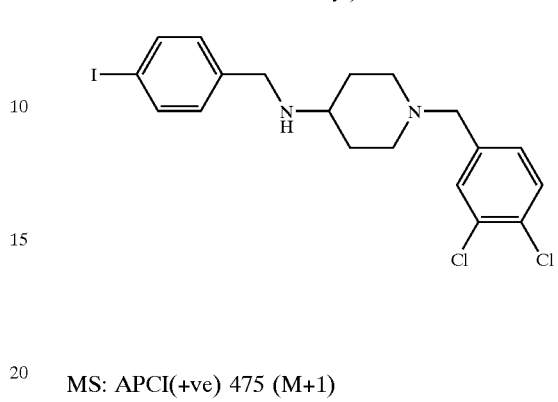

MS: APCI(+ve) 475 (M+1)

Example 41

3-({[1-(3,4-Dichlorobenzyl)-4-piperidinyl]amino}methyl)-6,7-dimethyl-4H-chromen-4-one

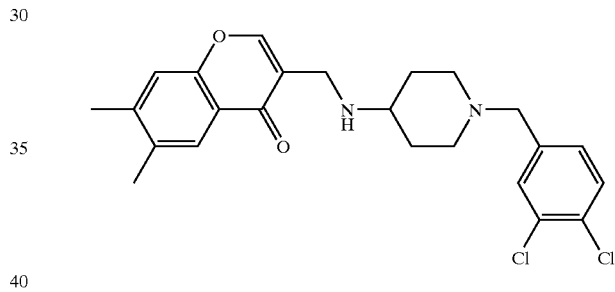

MS: APCI(+ve) 445 (M+1)

Example 42

N-[1-(3,4-Dichlorobenzyl)-4-piperidinyl]-N-(4-isopropoxybenzyl)amine

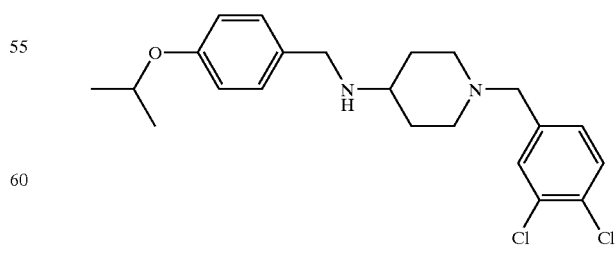

MS: APCI(+ve) 407 (M+1)

Example 43

N-[1-(3,4-Dichlorobenzyl)-4-piperidinyl]-N-[(1-methyl-1H-benzimidazol-2-yl)methyl]amine

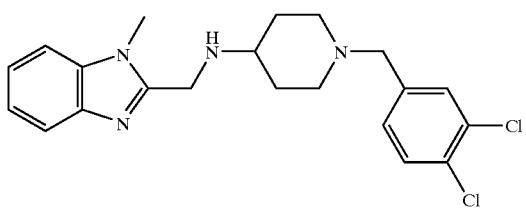

MS: APCI(+ve) 403 (M+1)

Example 44

N-[1-(3,4-Dichlorobenzyl)-4-piperidinyl]-N-(3-methylbenzyl)amine

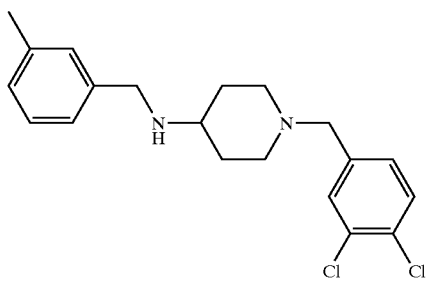

MS: APCI(+ve) 363 (M+1)

Example 45

N-[1-(3,4-Dichlorobenzyl)-4-piperidinyl]-N-(3-pyridinylmethyl)amine

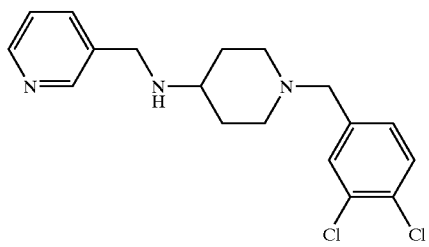

MS: APCI(+ve) 350 (M+1)

Example 46

N-[1-(3,4-Dichlorobenzyl)-4-piperidinyl]-N-(2,4-dimethylbenzyl)amine

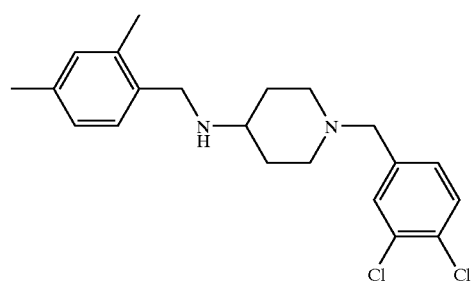

MS: APCI(+ve) 377 (M+1)

Example 47

Ethyl 5-({[1-(3,4-dichlorobenzyl)-4-piperidinyl]amino}methyl)-2-methyl-3-furoate

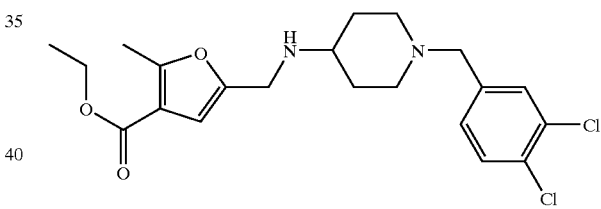

MS: APCI(+ve) 425 (M+1)

Examples 48–73

(i) Examples 48–73

Bromo-tris-pyrrolidino-phosphonium hexafluorophosphate (2 equiv) was added to a solution of the product from Example 1 step (ii) (hydrochloride salt) (1 mg), the appropriate acid (2 equivalents) and diisopropylethylamine (5 equivalents) in dimethylformamide (0.17 ml) and was left at room temperature for 24 h. The reaction mixture was evaporated to dryness and the residue dissolved in dimethylsulphoxide (0.3 ml).

Example 48

N-[1-(3,4-Dichlorobenzyl)-4-piperidinyl]-3-furamide

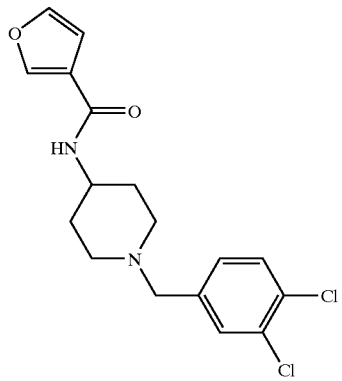

MS: APCI(+ve) 353 (M+1)

Example 49

N-[1-(3,4-Dichlorobenzyl)-4-piperidinyl]-4-[3-(4-pyridinyl)-1,2,4-oxadiazol-5-yl]butanamide

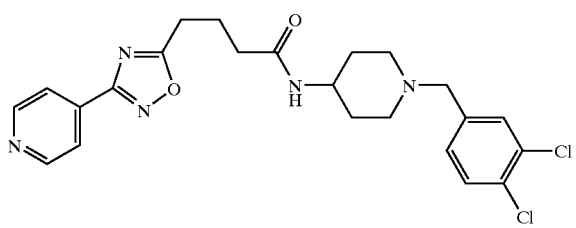

MS: APCI(+ve) 474 (M+1)

Example 50

2-{[5-(1-Benzyl-2-oxo-1,2-dihydro-3-pyridinyl)-4-methyl-4H-1,2,4-triazol-3-yl]sulfanyl}-N-[1-(3,4-dichlorobenzyl)-4-piperidinyl]propanamide

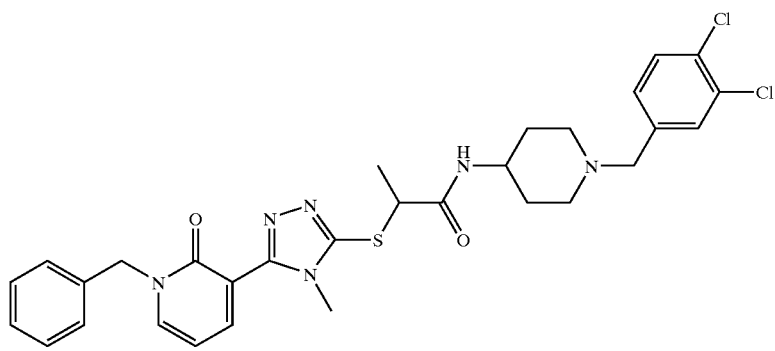

MS: APCI(+ve) 611 (M+1)

Example 51

N-[1-(3,4-Dichlorobenzyl)-4-piperidinyl]-6-methoxy-4-quinolinecarboxamide

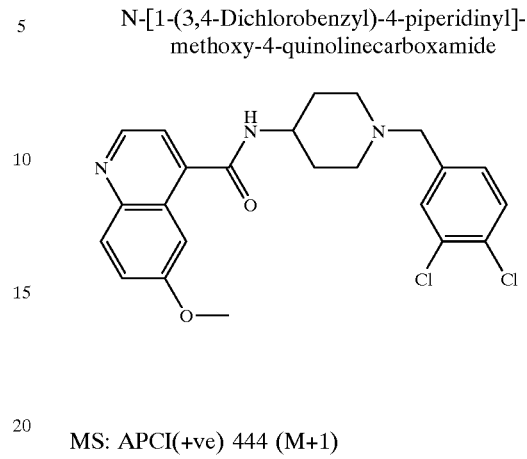

MS: APCI(+ve) 444 (M+1)

Example 52

N-[1-(3,4-Dichlorobenzyl)-4-piperidinyl]-2-(2-furyl)-4-quinolinecarboxamide

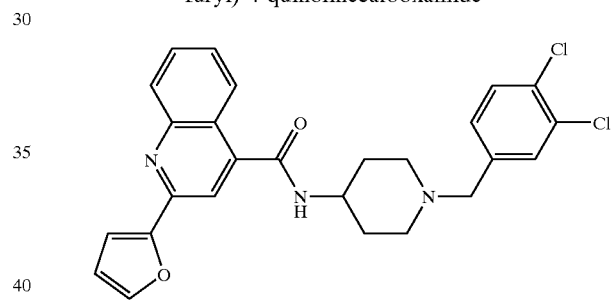

MS: APCI(+ve) 480 (M+1)

Example 53

N-[1-(3,4-Dichlorobenzyl)-4-piperidinyl]-4-(2-methyl-1-oxo-1,2-dihydro-3-isoquinolinyl)butanamide

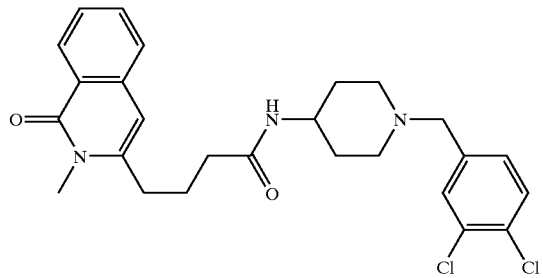

MS: APCI(+ve) 486 (M+1)

Example 54

3-(1,3-Benzothiazol-2-ylsulfanyl)-N-[1-(3,4-dichlorobenzyl)-4-piperidinyl]propanamide

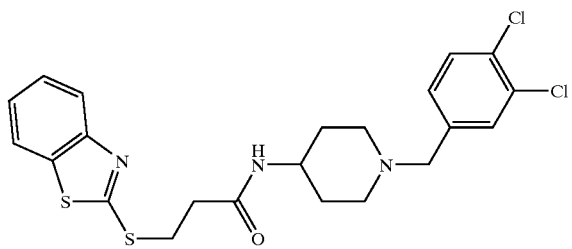

MS: APCI(+ve) 480 (M+1)

Example 55

N-[1-(3,4-Dichlorobenzyl)-4-piperidinyl]-2-(3,5-dimethoxyphenyl)acetamide

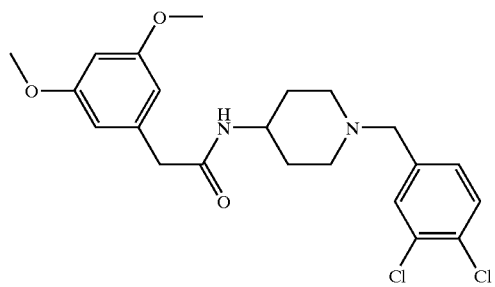

MS: APCI(+ve) 437 (M+1)

Example 56

N-[1-(3,4-Dichlorobenzyl)-4-piperidinyl]-2-(2-methoxyphenyl)acetamide

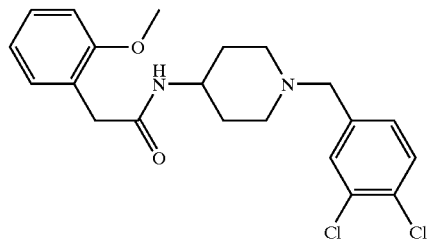

MS: APCI(+ve) 407 (M+1)

Example 57

2-[5-Chloro-2-oxo-1,3-benzothiazol-3(2H)-yl]-N-[1-(3,4-dichlorobenzyl)-4-piperidinyl]acetamide

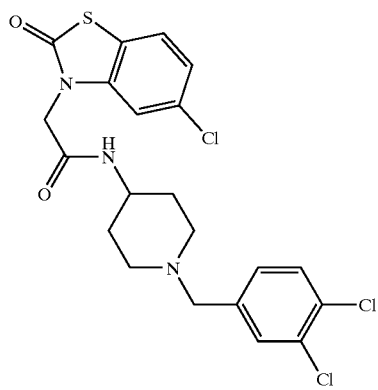

MS: APCI(+ve) 486 (M+1)

Example 58

N-[1-(3,4-Dichlorobenzyl)-4-piperidinyl]-2-[(4,6-dimethyl-2-pyrimidinyl)sulfanyl]acetamide

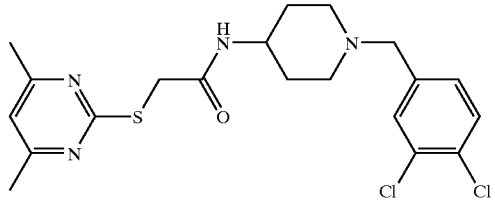

MS: APCI(+ve) 439 (M+1)

Example 59

2-(1-Benzothiophen-3-yl)-N-[1-(3,4-dichlorobenzyl)-4-piperidinyl]acetamide

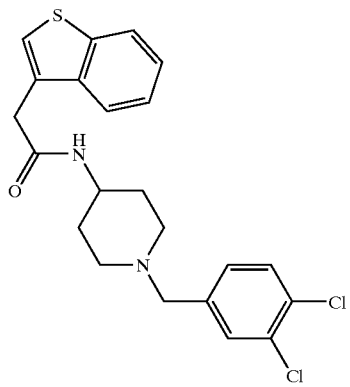

MS: APCI(+ve) 433 (M+1)

Example 60

N-[1-(3,4-Dichlorobenzyl)-4-piperidinyl]-4-(3,4-dimethoxyphenyl)butanamide

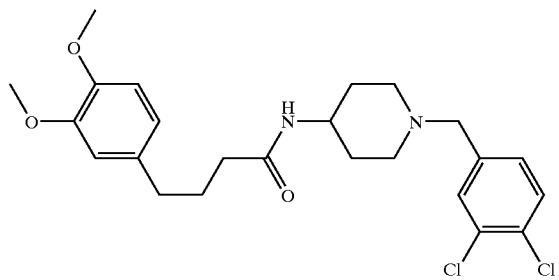

MS: APCI(+ve) 465 (M+1)

Example 61

5-Cyclohexyl-N-[1-(3,4-dichlorobenzyl)-4-piperidinyl]pentanamide

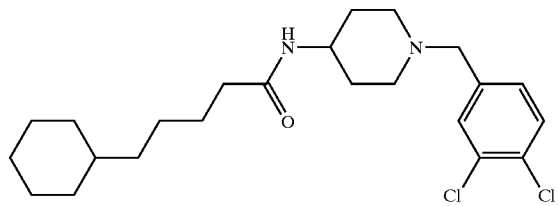

MS: APCI(+ve) 425 (M+1)

Example 62

N-[1-(3,4-Dichlorobenzyl)-4-piperidinyl]-3-fluoro-2-methylbenzamide

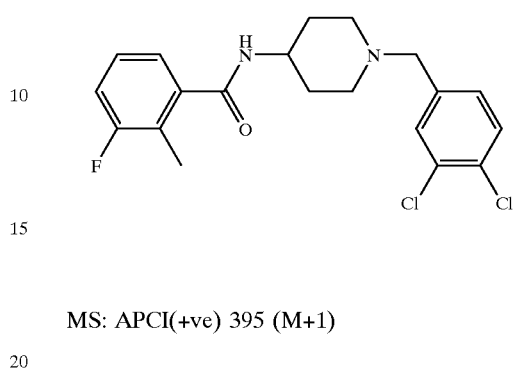

MS: APCI(+ve) 395 (M+1)

Example 63

$N^1$-[1-(3,4-Dichlorobenzyl)-4-piperidinyl]-$N^2$-(1-phenylethyl)phthalamide

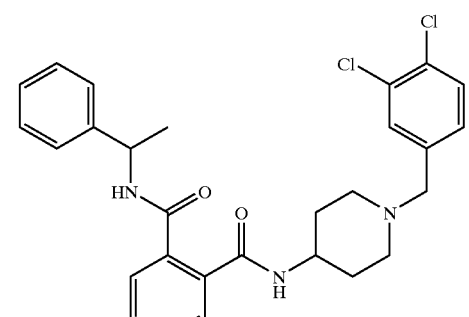

MS: APCI(+ve) 510 (M+1)

Example 64

2-Cyclopentyl-N-[1-(3,4-dichlorobenzyl)-4-piperidinyl]acetamide

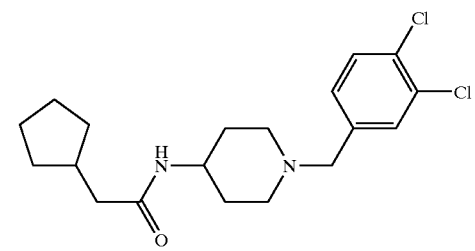

MS: APCI(+ve) 369 (M+1)

Example 65

4-Chloro-N-[1-(3,4-dichlorobenzyl)-4-piperidinyl]-2-nitrobenzamide

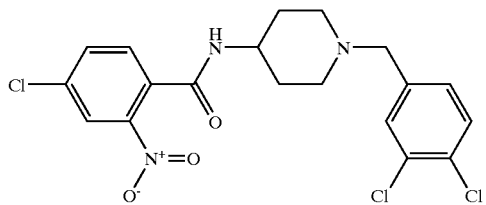

MS: APCI(+ve) 444 (M+1)

Example 66

2,2-Dichloro-N-[1-(3,4-dichlorobenzyl)-4-piperidinyl]-1-methylcyclopropanecarboxamide

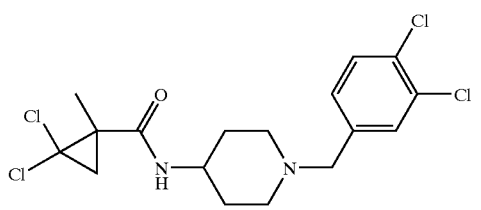

MS: APCI(+ve) 411 (M+1)

Example 67 tert-Butyl 4-[5-({[1-(3,4-dichlorobenzyl)-4-piperidinyl]amino}carbonyl)-2-methoxyphenyl]-1-piperazinecarboxylate

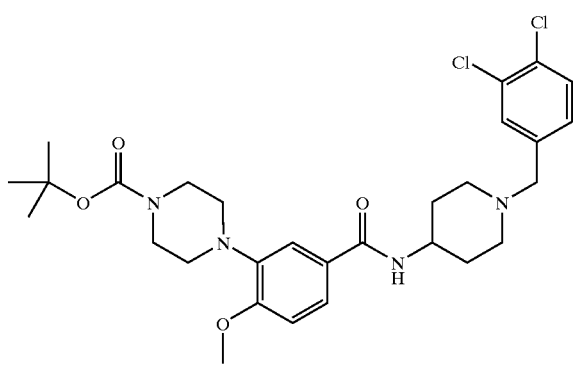

MS: APCI(+ve) 577 (M+1)

Example 68

N-[1-(3,4-Dichlorobenzyl)-4-piperidinyl]-5-oxo-1-(2-thienylmethyl)-3-pyrrolidinecarboxamide

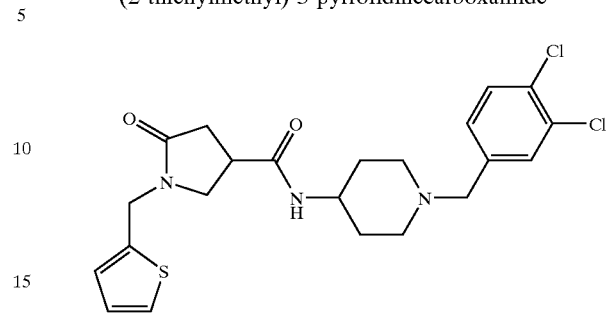

MS: APCI(+ve) 466 (M+1)

Example 69

N-[1-(3,4-Dichlorobenzyl)-4-piperidinyl]-3-[2-oxo-1,3-benzoxazol-3(2H)-yl]propanamide

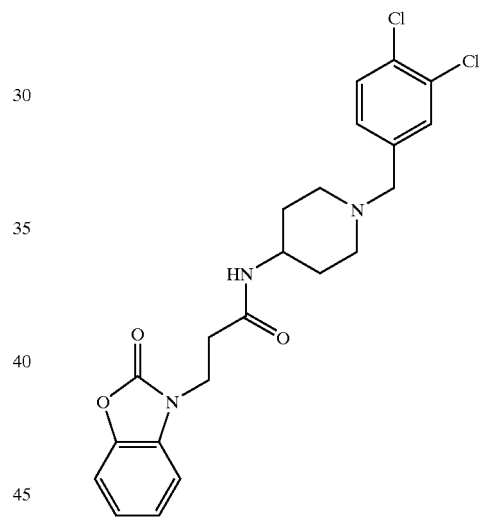

MS: APCI(+ve) 448 (M+1)

Example 70

N-[1-(3,4-Dichlorobenzyl)-4-piperidinyl]-4-fluorobenzamide

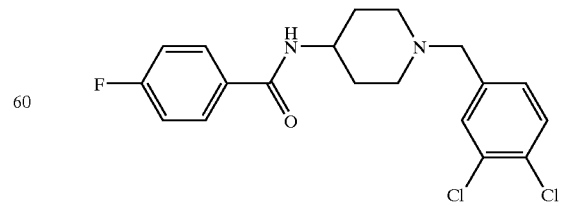

MS: APCI(+ve) 381 (M+1)

Example 71

N-[1-(3,4-Dichlorobenzyl)-4-piperidinyl]-2-methylbenzamide

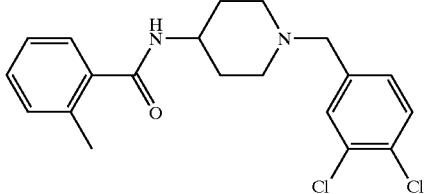

MS: APCI(+ve) 377 (M+1)

Example 72

N-[1-(3,4-Dichlorobenzyl)-4-piperidinyl]-3-methylbenazmide

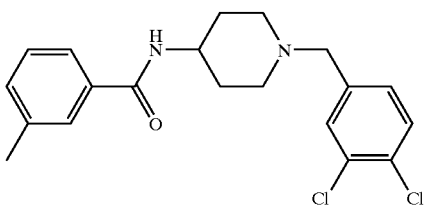

MS: APCI(+ve) 377 (M+1)

Example 73

N-[1-(3,4-Dichlorobenzyl)-4-piperidinyl]-4-(hydroxymethyl)benzamide

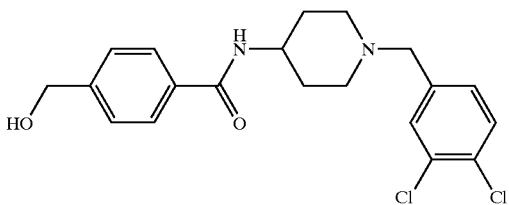

MS: APCI(+ve) 393 (M+1)

Examples 74–93

(i) 1-(3,4-Dichlorobenzyl)-4-piperidinone

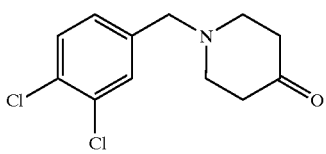

A solution of 3,4-dichlorobenzyl chloride (2.8 ml), 4-ketopiperidine hydrochloride monohydrate and triethylamine (8 ml) in dimethylformamide (30 ml) was stirred at room temperature for 20 h. The mixture was partitioned between water and ethyl acetate, the organic layer dried and evaporated under reduced pressure. Purification was by chromatography eluting with 40–50% ethyl acetate/isohexane. Yield 2.1 g.

MS: APCI(+ve) 258/60 (M+1)

(ii) tert-Butyl-2-{[1-(3,4-dichlorobenzyl)-4-piperidinyl]amino}ethylcarbamate

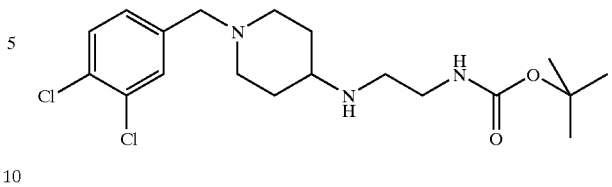

A solution of the product from step (i) (1.61 g), N-(tert-butoxycarbonyl)-ethylenediamine (1 g) and sodium triacetoxyborohydride (2.12 g) in dichloromethane (20 ml) was stirred at room temperature for 3 h. The mixture was partitioned between water and ethyl acetate, the organic layer dried and evaporated under reduced pressure. Yield 1.28 g.

MS: APCI(+ve) 402/4 (M+1)

(iii) N-1-[1-(3,4- Dichlorobenzyl)-4-piperidinyl]-1,2-ethanediamine, tri-trifluoroacetate Salt

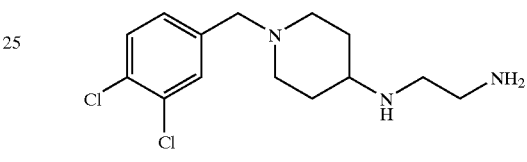

The product from step (ii) (1.28 g) was treated with trifluoroacetic acid (5 ml) in dichloromethane (10 ml). After 20 h, the solution was evaporated, the residue triturated with ether and the solid (1.62 g) collected.

MS: APCI(+ve) 302/4 (M+1)

(iv) Examples 74–93

The product from step (iii) (0.0026 g), the appropriate activated halo-aromatic (1.25 equivalents) and diisopropylethylamine (10 equivalents) in 1-methyl-2-pyrrolidinone (0.15 ml) was heated at 100° C. for 20 h. The reaction mixture was evaporated to dryness and the residue dissolved in dimethylsuphoxide (0.4 ml).

Example 74

$N^1$-[1-(3,4-Dichlorobenzyl)-4-piperidinyl]-$N^2$-{2-[(methylsulfanyl)methyl]-4-pyrimidinyl}-1,2-ethanediamine

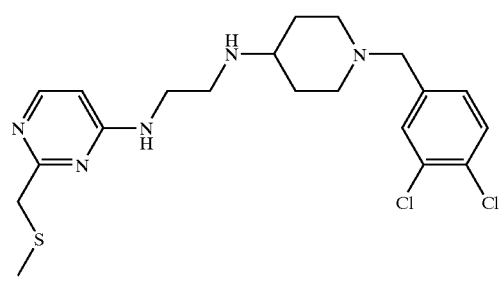

MS: APCI(+ve) 440(M+1)

Example 75

$N^1$-[1-(3,4-Dichlorobenzyl)-4-piperidinyl]-$N^2$-[2-(methylsulfanyl)-6-(trifluoromethyl)-4-pyrimidinyl]-1,2-ethanediamine

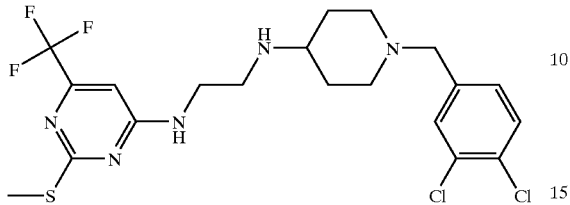

MS: APCI(+ve) 494(M+1)

Example 76

$N^1$-[1-(3,4-Dichlorobenzyl)-4-piperidinyl]-$N^2$-[5-methoxy-2-(methylsulfanyl)-4-pyrimidinyl]-1,2-ethanediamine

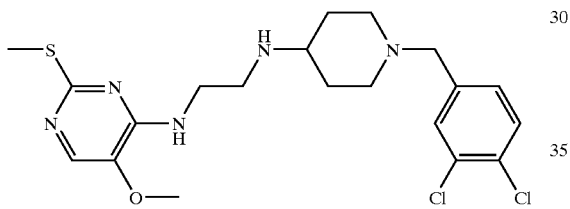

MS: APCI(+ve) 456(M+1)

Example 77

2-({4-[2-{[1-(3,4-Dichlorobenzyl)-4-piperidinyl]amino}ethyl)amino]-2-pyrimidinyl}amino)-1-ethanol

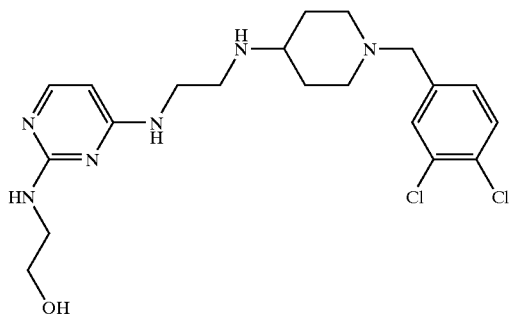

MS: APCI(+ve) 439(M+1)

Example 78

$N^4$-(2-{[1-(3,4-Dichlorobenzyl)-4-piperidinyl]amino}ethyl)-6-methyl-2,4-pyrimidinediamine

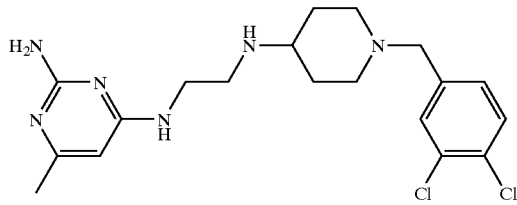

MS: APCI(+ve) 409(M+1)

Example 79

$N^4$-(2-{[1-(3,4-Dichlorobenzyl)-4-piperidinyl]amino}ethyl)-$N^2$,6-dimethyl-2,4-pyrimidinediamine

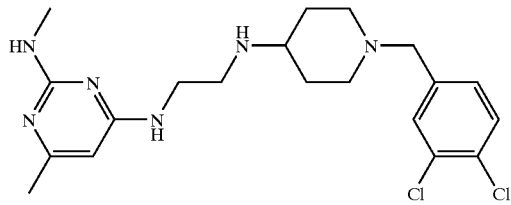

MS: APCI(+ve) 423(M+1)

Example 80

2-Chloro-$N^4$-cyclopropyl-$N^6$-(2-{[1-(3,4-dichlorobenzyl)-4-piperidinyl]amino}ethyl)-4,6-pyrimidinediamine

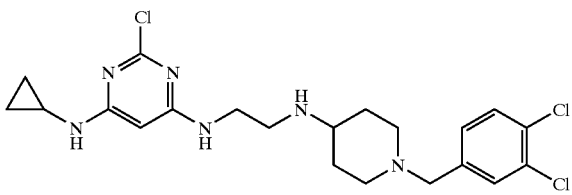

MS: APCI(+ve) 471(M+1)

Example 81

$N^1$-[1-(3,4-Dichlorobenzyl)-4-piperidinyl]-$N^2$-(4-phenyl-2-pyrimidinyl)-1,2-ethanediamine

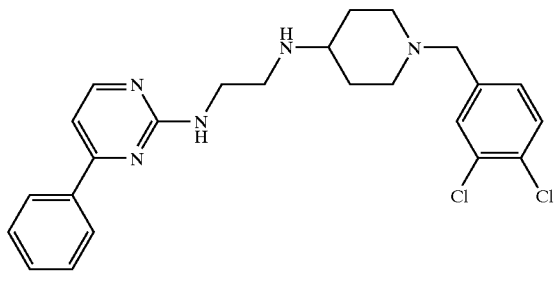

MS: APCI(+ve) 456(M+1)

Example 82

N$^1$-[1-(3,4-Dichlorobenzyl)-4-piperidinyl]-N$^2$-[4-(trifluoromethyl)-2-pyrimidinyl]-1,2-ethanediamine

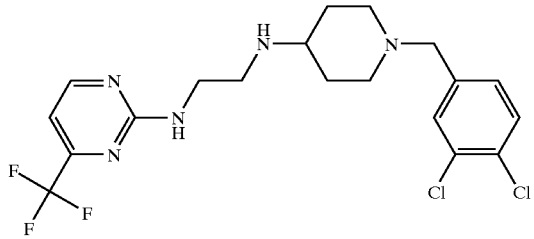

MS: APCI(+ve) 448(M+1)

Example 83

N$^1$-[1-(3,4-Dichlorobenzyl)-4-piperidinyl]-N$^2$-[4-(propylsulfanyl)-2-pyrimidinyl]-1,2-ethanediamine

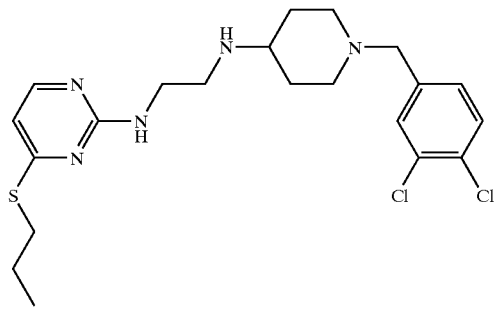

MS: APCI(+ve) 454(M+1)

Example 84

N$^2$-(2-{[1-(3,4-Dichlorobenzyl)-4-piperidinyl]amino}ethyl)-N$^4$,6-dimethyl-2,4-pyrimidinediamine

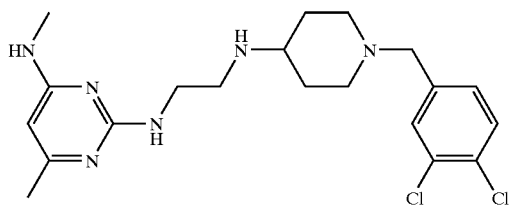

MS: APCI(+ve) 423(M+1)

Example 85

N$^4$-Cyclopropyl-N$^2$-(2-{[1-(3,4-dichlorobenzyl)-4-piperidinyl]amino}ethyl)-2,4-pyrimidinediamine

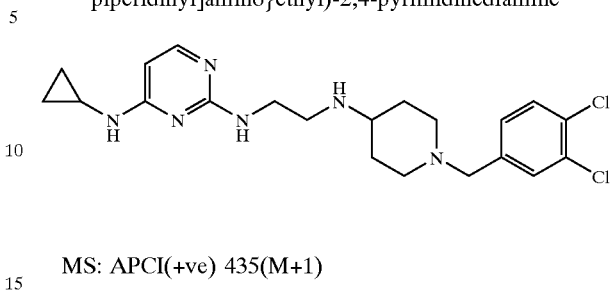

MS: APCI(+ve) 435(M+1)

Example 86

N$^1$-[1-(3,4-Dichlorobenzyl)-4-piperidinyl]-N$^2$-[4-(3-pyridinyl)-2-pyrimidinyl]-1,2-ethanediamine

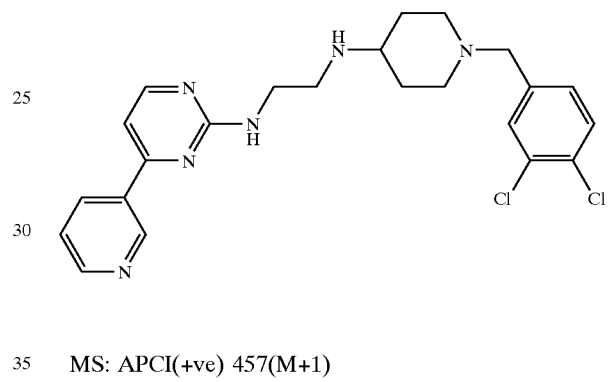

MS: APCI(+ve) 457(M+1)

Example 87

N$^1$-[1-(3,4-Dichlorobenzyl)-4-piperidinyl]-N$^2$-[4-(3-thienyl)-2-pyrimidinyl]-1,2-ethanediamine

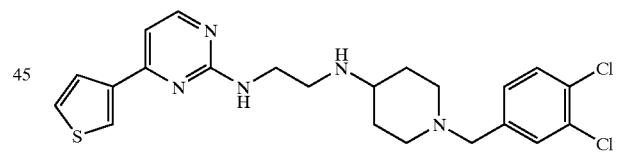

MS: APCI(+ve) 462(M+1)

Example 88

N$^1$-[1-(3,4-Dichlorobenzyl)-4-piperidinyl]-N$^2$-[4-(2-thienyl)-2-pyrimidinyl]-1,2-ethanediamine

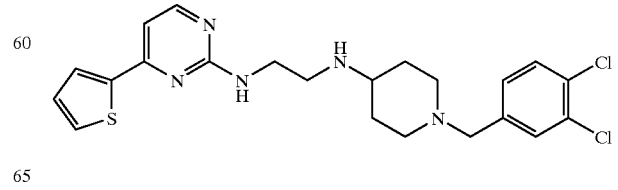

MS: APCI(+ve) 462(M+1)

Example 89

N$^1$-[1-(3,4-Dichlorobenzyl)-4-piperidinyl]-N$^2$-(1-methyl-1H-pyrazolo[3,4-d]pyrimidin-4-yl)-1,2-ethanediamine

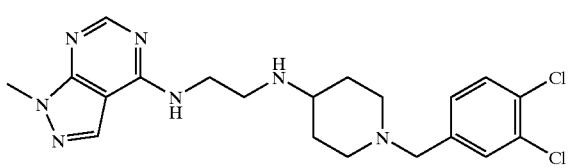

MS: APCI(+ve) 434(M+1)

Example 90

N$^1$-[1-(3,4-Dichlorobenzyl)-4-piperidinyl]-N$^2$-(1H-purin-6-yl)-1,2-ethanediamine

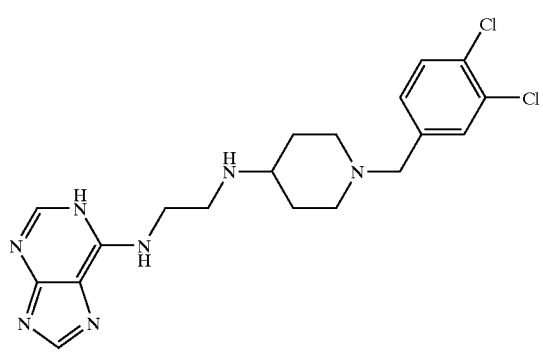

MS: APCI(+ve) 420(M+1)

Example 91

N$^1$-[1-(3,4-Dichlorobenzyl)-4-piperidinyl]-N$^2$-(5-methylthieno[2,3-d]pyrimidin-4-yl)-1,2-ethanediamine

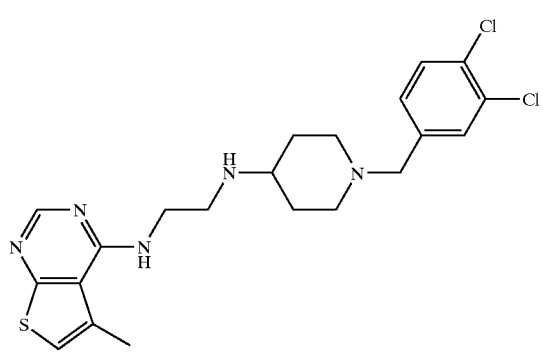

MS: APCI(+ve) 450(M+1)

Example 92

N$^1$-[1-(3,4-Dichlorobenzyl)-4-piperidinyl]-N$^2$-(7-methylthieno[3,2-d]pyrimidin-4-yl)-1,2-ethanediamine

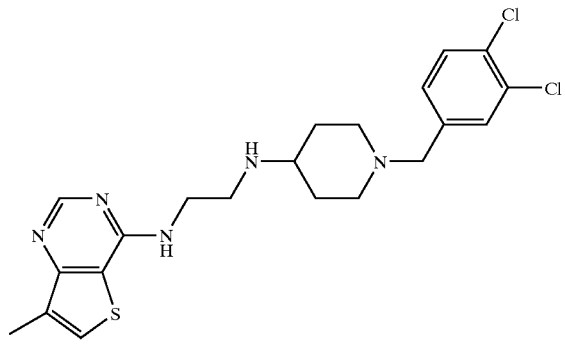

MS: APCI(+ve) 450(M+1)

Example 93

N$^1$-[1-(3,4-Dichlorobenzyl)-4-piperidinyl]-N$^2$-(9-methyl-9H-purin-6-yl)-1,2-ethanediamine

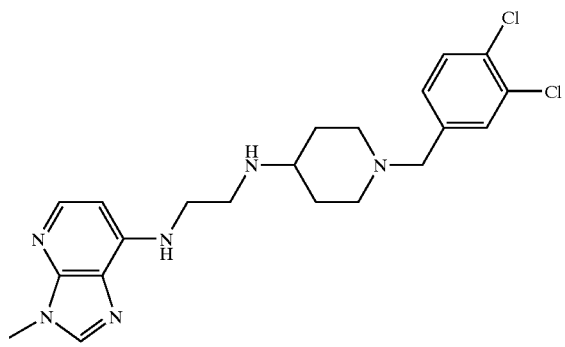

MS: APCI(+ve) 434(M+1)

Example 94

N-[1-(3,4-Dichlorobenzyl)-4-piperidinyl]-2-{[5-(trifluoromethyl)-2-pyridinyl]sulfanyl}acetamide

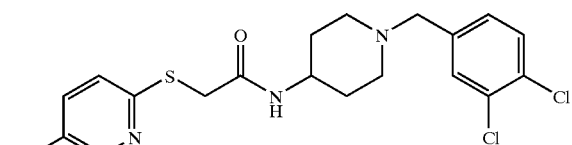

Carbonyldiimidazole (0.105 g) was added to a stirred solution of 2-{[5-(trifluoromethyl)-2-pyridinyl]sulfanyl}acetic acid (0.166 g) in dimethylformamide (2 ml). After 1 h a solution of the product from Example 1 step (ii) (0.3 g) in a solution of dimethylformamide and diisopropylethylamine (2 equivalents) (1.5 ml) was added and stirred at room temperature for 2 h. The mixture was partitioned between water and ethyl acetate, the organic layer washed with water, dried and evaporated under reduced pressure. The residue was triturated with ether and collected. Yield 0.084 g as a solid.

MS: APCI(+ve) 478/80 (M+1)

¹H NMR: δ (DMSO-d6) 8.76(s,1H), 8.11(d, 1H), 8.02(dd, 1H), 7.59–7.53(m, 3H), 7.29(dd, 1H), 3.91(s, 1H), 3.58–3.45(m, 1H), 3.44(s, 2H), 2.70(br d, 2H), 2.03(br t, 2H), 1.70(br d, 2H), 1.46–1.37(m, 2H).

MP: 98° C.

Example 95

N-[1-(3,4-Dichlorobenzyl)-4-piperidinyl]-2-(5-methyl-1-phenyl-1H-pyrazol-4-yl)acetamide

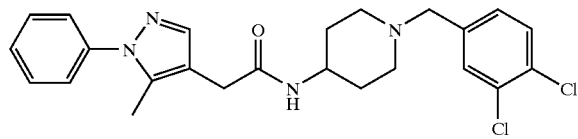

The title compound was prepared from the product of Example 1 step (ii) (0.3 g) and of 2-(5-methyl-1-phenyl-1H-pyrazol-4-yl)acetic acid (0.151 g) using the method of Example 94. Yield 0.18 g as a solid.

MS: APCI(+ve) 457/9 (M+1)

¹H NMR: δ (DMSO-d6) 7.90(d, 1H), 7.59–7.38(m, 8H), 7.29(dd, 1H), 3.54–3.50(m, 1H), 3.45(s, 2H), 3.24(s, 2H), 2.72(br d, 2H), 2.24(s, 3H), 2.03(br t, 2H), 1.72(br d, 2H), 1.46–1.37(m, 2H).

MP: 165° C.

Example 96

N-[1-(3,4-Dichlorobenzyl)-4-piperidinyl]-5-oxo-5-phenylpentanamide

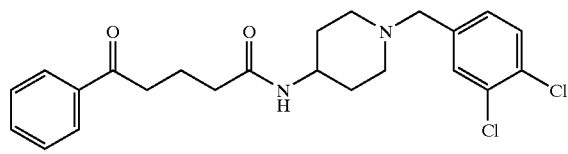

The title compound was prepared from the product of Example 1 step (ii) (0.3 g) and of 5-oxo-5-phenylpentanoic acid (0.134 g) using the method of Example 94. Yield 0.149 g as a solid.

MS: APCI(+ve) 433/5 (M+1)

¹H NMR: δ (DMSO-d6) 7.96–7.93(m, 2H), 7.72(d, 1H), 7.65–7.50(m, 5H), 7.28(dd, 1H), 3.57–3.48(m, 1H), 3.44(s, 2H), 3.01(t, 2H), 2.72–2.67(m, 2H), 2.13(t, 2H), 2.04–1.98(m, 2H), 1.86–1.79(m, 2H), 1.69(br s, 2H), 1.41–1.32(m, 2H).

MP: 130° C.

Example 97

2-[2-(4-Chlorophenyl)-5-methyl-1,3-thiazol-4-yl]-N-[1-(3,4-dichlorobenzyl)-4-piperidinyl]acetamide

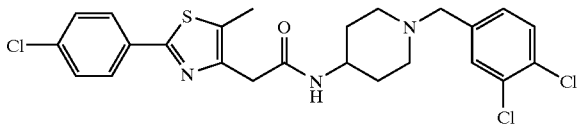

The title compound was prepared from the product of Example 1 step (ii) (0.3 g) and 2-[2-(4-chlorophenyl)-5-methyl-1,3-thiazol-4-yl]acetic acid (0.187 g) using the method of Example 94. Yield 0.1 g as a solid.

MS: APCI(+ve) 510/2 (M+1)

¹H NMR: δ (DMSO-d6) 8.00(d, 1H), 7.85–7.82(m, 2H), 7.59–7.52(m, 4H), 7.29(dd, 1H), 3.57–3.51(m, 3H), 3.44(s, 2H), 2.72(br d, 2H), 2.41(s, 3H), 2.06(t, 2H), 1.73(br d, 2H), 1.48–1.38(m, 2H).

MP: 170° C.

Example 98

N-[1-(3,4-Dichlorobenzyl)-4-piperidinyl]-2-(phenylsulfonyl)acetamide

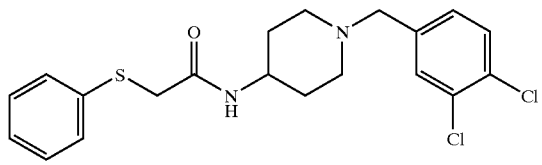

The title compound was prepared from the product of Example 1 step (ii) (0.3 g) and 2-(phenylsulfanyl)acetic acid (0.118 g) using the method of Example 94. Yield 0.056 g as a solid.

MS: APCI(+ve) 409(M+1)

¹H NMR: δ (DMSO-d6) 8.00(d, 1H), 7.57(d, 1H), 7.53(d, 1H), 7.36–7.27(m, 5H), 7.20–7.16(m, 1H), 3.61(s, 2H), 3.55–3.47(m, 1H), 3.44(s, 2H), 2.69–2.66(m, 2H), 2.02(t, 2H), 1.67–1.64(m, 2H), 1.41–1.31(m, 2H).

MP: 97–99° C.

Example 99

N-[1-(3,4-Dichlorobenzyl)-4-piperidinyl]-2-(4-fluorophenyl)acetamide

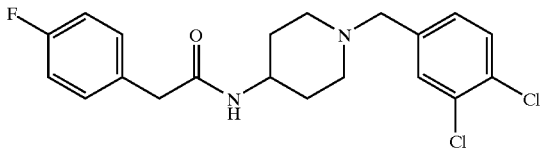

The title compound was prepared from the product of Example 1 step (ii) (0.3 g) and 2-(4-fluorophenyl)acetic acid (0.108 g) using the method of Example 94. Yield 0.15 g as a solid.

MS: APCI(+ve) 395 (M+1)

¹H NMR: δ (DMSO-d6) 7.98(d, 1H), 7.57(d, 1H), 7.53(d, 1H), 7.30–7.25(m, 3H), 7.13–7.07(m, 2H), 3.54–3.48(m,

1H), 3.45(s, 2H), 3.37(s, 2H), 2.72–2.69(m, 2H), 2.02(t, 2H), 1.71–1.68(m, 2H), 1.44–1.34(m, 2H).

MP: 144–7° C.

Example 100

N-[1-(3,4-Dichlorobenzyl)-4-piperidinyl]-2-[2-(2-pyrazinyl)-1,3-thiazol-4-yl]acetamide

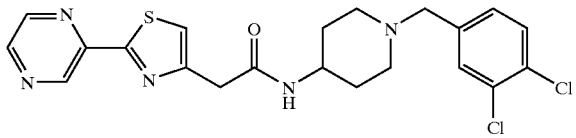

The title compound was prepared from the product of Example 1 step (ii) (0.3 g) and 2-[2-(2-pyrazinyl)-1,3-thiazol-4-yl]acetic acid (0.155 g) using the method of Example 94. Yield 0.08 g as a solid.

MS: APCI(+ve) 462 (M+1)

¹H NMR: δ (DMSO-d6) 9.25(d, 1H), 8.74–8.71(m, 2H), 8.07(d, 1H), 7.64(s, 1H), 7.59–7.54(m, 2H), 7.31–7.28(m, 1H), 3.69(s, 2H), 3.59–3.54(m, 1H), 3.45(s, 2H), 2.74–2.71 (m, 2H), 2.04(t, 2H), 1.76–1.74(m, 2H), 1.49–1.39(m, 2H).

MP: 186–9° C.

Example 101

N-[1-(3,4-Dichlorobenzyl)-4-piperidinyl]-2-[(5-phenyl-2-pyrimidinyl)sulfanyl]acetamide

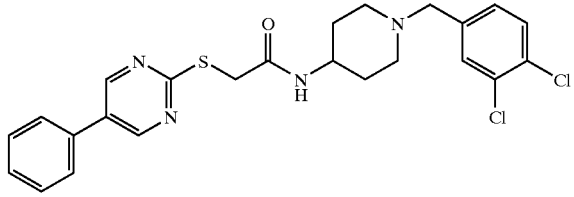

The title compound was prepared from the product of Example 1 step (ii) (0.3 g) and 2-[(5-phenyl-2-pyrimidinyl)sulfanyl]acetic acid (0.172 g) using the method of Example 94. Yield 0.115 g as a solid.

MS: APCI(+ve) 487/9 (M+1)

¹H NMR: δ (DMSO-d6) 8.96(s, 2H), 8.09(d, 1H), 7.78–7.75 (m, 2H), 7.58–7.43(m, 5H), 7.28(dd, 1H), 3.91(s, 2H), 3.59–3.52(m, 1H), 3.44(s, 2H), 2.70(br d, 2H), 2.03(br t, 2H), 1.72(br d, 2H), 1.47–1.38(m, 2H).

MP: 157° C.

Example 102

N-[1-(3,4-Dichlorobenzyl)-4-piperidinyl]-3-[3-(2-pyridinyl)-1,2,4-oxadiazol-5-yl]propanamide

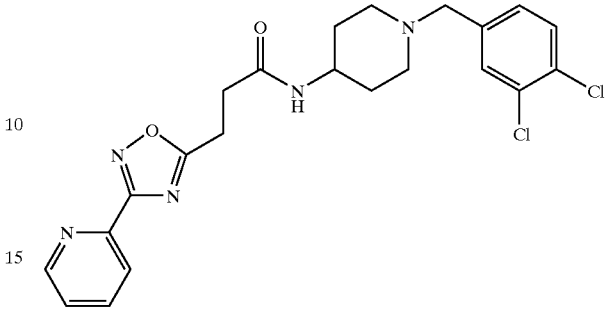

The title compound was prepared from the product of Example 1 step (ii) (0.9 g) and 3-[3-(2-pyridinyl)-1,2,4-oxadiazol-5-yl]propanoic acid (0.3 g) using the method of Example 94. Yield 0.074 g as a solid.

MS: APCI(+ve) 460/2 (M+1)

¹H NMR: δ (DMSO-d6) 8.76–8.74(m, 1H), 8.05–7.99(m, 2H), 7.94(d, 1H), 7.61–7.56(m, 2H), 7.52(d, 1H), 7.28(dd, 1H), 3.56–3.48(m, 1H), 3.43(s, 2H), 3.19(t, 2H), 2.71–2.66 (m, 4H), 2.03(t, 2H), 1.69(br d, 2H), 1.42–1.33(m, 2H).

MP: 155° C.

Example 103

N-[1-(3,4-Dichlorobenzyl)-4-piperidinyl]-1H-benzimidazol-2-amine

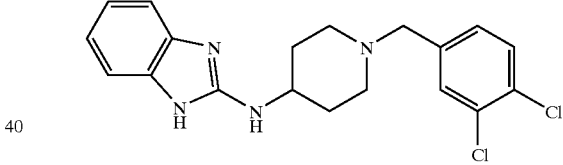

(i) Ethyl 4-(1H-benzimidazol-2-ylamino)-1-piperidinecarboxylate

A solution of 2-chlorobenzimidazole (1 g) and ethyl 4-amino-1-piperidinecarboxylate (2 g) in 1-methyl-2-pyrrolidinone was heated at 130° C. for 24 h. The mixture was partitioned between water and ethyl acetate, the organic layer washed with water, dried and evaporated under reduced pressure. Purification was by chromatography eluting with 1% triethylamine/5% methanol in dichloromethane. Yield 0.630 g as a solid.

TOF MS ES+ 289.1652 (M+1)

(ii) N-(4-Piperidinyl)-1H-benzimidazol-2-amine, dihydrochloride salt

The product from step (i) (0.58 g) was heated under reflux with 5M hydrochloric acid (20 ml) for 24 h. The solvent was evaporated under reduced pressure, the residue azetroped with toluene, washed with ether. Yield 0.58 g as a solid.

TOF MS ES+ 217.1452 (M+1)

(iii) N-[1-(3,4-Dichlorobenzyl)-4-piperidinyl]-1H-benzimidazol-2-amine

Triethylamine (0.223 ml) was added to a stirred suspension of the product from step (ii) (0.2 g) in dimethylformamide. After 5 min 3,4-dichlorobenzaldehyde (0.175 g) then sodium triacetoxyborohydride (0.212 g) was added and the mixture stirred at room temperature for 3 h. The mixture was partitioned between 2M hyrochloric acid and ether, the aqueous layer was basified with aqueous sodium hydrogencarbonate and extracted with ethyl acetate. The organic layer was dried and evaporated under reduced pressure. The residue was triturated with ethyl acetate/ether and the solid collected. Yield 0.045 g.

TOF MS ES+ 375.4257 (M+1)

$^1$H NMR: δ (DMSO-d6) 10.6(br s, 1H), 7.60–7.56(m, 2H), 7.32(dd, 1H), 7.12–7.09(m, 2H), 6.86–6.83(m, 2H), 6.49(d, 1H), 3.55–3.49(m, 3H), 2.79–2.71(m, 2H), 2.13–1.91(m, 4H), 1.56–1.46(m, 2H).

MP: 125° C.

Example 104

2-{[1-(3,4-Dichlorobenzyl)-4-piperidinyl]amino}-N-(3-methoxyphenyl)acetamide, dihydrochloride Salt

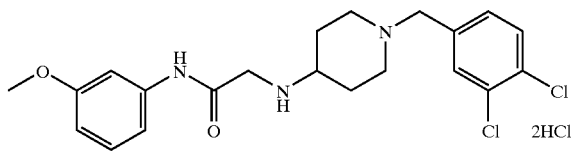

2-Chloro-N-(3-methoxyphenyl)-acetamide (0.241 g) was added to a stirred solution of the product of Example 1 step (ii) (dihydrochloride salt) (0.4 g), triethylamine (0.608 g) in 1-methyl-2-pyrrolidinone (5 ml). The reaction mixture was heated at 80° C. for 6 h then partitioned between ethyl acetate and brine. The organic layer was washed with brine, dried and evaporated under reduced pressure. Purification was by chromatography eluting with chloroform/isohexane/triethylamine/methanol 30:15:3:0.5. The resulting product was converted to the hydrochloride salt using ethereal hydrogenchloride. Yield 0.135 g.

TOF MS ES+ 422.1406 (M+1)

$^1$H NMR: δ (DMSO-d6) 11.21(br s, 1H), 10.82(s, 1H), 9.53(br s, 2H), 7.95(s, 1H), 7.75(d, 1H), 7.60(d, 1H), 7.31–7.23(m, 2H), 7.15(d, 1H), 6.70(dd, 1H), 4.28(br s, 2H), 3.97(br, H), 3.73(s, 3H), 2.96(br, 2H), 2.28–2.05(m, 4H).

MP: 274–6° C.

Example 105

N-[1-(3,4-Dichlorobenzyl)-4-piperidinyl]-N'-(3,4-dichlorophenyl)urea

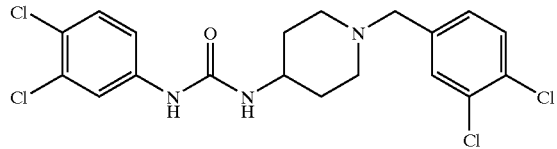

3,4-Dichlorophenyl isocyanate (0.081 g) was added to a stirred solution of the product from Example 1 step (ii) (0.13 g), diisopropylethylamine (0.2 g) in dichloromethane (4 ml). The reaction mixture was stirred for 20 h and the solvent removed under reduced pressure. Purification was by chromatography eluting with 5% methanol/dichloromethane. Yield 0.09 g as a solid.

TOF MS ES+ 446.0360 (M+1)

$^1$H NMR: δ (DMSO-d6) 8.65(s, 1H), 7.82(d, 1H), 7.59(d, 1H), 7.54(s, 1H), 7.31(d, 1H), 7.22(dd, 1H), 6.26(d, 1H), 3.45(br s, 3H), 2.67(m, 2H), 2.11(m, 2H), 1.81(m, 2H), 1.40(m, 2H).

MP: 189–190° C.

Example 106

N-[1-(3,4-Dichlorobenzyyl)-4-piperidinyl]-N'-(3-methoxyphenyl)urea

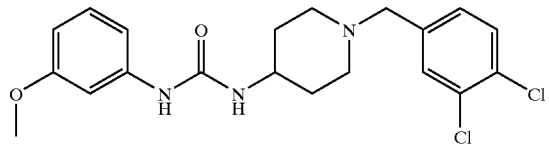

3-Methoxyphenyl isocyanate (0.064 g) was added to a stirred solution of the product from Example 1 step (ii) (0.13 g), diisopropylethylamine (0.2 g) in dichloromethane (4 ml). The reaction mixture was stirred for 20 h and the solvent removed under reduced pressure. Purification was by chromatography eluting with 5% methanol/dichloromethane. Yield 0.09 g as a solid.

MS: APCI(+ve) 408/10 (M+1)

$^1$H NMR: δ (DMSO-d6) 8.32(s, 1H), 7.59(d, 1H), 7.55(d, 1H), 7.31(dd, 1H), 7.13(m, 1H), 7.09(d, 1H), 6.83(dd,1H), 6.47(dd, 1H), 6.09(d, 1H), 3.69(s, 3H), 3.46(m, 3H), 2.66(m, 2H), 2.13(m, 2H), 1.81(m, 2H), 1.42(m, 2H).

MP: 178°–9° C.

Example 107

N-[1-(3,4-Dichlorobenzyl)-4-piperidinyl]-N-(4-methoxybenzyl)amine, dihydrochloride Salt

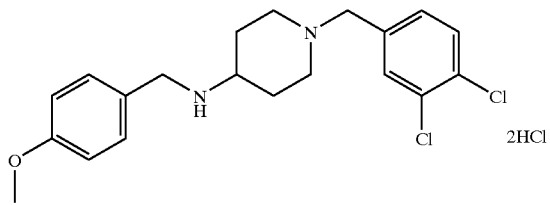

The title compound was prepared from the product of Example 1 step (ii) (0.185 g) and 4-methoxybenzaldehyd3 (0.49 ul) using the method of Example 1 step (i). Yield 0.84 g as a solid.

MS: APCI(+ve) 379/81 (M+1)

$^1$H NMR: δ (DMSO-d6) 11.33(br s, 1H), 9.56(br s, 2H), 7.96 (s, 1H), 7.74(d, 1H), 7.61(d, 1H), 7.52(d, 1H), 6.97(d, 1H), 4.27(s, 2H), 4.07(s,2H), 3.77(s, 3H), 3.39–2.94(m, 5H), 2.32–2.28(m, 2H), 2.15–2.07(m, 2H).

MP: >250° C.

The following table lists Examples 108–348 which are of compounds of formula (I) all of which accord to formula (Ib).

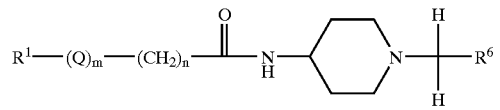

(Ib)

| Example | R¹ | (Q)ₘ | n | R⁶ |
|---|---|---|---|---|
| 108 | phenyl | m = 0 | 2 | 3,4-Cl$_2$—C$_6$H$_3$ |
| 109 | 4-Br—C$_6$H$_4$ | m = 0 | 1 | 3,4-Cl$_2$—C$_6$H$_3$ |
| 110 | 4-NH$_2$—C$_6$H$_4$ | m = 0 | 1 | 3,4-Cl$_2$—C$_6$H$_3$ |
| 111 | 2-Br—C$_6$H$_4$ | m = 0 | 1 | 3,4-Cl$_2$—C$_6$H$_3$ |
| 112 | 4-F—C$_6$H$_4$ | m = 0 | 1 | 3,4-Cl$_2$—C$_6$H$_3$ |
| 113 | 3-CH$_3$—C$_6$H$_4$ | m = 0 | 1 | 3,4-Cl$_2$—C$_6$H$_3$ |
| 114 | 2-CH$_3$—C$_6$H$_4$ | m = 0 | 1 | 3,4-Cl$_2$—C$_6$H$_3$ |
| 115 | 3-Cl-4-OH—C$_6$H$_3$ | m = 0 | 1 | 3,4-Cl$_2$—C$_6$H$_3$ |
| 116 | 2-NO$_2$—C$_6$H$_4$ | m = 0 | 1 | 3,4-Cl$_2$—C$_6$H$_3$ |
| 117 | 2-Cl—C$_6$H$_4$ | m = 0 | 1 | 3,4-Cl$_2$—C$_6$H$_3$ |
| 118 | 4-Cl—C$_6$H$_4$ | m = 0 | 1 | 3,4-Cl$_2$—C$_6$H$_3$ |
| 119 | 3,4-(OH)$_2$—C$_6$H$_3$ | m = 0 | 2 | 3,4-Cl$_2$—C$_6$H$_3$ |
| 120 | 4-NO$_2$—C$_6$H$_4$ | m = 0 | 1 | 3,4-Cl$_2$—C$_6$H$_3$ |
| 121 | phenyl | m = 0 | 4 | 3,4-Cl$_2$—C$_6$H$_3$ |
| 122 | 3,4-(OCH$_3$)$_2$—C$_6$H$_3$ | m = 0 | 1 | 3,4-Cl$_2$—C$_6$H$_3$ |
| 123 | 3-F-4-OH—C$_6$H$_3$ | m = 0 | 1 | 3,4-Cl$_2$—C$_6$H$_3$ |
| 124 | 3,4-methylenedioxyphenyl | m = 0 | 1 | 3,4-Cl$_2$—C$_6$H$_3$ |
| 125 | 4-OH—C$_6$H$_4$ | m = 0 | 2 | 3,4-Cl$_2$—C$_6$H$_3$ |
| 126 | 4-OH—C$_6$H$_4$ | m = 0 | 1 | 3,4-Cl$_2$—C$_6$H$_3$ |
| 127 | 4-phenyl-phenyl | m = 0 | 1 | 3,4-Cl$_2$—C$_6$H$_3$ |
| 128 | 3,4-Cl$_2$—C$_6$H$_3$ | m = 0 | 1 | 3,4-Cl$_2$—C$_6$H$_3$ |
| 129 | 3-OH—C$_6$H$_4$ | m = 0 | 2 | 3,4-Cl$_2$—C$_6$H$_3$ |
| 130 | 4-CH$_3$—C$_6$H$_4$ | m = 0 | 2 | 3,4-Cl$_2$—C$_6$H$_3$ |
| 131 | 4-NO$_2$—C$_6$H$_4$ | m = 0 | 3 | 3,4-Cl$_2$—C$_6$H$_3$ |
| 132 | 3,4-(OCH$_3$)$_2$—C$_6$H$_3$ | m = 0 | 2 | 3,4-Cl$_2$—C$_6$H$_3$ |
| 133 | C$_6$F$_5$ | m = 0 | 2 | 3,4-Cl$_2$—C$_6$H$_3$ |
| 134 | 4-CH$_3$—C$_6$H$_4$ | m = 0 | 1 | 3,4-Cl$_2$—C$_6$H$_3$ |
| 135 | 4-OCF$_3$—C$_6$H$_4$ | m = 0 | 1 | 3,4-Cl$_2$—C$_6$H$_3$ |
| 136 | 3,4-(OCH$_3$)$_2$—C$_6$H$_3$ | m = 0 | 3 | 3,4-Cl$_2$—C$_6$H$_3$ |
| 137 | 4-OCH$_3$—C$_6$H$_4$ | m = 0 | 1 | 3,4-Cl$_2$—C$_6$H$_3$ |
| 138 | 4-N(CH$_3$)$_2$—C$_6$H$_4$ | m = 0 | 1 | 3,4-Cl$_2$—C$_6$H$_3$ |
| 139 | 4-OCH$_3$—C$_6$H$_4$ | m = 0 | 2 | 3,4-Cl$_2$—C$_6$H$_3$ |
| 140 | 3,4,5-(OCH$_3$)$_3$—C$_6$H$_2$ | m = 0 | 1 | 3,4-Cl$_2$—C$_6$H$_3$ |
| 141 | 3,4-methylenedioxyphenyl | m = 0 | 2 | 3,4-Cl$_2$—C$_6$H$_3$ |
| 142 | 3-NH$_2$—C$_6$H$_4$ | m = 0 | 1 | 3,4-Cl$_2$—C$_6$H$_3$ |
| 143 | naphth-1-yl | m = 0 | 1 | 3,4-Cl$_2$—C$_6$H$_3$ |
| 144 | 3-OCH$_3$-4-OH—C$_6$H$_3$ | m = 0 | 1 | 3,4-Cl$_2$—C$_6$H$_3$ |
| 145 | 3-(6-Br-1-(prop-2-en-1-yl)-naphth-2-yloxymethyl)phenyl | m = 0 | 1 | 3,4-Cl$_2$—C$_6$H$_3$ |
| 146 | 4-(4-NO$_2$—C$_6$H$_4$—CH$_2$O)—C$_6$H$_4$ | m = 0 | 1 | 3,4-Cl$_2$—C$_6$H$_3$ |
| 147 | 3-F-4-CH$_3$O—C$_6$H$_3$ | m = 0 | 1 | 3,4-Cl$_2$—C$_6$H$_3$ |
| 148 | 3-CH$_3$—C$_6$H$_4$ | m = 0 | 4 | 3,4-Cl$_2$—C$_6$H$_3$ |
| 149 | 3-OH—C$_6$H$_4$ | m = 0 | 1 | 3,4-Cl$_2$—C$_6$H$_3$ |
| 150 | 4-(C$_6$H$_5$—CH$_2$O)—C$_6$H$_4$ | m = 0 | 1 | 3,4-Cl$_2$—C$_6$H$_3$ |
| 151 | 4-(3-NO$_2$—C$_6$H$_4$)—C$_6$H$_4$ | m = 0 | 1 | 3,4-Cl$_2$—C$_6$H$_3$ |
| 152 | 2,5-(CH$_3$)$_2$—C$_6$H$_3$ | m = 0 | 1 | 3,4-Cl$_2$—C$_6$H$_3$ |
| 153 | 4-I—C$_6$H$_4$ | m = 0 | 1 | 3,4-Cl$_2$—C$_6$H$_3$ |
| 154 | 3-Br—C$_6$H$_4$ | m = 0 | 1 | 3,4-Cl$_2$—C$_6$H$_3$ |
| 155 | 2-CH$_3$-3-NO$_2$—C$_6$H$_3$ | m = 0 | 1 | 3,4-Cl$_2$—C$_6$H$_3$ |
| 156 | 3-OH-4-OCH$_3$—C$_6$H$_3$ | m = 0 | 1 | 3,4-Cl$_2$—C$_6$H$_3$ |
| 157 | 3-F—C$_6$H$_4$ | m = 0 | 1 | 3,4-Cl$_2$—C$_6$H$_3$ |
| 158 | 2-F—C$_6$H$_4$ | m = 0 | 1 | 3,4-Cl$_2$—C$_6$H$_3$ |
| 159 | 3,5-(OCH$_3$)$_2$—C$_6$H$_3$ | m = 0 | 1 | 3,4-Cl$_2$—C$_6$H$_3$ |
| 160 | 3-Cl—C$_6$H$_4$ | m = 0 | 1 | 3,4-Cl$_2$—C$_6$H$_3$ |
| 161 | phenyl | m = 0 | 1 | 3,4-Cl$_2$—C$_6$H$_3$ |
| 162 | 3,5-(CH$_3$)$_2$—C$_6$H$_3$ | m = 0 | 1 | 3,4-Cl$_2$—C$_6$H$_3$ |
| 163 | 3-OCH$_3$—C$_6$H$_4$ | m = 0 | 2 | 3,4-Cl$_2$—C$_6$H$_3$ |
| 164 | 2,4-F$_2$—C$_6$H$_3$ | m = 0 | 1 | 3,4-Cl$_2$—C$_6$H$_3$ |
| 165 | 2-OCH$_3$—C$_6$H$_4$ | m = 0 | 1 | 3,4-Cl$_2$—C$_6$H$_3$ |
| 166 | 3,4-F$_2$—C$_6$H$_3$ | m = 0 | 1 | 3,4-Cl$_2$—C$_6$H$_3$ |
| 167 | 3,5-F$_2$—C$_6$H$_3$ | m = 0 | 1 | 3,4-Cl$_2$—C$_6$H$_3$ |
| 168 | Pyridin-3-yl | m = 0 | 1 | 3,4-Cl$_2$—C$_6$H$_3$ |
| 169 | Pyridin-2-yl | m = 0 | 1 | 3,4-Cl$_2$—C$_6$H$_3$ |
| 170 | 5-Br-pyridin-3-yl | m = 0 | 1 | 3,4-Cl$_2$—C$_6$H$_3$ |
| 171 | 2,4-(OCH$_3$)$_2$—C$_6$H$_3$ | m = 0 | 1 | 3,4-Cl$_2$—C$_6$H$_3$ |
| 172 | 4-(benzyloxy)phenyl | m = 0 | 1 | 3,4-Cl$_2$—C$_6$H$_3$ |
| 173 | 3-(benzyloxy)phenyl | m = 0 | 1 | 3,4-Cl$_2$—C$_6$H$_3$ |

-continued (Ib)

R¹—(Q)ₘ—(CH₂)ₙ—C(=O)—NH—[piperidine]—N—CH₂—R⁶

| Example | R¹ | (Q)ₘ | n | R⁶ |
|---|---|---|---|---|
| 174 | 2-methyl-naphth-1-yl | m = 0 | 1 | 3,4-Cl₂—C₆H₃ |
| 175 | 2-CH₃CH₂O—C₆H₄ | m = 0 | 1 | 3,4-Cl₂—C₆H₃ |
| 176 | 3,4-(OCH₃)₂—C₆H₃ | m = 0 | 1 | 3,4-Cl₂—C₆H₃ |
| 177 | 4-CH₃(CH₂)₃O—C₆H₄ | m = 0 | 1 | 3,4-Cl₂—C₆H₃ |
| 178 | Indol-1-yl | m = 0 | 1 | 3,4-Cl₂—C₆H₃ |
| 179 | 2-NO₂—C₆H₄ | m = 0 | 1 | 3,4-Cl₂—C₆H₃ |
| 180 | Thien-2-yl | m = 0 | 1 | 3,4-Cl₂—C₆H₃ |
| 181 | 3-Cl-4-OH—C₆H₃ | m = 0 | 1 | 3,4-Cl₂—C₆H₃ |
| 182 | 2,4-Cl₂—C₆H₃ | m = 0 | 1 | 3,4-Cl₂—C₆H₃ |
| 183 | 2,6-Cl₂—C₆H₃ | m = 0 | 1 | 3,4-Cl₂—C₆H₃ |
| 184 | 2-Br—C₆H₄ | m = 0 | 1 | 3,4-Cl₂—C₆H₃ |
| 185 | 3,4-Cl₂—C₆H₃ | m = 0 | 1 | 3,4-Cl₂—C₆H₃ |
| 186 | 3-Br—C₆H₄ | m = 0 | 1 | 3,4-Cl₂—C₆H₃ |
| 187 | 3,5-F₂—C₆H₃ | m = 0 | 1 | 3,4-Cl₂—C₆H₃ |
| 188 | 3-NH₂—C₆H₄ | m = 0 | 1 | 3,4-Cl₂—C₆H₃ |
| 189 | 2-(ClCH₂C(O)NH)-thiazol-4-yl | m = 0 | 1 | 3,4-Cl₂—C₆H₃ |
| 190 | 3-Cl—C₆H₄ | m = 0 | 1 | 3,4-Cl₂—C₆H₃ |
| 191 | 2,5-(OCH₃)₂—C₆H₃ | m = 0 | 1 | 3,4-Cl₂—C₆H₃ |
| 192 | 4-OH—C₆H₄ | m = 0 | 1 | 3,4-Cl₂—C₆H₃ |
| 193 | Indol-3-yl | m = 0 | 1 | 3,4-Cl₂—C₆H₃ |
| 194 | 5-OCH₃-indol-3-yl | m = 0 | 1 | 3,4-Cl₂—C₆H₃ |
| 195 | Naphth-2-yl | m = 0 | 1 | 3,4-Cl₂—C₆H₃ |
| 196 | 4-CH₃—C₆H₄ | m = 0 | 1 | 3,4-Cl₂—C₆H₃ |
| 197 | 3,4,5-(OCH₃)₃—C₆H₂ | m = 0 | 1 | 3,4-Cl₂—C₆H₃ |
| 198 | 4-CH₃(CH₂)₃O—C₆H₄ | m = 0 | 1 | 3,4-Cl₂—C₆H₃ |
| 199 | 4-S(O)₂CH₃—C₆H₄ | m = 0 | 1 | 3,4-Cl₂—C₆H₃ |
| 200 | 2,4,6-(CH₃)₃—C₆H₂ | m = 0 | 1 | 3,4-Cl₂—C₆H₃ |
| 201 | 4-F—C₆H₄ | | | |
| 202 | 2-(pyrazin-2-yl)-thiazol-4-yl | m = 0 | 1 | 3,4-Cl₂—C₆H₃ |
| 203 | 2-CH₃-5-(CH₃)₂CH-indol-3-yl | m = 0 | 1 | 3,4-Cl₂—C₆H₃ |
| 204 | 5-(pyrrolidin-1-yl)-tetrazol-2-yl | m = 0 | 1 | 3,4-Cl₂—C₆H₃ |
| 205 | 5-(4-CH₃-phenyl)-tetrazol-2-yl | m = 0 | 1 | 3,4-Cl₂—C₆H₃ |
| 206 | 3,5-F₂—C₆H₃ | m = 0 | 1 | 3,4-Cl₂—C₆H₃ |
| 207 | 3-OCH₃—C₆H₄ | m = 0 | 1 | 3,4-Cl₂—C₆H₃ |
| 208 | 5-Cl-benzo[b]thiophen-3-yl | m = 0 | 1 | 3,4-Cl₂—C₆H₃ |
| 209 | 3,4-Cl₂—C₆H₃ | m = 0 | 1 | 3,4-Cl₂—C₆H₃ |
| 210 | 2-phenyl-5-methyl-thiazol-4-yl | m = 0 | 1 | 3,4-Cl₂—C₆H₃ |
| 211 | 4-OCF₃—C₆H₄ | m = 0 | 1 | 3,4-Cl₂—C₆H₃ |
| 212 | 3-methyl-5-Cl-benzo[b]thiophen-2-yl | m = 0 | 1 | 3,4-Cl₂—C₆H₃ |
| 213 | 3-methyl-benzo[b]thiophen-2-yl | m = 0 | 1 | 3,4-Cl₂—C₆H₃ |
| 214 | 2-NO₂—C₆H₄ | m = 0 | 1 | 3,4-Cl₂—C₆H₃ |
| 215 | 3-NO₂-1,2,4-triazol-1-yl | m = 0 | 1 | 3,4-Cl₂—C₆H₃ |
| 216 | 3,4-(NO₂)₂-5-CH₃-pyrazol-1-yl | m = 0 | 1 | 3,4-Cl₂—C₆H₃ |
| 217 | 4-(CH₃)₂CH(CH₂)₂O—C₆H₄ | m = 0 | 1 | 3,4-Cl₂—C₆H₃ |
| 218 | 2,3-(CH₃)₂-indol-5-yl | m = 0 | 1 | 3,4-Cl₂—C₆H₃ |
| 219 | 3,5-(CH₃)₂-4-Cl-pyrazol-1-yl | m = 0 | 1 | 3,4-Cl₂—C₆H₃ |
| 220 | 3,5-(CH₃)₂-4-NO₂-pyrazol-1-yl | m = 0 | 1 | 3,4-Cl₂—C₆H₃ |
| 221 | 2,4-(NO₂)₂-imidazol-1-yl | m = 0 | 1 | 3,4-Cl₂—C₆H₃ |
| 222 | 4-NO₂-imidazol-1-yl | m = 0 | 1 | 3,4-Cl₂—C₆H₃ |
| 223 | 3,5-(CH₃)₂-pyrazol-1-yl | m = 0 | 1 | 3,4-Cl₂—C₆H₃ |
| 224 | 4-CH₃(CH₂)₅—C₆H₄ | m = 0 | 1 | 3,4-Cl₂—C₆H₃ |
| 225 | 2-CN—C₆H₄ | m = 0 | 1 | 3,4-Cl₂—C₆H₃ |
| 226 | 4-Cl—C₆H₄ | O | 1 | 4-Cl—C₆H₄ |
| 227 | 4-Cl—C₆H₄ | O | 1 | 2-Br—C₆H₄ |
| 228 | 4-Cl—C₆H₄ | O | 1 | 3-(CO₂CH₃)-4-Br—C₆H₄ |
| 229 | 4-Cl—C₆H₄ | O | 1 | 4-NO₂—C₆H₄ |
| 230 | 4-Cl—C₆H₄ | O | 1 | 3-benzoyl-phenyl |

-continued $$R^1-(Q)_m-(CH_2)_n-\underset{\underset{H}{|}}{C(=O)}-N-\text{piperidine}-N-\underset{\underset{H}{|}}{\overset{H}{|}}C-R^6$$ (Ib)

| Example | R¹ | (Q)ₘ | n | R⁶ |
|---|---|---|---|---|
| 231 | 4-Cl—C₆H₄ | O | 1 | 5-OCH₃-benzimidazol-2-yl |
| 232 | 4-Cl—C₆H₄ | O | 1 | 4-Br—C₆H₄ |
| 233 | 4-Cl—C₆H₄ | O | 1 | 4-(1,2,3-thiadiazol-4-yl)-phenyl |
| 234 | 4-Cl—C₆H₄ | O | 1 | 4-CH₃—C₆H₄ |
| 235 | 4-Cl—C₆H₄ | O | 1 | 4-(2,6-Cl₂—C₆H₃)CH₂S(O)₂—C₆H₄ |
| 236 | 4-Cl—C₆H₄ | O | 1 | 3,5-Br₂—C₆H₃ |
| 237 | 4-Cl—C₆H₄ | O | 1 | Indan-5-yl |
| 238 | 4-Cl—C₆H₄ | O | 1 | 2-F-3-Cl—C₆H₃ |
| 239 | 4-Cl—C₆H₄ | O | 1 | benzofurazan-5-yl |
| 240 | 4-Cl—C₆H₄ | O | 1 | 7-Cl-quinolin-2-yl |
| 241 | 4-F—C₆H₄ | m = 0 | 1 | 2,5-Cl₂—C₆H₃ |
| 242 | 4-F—C₆H₄ | m = 0 | 1 | 2,3-Cl₂—C₆H₃ |
| 243 | 4-F—C₆H₄ | m = 0 | 1 | 4-F—C₆H₄ |
| 244 | 4-F—C₆H₄ | m = 0 | 1 | 3-CO₂CH₃-4-Br—C₆H₃ |
| 245 | 4-F—C₆H₄ | m = 0 | 1 | 4-NO₂—C₆H₄ |
| 246 | 4-F—C₆H₄ | m = 0 | 1 | 3-benzoyl-phenyl |
| 247 | 4-F—C₆H₄ | m = 0 | 1 | 4-CH₃-naphth-1-yl |
| 248 | 4-F—C₆H₄ | m = 0 | 1 | 3,4-methylene-dioxyphenyl |
| 249 | 4-F—C₆H₄ | m = 0 | 1 | 5-OCH₃-benzimidazol-2-yl |
| 250 | 4-F—C₆H₄ | m = 0 | 1 | 3-NO₂-4-CH₃—C₆H₃ |
| 251 | 4-F—C₆H₄ | m = 0 | 1 | 3,4-(CH₃)₂—C₆H₃ |
| 252 | 4-F—C₆H₄ | m = 0 | 1 | 3-CH₃-4-OCH₃—C₆H₃ |
| 253 | 4-F—C₆H₄ | m = 0 | 1 | 4-(2-C(O)NH₂—C₆H₄)—C₆H₄ |
| 254 | 4-F—C₆H₄ | m = 0 | 1 | 4-Br—C₆H₄ |
| 255 | 4-F—C₆H₄ | m = 0 | 1 | 4-(2,6-Cl₂—C₆H₄)CH₂S(O)₂—C₆H₄ |
| 256 | 3-(pyridin-2-yl)-1,2,4-oxadiazol-5-yl | m = 0 | 2 | 4-Cl—C₆H₄ |
| 257 | 3-(pyridin-2-yl)-1,2,4-oxadiazol-5-yl | m = 0 | 2 | 3-Cl-4-OCH₃—C₆H₃ |
| 258 | 3-(pyridin-2-yl)-1,2,4-oxadiazol-5-yl | m = 0 | 2 | 2,3-Cl₂—C₆H₃ |
| 259 | 3-(pyridin-2-yl)-1,2,4-oxadiazol-5-yl | m = 0 | 2 | 4-F—C₆H₄ |
| 260 | 3-(pyridin-2-yl)-1,2,4-oxadiazol-5-yl | m = 0 | 2 | 3-CF₃—C₆H₄ |
| 261 | 3-(pyridin-2-yl)-1,2,4-oxadiazol-5-yl | m = 0 | 2 | 4-NO₂—C₆H₄ |
| 262 | 3-(pyridin-2-yl)-1,2,4-oxadiazol-5-yl | m = 0 | 2 | 3-benzoyl-phenyl |
| 263 | 3-(pyridin-2-yl)-1,2,4-oxadiazol-5-yl | m = 0 | 2 | 3,4-methylene-dioxyphenyl |
| 264 | 3-(pyridin-2-yl)-1,2,4-oxadiazol-5-yl | m = 0 | 2 | 3,5-(CH₃)₂—C₆H₃ |
| 265 | 3-(pyridin-2-yl)-1,2,4-oxadiazol-5-yl | m = 0 | 2 | 3-NO₂-4-CH₃—C₆H₃ |
| 266 | 3-(pyridin-2-yl)-1,2,4-oxadiazol-5-yl | m = 0 | 2 | 3,4-(CH₃)₂—C₆H₃ |
| 267 | 3-(pyridin-2-yl)-1,2,4-oxadiazol-5-yl | m = 0 | 2 | 3-CH₃—C₆H₄ |
| 268 | 3-(pyridin-2-yl)-1,2,4-oxadiazol-5-yl | m = 0 | 2 | 3-CH₃-4-OCH₃—C₆H₄ |
| 269 | 3-(pyridin-2-yl)-1,2,4-oxadiazol-5-yl | m = 0 | 2 | 4-Br—C₆H₄ |
| 270 | 3-(pyridin-2-yl)-1,2,4-oxadiazol-5-yl | m = 0 | 2 | Indan-5-yl |
| 271 | 3-(pyridin-2-yl)-1,2,4-oxadiazol-5-yl | m = 0 | 2 | 4-CF₃—C₆H₄ |
| 272 | 3-(pyridin-2-yl)-1,2,4-oxadiazol-5-yl | m = 0 | 2 | Naphth-2-yl |
| 273 | 3-(pyridin-2-yl)-1,2,4-oxadiazol-5-yl | m = 0 | 2 | 4-CH₃—C₆H₄ |
| 274 | 3-(pyridin-2-yl)-1,2,4-oxadiazol-5-yl | m = 0 | 2 | benzofurazan-5-yl |
| 275 | 3-(pyridin-2-yl)-1,2,4-oxadiazol-5-yl | m = 0 | 2 | 3,4-F₂—C₆H₃ |
| 276 | 3-(pyridin-2-yl)-1,2,4-oxadiazol-5-yl | m = 0 | 2 | 4-Cl-quinolin-2-yl |
| 277 | 3-(pyridin-2-yl)-1,2,4-oxadiazol-5-yl | m = 0 | 2 | 3-Cl—C₆H₄ |

-continued $$R^1-(Q)_m-(CH_2)_n-\underset{\underset{H}{N}}{\overset{O}{C}}-\underset{}{\overset{}{\underset{}{\text{piperidine}}}}-N-\underset{H}{\overset{H}{C}}-R^6 \quad \text{(Ib)}$$

| Example | R¹ | (Q)ₘ | n | R⁶ |
|---|---|---|---|---|
| 278 | 3-(pyridin-2-yl)-1,2,4-oxadiazol-5-yl | m = 0 | 2 | 4-CF₃—C₆H₄ |
| 279 | 3-(pyridin-2-yl)-1,2,4-oxadiazol-5-yl | m = 0 | 2 | 4-CH₃—C₆H₄ |
| 280 | 4-OCH₃—C₆H₄ | O | 1 | 3,4-Cl₂—C₆H₃ |
| 281 | 4-Cl—C₆H₄ | O | 1 | 3,4-Cl₂—C₆H₃ |
| 282 | 4-NO₂—C₆H₄ | O | 1 | 3,4-Cl₂—C₆H₃ |
| 283 | 4-NHC(O)CH₃—C₆H₄ | O | 1 | 3,4-Cl₂—C₆H₃ |
| 284 | 4-O(CH₂)₂CH₃—C₆H₄ | O | 1 | 3,4-Cl₂—C₆H₃ |
| 285 | 3-CO₂CH₂CH₃—C₆H₄ | O | 1 | 3,4-Cl₂—C₆H₃ |
| 286 | 2-C(CH₃)₃—C₆H₄ | O | 1 | 3,4-Cl₂—C₆H₃ |
| 287 | 2-NHC(O)CH₃—C₆H₄ | O | 1 | 3,4-Cl₂—C₆H₃ |
| 288 | 3,5-(OCH₃)₂—C₆H₃ | O | 1 | 3,4-Cl₂—C₆H₃ |
| 289 | 2-OCH₃-5-NO₂—C₆H₃ | O | 1 | 3,4-Cl₂—C₆H₃ |
| 290 | 4-CN—C₆H₄ | O | 1 | 3,4-Cl₂—C₆H₃ |
| 291 | 2-Cl-5-CF₃—C₆H₃ | O | 1 | 3,4-Cl₂—C₆H₃ |
| 292 | 2-NO₂-5-CH₃—C₆H₃ | O | 1 | 3,4-Cl₂—C₆H₃ |
| 293 | 3-Cl-5-OCH₃—C₆H₃ | O | 1 | 3,4-Cl₂—C₆H₃ |
| 294 | 3-NO₂—C₆H₄ | O | 1 | 3,4-Cl₂—C₆H₃ |
| 295 | 3-Br—C₆H₄ | O | 1 | 3,4-Cl₂—C₆H₃ |
| 296 | 4-I—C₆H₄ | O | 1 | 3,4-Cl₂—C₆H₃ |
| 297 | 3,5-F₂—C₆H₃ | O | 1 | 3,4-Cl₂—C₆H₃ |
| 298 | 4,6-(NH₂)₂-pyrimidin-2-yl | S | 1 | 3,4-F₂—C₆H₃ |
| 299 | Benzimidazol-2-yl | S | 1 | 3,4-F₂—C₆H₃ |
| 300 | Thiazol-2-yl | S | 1 | 3,4-F₂—C₆H₃ |
| 301 | 2-methyl-4-oxo-3H-quinazolin-yl | S | 1 | 3,4-F₂—C₆H₃ |
| 302 | 5-NO₂-benzimidazol-2-yl | S | 1 | 3,4-F₂—C₆H₃ |
| 303 | Pyridin-2-yl | S | 1 | 3,4-F₂—C₆H₃ |
| 304 | 7H-purin-6-yl | S | 1 | 3,4-F₂—C₆H₃ |
| 305 | 1H-1,2,4-triazol-3-yl | S | 1 | 3,4-F₂—C₆H₃ |
| 306 | Pyrimidin-2-yl | S | 1 | 3,4-F₂—C₆H₃ |
| 307 | 1-phenyl-tetrazol-5-yl | S | 1 | 3,4-F₂—C₆H₃ |
| 308 | 4,6-(CH₃)₂-pyrimidin-2-yl | S | 1 | 3,4-F₂—C₆H₃ |
| 309 | 4-(thiophen-2-yl)-pyrimidin-2-yl | S | 1 | 3,4-F₂—C₆H₃ |
| 310 | 2-(cyclopropyl-CH₂S)-1,3,4-thiadiazol-5-yl | S | 1 | 3,4-F₂—C₆H₃ |
| 311 | 4-methyl-3-(thiophen-2-yl)-1,2,4-triazol-5-yl | S | 1 | 3,4-F₂—C₆H₃ |
| 312 | 3-CN-6-(CH₃C(O))-pyridin-2-yl | S | 1 | 3,4-F₂—C₆H₃ |
| 313 | 1H-pyrazolo[3,4-d]pyrimidin-4-yl | S | 1 | 3,4-F₂—C₆H₃ |
| 314 | 5-OCH₃-benzimidazol-2-yl | S | 1 | 3,4-F₂—C₆H₃ |
| 315 | 5-F-6-Cl-benzimidazol-2-yl | S | 1 | 3,4-F₂—C₆H₃ |
| 316 | 4,5-dihydrothiazol-2-yl | S | 1 | 3,4-F₂—C₆H₃ |
| 317 | 1H-5-phenyl-1,2,4-triazol-3-yl | S | 1 | 3,4-F₂—C₆H₃ |
| 318 | 2-(thiophen-2-yl)-1,3,4-oxadiazol-5-yl | S | 1 | 3,4-F₂—C₆H₃ |
| 319 | Quinoxalin-2-yl | S | 1 | 3,4-F₂—C₆H₃ |
| 320 | 2,5-Cl₂—C₆H₃ | S | 1 | 3,4-F₂—C₆H₃ |
| 321 | 2-(pyridin-2-yl)-1,3,4-oxadiazol-5-yl | S | 1 | 3,4-F₂—C₆H₃ |
| 322 | 7-CF₃-quinolin-4-yl | | | |

-continued $$R^1-(Q)_m-(CH_2)_n-C(=O)-NH-\text{piperidine}-N(H)-CH(H)-R^6 \quad (Ib)$$

| Example | R¹ | (Q)ₘ | n | R⁶ |
|---|---|---|---|---|
| 323 | 2-(pyridin-2-yl)-4-CH₃-pyrimidin-6-yl | S | 1 | 3,4-F₂—C₆H₃ |
| 324 | Naphth-1-yl | S | 1 | 3,4-F₂—C₆H₃ |
| 325 | 3,4-(OCH₃)₂—C₆H₃ | S | 1 | 3,4-F₂—C₆H₃ |
| 326 | 1,3,4-thiadiazol-2-yl | S | 1 | 3,4-F₂—C₆H₃ |
| 327 | 3-CF₃—C₆H₄ | S | 1 | 3,4-F₂—C₆H₃ |
| 328 | 2-methyl-imidazo-benzodioxine | S | 1 | 3,4-F₂—C₆H₃ |
| 329 | 3,4-Cl₂—C₆H₃ | S | 1 | 3,4-F₂—C₆H₃ |
| 330 | 3-CN-5-CH₃-pyridin-2-yl | S | 1 | 3,4-F₂—C₆H₃ |
| 331 | 4-phenyl-thiazol-2-yl | S | 1 | 3,4-F₂—C₆H₃ |
| 332 | methyl-imidazo[2,1-b]thiazole-carbaldehyde | S | 1 | 3,4-F₂—C₆H₃ |
| 333 | 2-CH₃-1,3,4-thiadiazol-5-yl | S | 1 | 3,4-F₂—C₆H₃ |
| 334 | dimethyl-triazolopyrimidine | S | 1 | 3,4-F₂—C₆H₃ |
| 335 | 2-methyl-purine | S | 1 | 3,4-F₂—C₆H₃ |
| 336 | 2-phenoxy-phenyl | S | 1 | 3,4-F₂—C₆H₃ |
| 337 | 2-OCH₃—C₆H₄ | S | 1 | 3,4-F₂—C₆H₃ |
| 338 | 2-CH₃-4-Cl—C₆H₃ | S | 1 | 3,4-F₂—C₆H₃ |
| 339 | 2-CH₃-6-Cl—C₆H₃ | S | 1 | 3,4-F₂—C₆H₃ |
| 340 | 2-(HC≡C—CH₂S)-1,3,4-thiadiazol-5-yl | S | 1 | 3,4-F₂—C₆H₃ |
| 341 | 2-CO₂CH₃—C₆H₄ | S | 1 | 3,4-F₂—C₆H₃ |
| 342 | 4-CN—C₆H₄ | O | 1 | 3,4-F₂—C₆H₃ |
| 343 | 4-((CH₃)₂NCH₂)—C₆H₄ | O | 1 | 3,4-F₂—C₆H₃ |
| 344 | 6-methyl-quinazoline-2,4-dione | O | 1 | 3,4-F₂—C₆H₃ |
| 345 | 3-CH₂OH—C₆H₄ | O | 1 | 3,4-F₂—C₆H₃ |
| 346 | 2-OCH₂CH₂OH—C₆H₄ | O | 1 | 3,4-F₂—C₆H₃ |
| 347 | 4-CH₃(CH₂)₂O—C₆H₄ | O | 1 | 3,4-F₂—C₆H₃ |
| 348 | 3-Cl-5-OCH₃—C₆H₃ | O | 1 | 3,4-F₂—C₆H₃ |

General Preparation of Examples 108–225

PyBroP® (bromo-tris-pyrrolidino-phosphonium hexafluorophosphate, 2 equivalents) was added to a solution of the product from Example 1 step (ii) (hydrochloride salt, 1 mg) the appropriate acid (2 equivalents) and triethylamine in 1-methyl-2-pyrrolidone (0.2 ml) and was left for 24 h. The reaction mixture was evaporated to dryness and the residue was dissolved in dimethylsulfoxide (0.3 ml).

General Preparation of Examples 225–240

Step i: tert-Butyl 4-{[(4-chlorophenoxy)acetyl]amino}-1-piperidinecarboxylate

Prepared following the method of Example 94 using (4-chlorophenoxy)acetic acid (0.50 g), 1,1-carbonyldiimidazole (0.50 g) and tert-butyl 4-amino-1-piperidinecarboxylate (0.46 g) to give the subtitle compound (0.54 g).

$^1$H NMR (399.978 MHz, CDCl$_3$) δ 1.34–1.40 (2H, m), 1.46 (9H, s), 1.90–1.95(2H, m), 2.86–2.88 (2H, m), 4.01–4.14 (3H, m), 4.45 (2H, s), 6.38–6.41 (1H, m), 6.84–6.87 (2H, m), 7.26–7.30 (2H, m).

Step ii: 2-(4-chlorophenoxy)-N-(4-piperidinyl)acetamide

Prepared following the method of Example 1 step (ii) using tert-butyl-4-{[(4-chlorophenoxy)acetyl]amino}-1-piperidinecarboxylate (0.52 g) to give the subtitle compound (0.35 g).

$^1$H NMR (399.978 MHz, CDCl$_3$) δ 1.32–1.45 (2H, m), 1.93–1.97 (2H, m), 2.68–2.77 (2H, m), 3.07–3.11 (2H, m), 3.91–4.04 (1H, m), 4.45 (2H, s), 6.38–6.40 (1H, m), 6.84–6.89 (2H, m), 7.26–7.31 (2H, m).

Step iii: Final product

A mixture of the product from step (ii) (1.07 mg), the appropriate alkyl halide (2 equivalents) and N,N-diisopropylethylamine (3 equivalents) in 1-methyl-2-pyrrolidinone (0.18 ml) was left at room temperature for 24 h. The mixture was evaporated to dryness and the residue was dissolved in dimethylsulfoxide (0.4 ml).

General Preparation of Examples 241–255

A mixture of 2-(4-fluorophenyl)-N-(4-piperidinyl)acetamide (WO97/36871; 0.94 mg), the appropriate alkyl halide (2 equivalents) and N,N-diisopropylethylamine (3 equivalents) in 1-methyl-2-pyrrolidinone (0.18 ml) was left at room temperature for 24 h. The mixture was evaporated to dryness and the residue was dissolved in dimethylsulfoxide (0.4 ml).

General Preparation of Examples 256–279

Step i: tert-Butyl 4-({3-[3-(2-pyridinyl)-1,2,4-oxadiazol-5-yl]propanoyl}amino)-1-piperidinecarboxylate 3-[3-(2-Pyridinyl)-1,2,4-oxadiazol-5-yl]propanoic acid (0.60 g) was dissolved in dichloromethane (10 ml). 1,1-Carbonyldiimidazole (0.33 g) was added followed by tert-butyl 4-amino-1-piperidinecarboxylate hydrochloride (0.5 g) and triethylamine (0.31 ml). After 2 hours water, brine and dichloromethane were added and the phases separated. The organic phase was dried, filtered and evaporated and the residue was purified by chromatography eluting with ethyl acetate:methanol (33:1) to give the subtitle compound (0.40 g).

$^1$H NMR (399.98 MHz, DMOS) δ 1.22–1.24 (2H, m), 1.39 (9H, s), 1.62–1.71 (2H, m), 2.66–2.71 (4H, m), 3.18–3.23 (2H, m), 3.65–3.83 (3H, m), 7.58–7.63 (1H), 8.01–8.04 (3H, m), 8.74–8.76(1H, m).

Step ii: N-(4-Piperidinyl)-3-[3-(2-pyridinyl)-1,2,4-oxadiazol-5-yl]propanamide tert-Butyl 4-({3-[3-(2-pyridinyl)-1,2,4-oxadiazol-5-yl]propanoyl}amino)-1-piperidinecarboxylate (0.40 g) was dissolved in dichloromethane (6 ml) and trifluoroacetic acid (3 ml) was added. After 2 hours water, 2N sodium hydroxide and dichloromethane were added and the phases were separated. The organic phase was dried, filtered and evaporated to give the subtitle compound (0.19 g).

$^1$H NMR (399.978 MHz, CDCl$_3$) δ 1.35–1.45 (2H, m), 1.86–1.97 (2H, m), 2.69–2.84 (4H, m), 3.09–3.13 (2H, m), 3.32–3.36 (2H, m), 3.86–3.95 (1H, m), 5.82–5.84 (1H, m), 7.42–7.45 (1H, m), 7.83–7.87 (1H, m), 8.10–8.12 (1H, m), 8.78–8.79 (1H, m).

Step iii: Final product

A mixture of the product from step (ii) (1.21 mg), the appropriate alkyl halide (2 equivalents) and N,N-diisopropylethylamine (3 equivalent) in 1-methyl-2-pyrrolidinone (0.18 ml) was left at room temperature for 24 h. The mixture was evaporated to dryness and the residue was dissolved in dimethylsulfoxide (0.4 ml).

General Preparation of Examples 280–296

Step i: 2-Chloro-N-[1-(3,4-dichlorobenyzl)-4-piperidinyl] acetamide

Prepared following the general preparation method of Examples 297–357 step (iii) using 1-(3,4-dichlorobenzyl)-4-piperidinamine hydrochloride (2.0 g), N,N-diisopropylethylamine (5.55 ml) and chloroacetyl chloride (0.55 ml) to give the subtitle compound (1.0 g).

$^1$H NMR (399.978 MHz, CDCl$_3$) δ 1.48–1.61 (2H, m), 1.91–1.94 (2H, m), 1.95–2.18 (2H, m), 2.77–2.80 (2H, m), 3.44 (2H, s), 3.78–3.87 (1H, m), 4.04 (2H, s), 7.13–7.16 (1H, m), 7.37–7.43 (2H, m).

Step ii: Final Product

A mixture of the product from step (i) (1.34 mg), the appropriate phenol (1.5 equivalents) and potassium tert-butoxide (1.4 equivalents) in 1-methyl-2-pyrrolidinone (0.13 ml) was left at room temperature for 24 hours. The mixture was evaporated to dryness and the residue was dissolved in dimethylsulfoxide (0.4 ml).

General Preparation of Examples 297–340

Step i: Carbamic acid, [1-[(3,4-difluorophenyl)methyl]-4-piperidinyl]-, 1,1-dimethylethyl ester Carbamic acid, 4-piperidinyl-, 1,1-dimethylethyl ester (6.95 g) was dissolved in N,N-dimethylformamide (70 ml). 3,4-Difluorobenzylbromide (4.55 ml) and potassium carbonate (16.0 g) were added. The mixture was heated to reflux for 16 hours, then allowed to cool to room temperature. Ammonium chloride solution was added and the mixture was extracted thrice with ethyl acetate. The organic phases were washed with water (twice) and brine, then dried, filtered and evaporated. The residue was triturated with ether:iso-hexane (1:1) to give the subtitle compound (8.13 g)

$^1$H NMR (399.978 MHz, CDCl$_3$) δ 1.36–1.43 (m, 2H), 1.44 (s, 9H), 1.91 (d, J=11.8 Hz, 2H), 2.08 (td, J=11.4, 2.7 Hz, 2H), 2.75 (d, J=11.3 Hz, 2H), 3.41 (s, 2H), 3.42–3.55 (m, 1H), 4.38–4.47 (m, 1H), 6.96–7.02 (m, 1H), 7.04–7.11 (m, 2H), 7.13–7.19 (m, 1H)

Step ii: 1-[(3,4-Difluorophenyl)methyl]-piperidin-4-ylamine dihydrochloride

Carbamic acid, [1-[(3,4-difluorophenyl)methyl]-4-piperidinyl]-, 1,1-dimethylethyl ester was suspended in 6N hydrochloric acid (100 ml). After 16 hours excess hydrochloric acid was evaporated and the residue azeotroped with toluene, dried and evaporated to give the subtitle compound (8.10 g).

$^1$H NMR (399.98 MHz, DMSO) δ 1.91–2.10 (2H, m), 2.31–2.47(2H, m), 2.86–3.20(2H,m), 3.54–3.66(3H,m), 4.75–4.83(2H,s), 7.26–7.61(3H,m).

Step iii: 2-Chloro-N-[1-[(3,4-difluorophenyl)methyl]-piperidin-4-yl]-acetamide

1-[(3,4-Difluorophenyl)methyl]-piperidin-4-ylamine dihydrochloride (3.18 g) was dissolved in tetrahydrofuran (40 ml). Diisopropylethlamine (6.84 g) and chloroacetyl chloride (1.33 g) were added. After 3 hours water, brine and ethyl acetate were added the phase were separated. The organic phase was dried, filtered and evaporated and the residue was purified by chromatography eluting with ethyl acetate to give the subtitle compound (0.728 g).

$^1$H NMR (CDCl$_3$) δ 1.46–1.59 (2H, m), 1.93 (2H, d), 2.14 (2H, td), 2.78 (2H, d), 3.43 (2H, s), 3.76–3.91 (1H, m), 4.04 (2H, s), 6.39–6.51 (1H, m), 6.98–7.02 (1H, m), 7.08 (1H, dd), 7.17 (1H, ddd).

Step iv: Final Product

The product from step (iii) (1.21 mg) was dissolved in dimethylsulfoxide (50 μl) and diisopropylethylamine (1.55 mg, 3 equivalents) was added as a solution in dimethylsulfoxide (50 μl). The appropriate thiol was added (1 equivalent) in dimethylsulfoxide (40 μl) and the reaction mixture was left at room temperature for 24 hours. The reaction mixture was evaporated to dryness and the residue was dissolved in dimethylsulfoxide (400 μl).

General Preparation of Examples 341–348

Prepared from the product of general preparation for Examples 297–340 step (iii) and the appropriate phenol following the method of Examples 280–296 step (ii).

Example 351

3-[3-(4-Bromo-1-methyl-1H-pyrazol-3-yl)-1,2,4-oxadiazol-5-yl]-N-[1-(3,4-dichlorobenzyl)-4-piperidinyl]propanamide

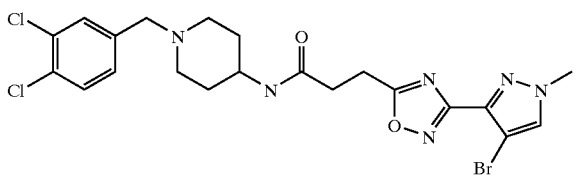

Step i: Methyl 4-{[1-(3,4-dichlorobenzyl)-4-piperidinyl]amino}-4-oxobutanoate

To a solution of 1-(3,4-dichlorobenzyl)-4-piperidinamine hydrochloride (3.50 g) in dichloromethane (100 ml) was added methyl 4-chloro-4-oxobutanoate (2.00 g) dropwise. Triethlamine (3.90 g) was added and the reaction stirred under nitrogen for 2 hours. Saturated sodium hydrogen carbonate solution was then added, with the solution being extracted three times with dichloromethane. The pooled organic phase was washed once with water, once with saturated brine and dried over anhydrous magnesium sulfate. After filtration the solvent was removed under reduced pressure to leave methyl 4-{[1-(3,4-dichlorobenzyl)-4-piperidinyl]amino}-4-oxobutanoate (3.00 g).

MS (+veES) 373 ((M+H)$^+$)

Step ii: Lithium 4-{[1-(3,4-dichlorobenzyl)-4-piperidinyl]amino}-4-oxobutanoate

To a solution of methyl 4-{[1-(3,4-dichlorobenzyl)-4-piperidinyl]amino}-4-oxobutanoate (3.72 g) in methanol (30 ml) was added lithium hydroxide (0.41 g) in water (10 ml) which was stirred under nitrogen for 48 hours. The solvent was removed under reduced pressure, the residue was triturated with ether and filtered to leave lithium 4-{[1-(3,4-dichlorobenzyl)-4-piperidinyl]amino}-4-oxobutanoate (3.50 g).

MS (+veES) 359 ((M+H)$^+$)

Step iii: 3-[3-(4-Bromo-1-methyl-1H-pyrazol-3-yl)-1,2,4-oxadiazol-5-yl]-N-[1-(3,4-dichlorobenzyl)-4-piperidinyl]propanamide To lithium 4-{[1-(3,4-dichlorobenzyl)-4-piperidinyl]amino}-4-oxobutanoate (0.292 g) in dichloromethane (6 ml) was added dimethylformamide (1.5 ml), 1-(3-dimethylaminopropyl)-3-ethylcarbodiimide hydrochloride (0.183 g), 1-hydroxybenzotriazole hydrate (0.130 g), 4-bromo-N'-hydroxy-1methyl-1H-pyrazole-3-carboximidamide (0.175 g) and triethylamine (0.161 g). Reaction was left to stir for 24 hours before removal of dichloromethane under reduced pressure. Pyridine (5 ml) was added and heated at reflux for 5 hours. Pyridine was removed under reduced pressure, followed by the addition of water. The solution was extracted three times with dichloromethane. The pooled organic phase was washed once with water, once with saturated brine and dried over magnesium sulfate. After filtration the product was azeotroped twice with toluene and was purified by reverse phase hplc (RPHPLC; 75%–5% 0.1% ammonium acetate/acetonitrile). Solvent was removed under reduced pressure to give the title compound (0.164 g).

MS (+veAPC) 543 ((M+H)$^+$)

$^1$H NMR (DMSO): δ 8.21–8.17 (1H,m); 7.95–7.76(1H, m); 7.60–7.54(1H,m); 7.35–7.25(1H,m); 4.35–4.21(1H,m); 3.93(2H,s); 3.44–3.35(2H,m); 3.19–3.14(3H,m); 2.73–2.64 (2H,m); 2.58(3H,s); 2.00–1.89(2H,m); 1.73–1.60(2H,m); 1.36–1.24(1H,m).

Example 352

N-[1-(3,4-Dichlorobenzyl)-4-piperidinyl]-3-[3-(2-pyrazinyl)-1,2,4-oxadiazol-5-yl]propanamide

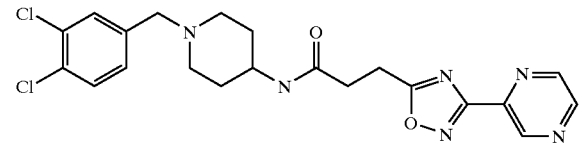

To lithium 4-{[1-(3,4-dichlorobenzyl)-4-piperidinyl]amino}-5-oxobutanoate (Example 351, step ii) (0.292 g) in dichloromethane (6 ml) was added N,N-dimethylformamide (1.5 ml), 1-(3-dimethylaminopropyl)-3-ethylcarbodiimide hydrochloride (0.183 g), 1-hydroxybenzotriazole hydrate (0.130 g), N'-hydroxy-2-pyrazinecarboximidamide (0.110 g) and triethylamine (0.161 g). The reaction mixture was left to stir for 24 hours before removal of dichloromethane under reduced pressure. Pyridine (5 ml) was added and heated at reflux for 5 hours. Pyridine was removed under reduced pressure followed by the addition of water. The solution was extracted three times with dichloromethane. The pooled organic phase was washed once with water, once with saturated brine and dried over magnesium sulfate. After filtration the product was azeotroped twice with toluene and was purified by RPHPLC (75%–5%, 0.1% ammonium acetate/acetonitrile). Solvent was removed under reduced pressure to give the title compound (0.067 g).

MS (+veAPC)461 ((M+H)$^+$)

$^1$H NMR (DMSO) δ 9.23 (1H,s); 8.81–8.45(2H,m), 7.96–7.94(1H,m); 7.58–7.56(1H,m); 7.53–7.52(1H,m); 7.29–7.26(1H,m), 3.55–3.48(1H,m); 3.43(2H,s); 3.24–3.20 (2H,m); 2.71–2.68(4H,m); 2.03–1.98(2H,m); 1.70–1.68(2H, m); 1.42–1.33(2H,m).

Example 353

N-[1-(3,4-Dichlorobenzyl)-4-piperidinyl]-3-{3-[2-thienylsulfonyl)methyl]-1,2,4-oxadiazol-5-yl}propanamide Hydrochloride

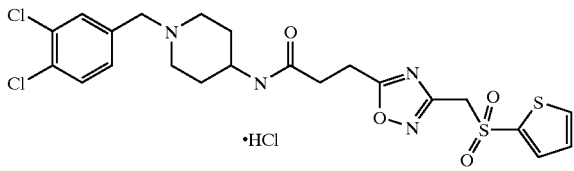

Step i: 3-{3-[(2-Thienylsulfonyl)methyl]-1,2,4-oxadiazol-5-yl}propionic acid (1Z)-N'-hydroxy-2-(2-thienylsulfonyl)ethanimidamide (0.250 g) with dihydro-2,5-furandione (0.114 g) in dimethylformamide (0.2 ml) was heated at 120° C. for 2 hours. The reaction was allowed to cool and triturated with diethyl ether and filtered to leave 3-{3-[(2-thienylsulfonyl)methyl]-1,2,4-oxadiazol-5-yl}propanoic acid (0.332 g).

MS (+veES) 303 ((M+H)$^+$)

Step ii: N-[1-(3,4-Dichlorobenzyl)-4-piperidinyl]-3-{3-[(2-thienylsulfonyl)methyl]-1,2,4-oxadiazol-5-yl}propanamide hydrochloride 3-{3-[(2-Thienylsulfonyl)methyl]-1,2,4-oxadiazol-5-yl}propanoic acid (0.332 g) in dichloromethane was stirred under nitrogen. Oxazolyl chloride (0.252 g) was added dropwise followed by the addition of one drop of dimethylformamide. After 30 minutes the solvent and oxalyl chloride was removed under reduced pressure followed by the addition of dichloromethane (10 ml), 1-(3,4-dichlorobenzyl)-4-piperidinamine hydrochloride (0.347 g), and triethylamine (0.202 g) and allowed to stir for 2 hours under nitrogen. Saturated sodium hydrogen carbonate was added to the reaction with the resulting solution being extracted three times with dichloromethane. The pooled organic phases were washed once with water, once with brine, dried over magnesium sulfate, filtered and the solvent removed under reduced pressure to leave a brown oil. This oil was purified by RPHPLC (75%–5%, 0.1% ammonium acetate/acetonitrile) followed by chromatography using 3% ethanol/dichloromethane. The solvent was removed under reduced pressure, followed by the addition of hydrogen chloride in diethyl ether, filtered and dried to leave N-[1-(3,4-dichlorobenzyl)-4-piperidinyl]-3-{3-[(2-thienylsulfonyl)methyl]-1,2,4-oxadiazol-5-yl}propanamide hydrochloride (0.04 g) as a pale yellow solid.

MS (+veES) 545 ((M+H)$^+$)

$^1$H NMR (DMSO) δ 10.51(1H,s); 8.21–8.13(2H,m); 7.91 (1H,s): 7.77–7.71(2H,m); 7.58–7.55(1H,m); 7.28–7.26(1H, m); 5.07–5.05(2H,m); 4.26–4.25(2H,m); 3.91(1H,m); 3.34–3.31(2H,m); 3.15–3.08(2H,m); 3.02–2.94(2H,m); 2.60–2.58(2H,m); 1.92–1.84(2H,m); 1.80–1.70(2H,m).

Example 354

N-[1-(3,4-Dichlorobenzyl)-4-piperidinyl]-3-[3-(4-pyridinyl)-1,2,4-oxadiazol-5-yl]propanamide Step i: 3-[3-(4-Pyridinyl)-1,2,4-oxadiazol-5-yl]propanoic acid N'-hydroxy-4-pyridinecarboximidazole (0.300 g) with dihydro-2,5-furandione (0.217 g) in dimethylformamide (2 drops) was heated for 4 times 30 seconds in a CEM MARS 5 microwave at 100% of 300 W to leave a fused mass. The reaction was allowed to cool and triturated with ethanol and filtered to leave 3-[3-(4-pyridinyl)-1,2,4-oxadiazol-5-yl]propanoic acid (0.241 g).

MS (+veES) 220 ((M+H)$^+$)

Step ii: N-[1-(3,4-Dichlorobenzyl)-4-piperidinyl]-3-[3-(4-pyridinyl)-1,2,4-oxadiazol-5-yl]propanamide For method refer to Example 353 step ii.

Purification was performed via chromatography (2.5% ethanol/dichloromethane). Solvent removed under reduced pressure to leave N-[1-(3,4-dichlorobenzyl)-4-piperidinyl]-3-[3-(4-pyridinyl)-1,2,4-oxadiazol-5-yl]propanamide (0.154 g) as a pale cream solid.

MS (+veES) 460 ((M+H)$^+$)

$^1$H NMR (DMSO) δ 8.81–8.79(2H, m); 7.96–7.90(3H, m); 7.60–7.56(2H, m); 7.30–7.27(1H, m); 3.53–3.51(1H, m); 3.44(2H, s); 3.23–3.19(2H, m); 2.71–2.68(4H, m); 2.05–1.97(2H, m); 1.71–1.67(2H, m); 1.44–1.32(2H, m).

Example 355

Cis-N-[1-(3,4-dichlorobenzyl)-4-piperidinyl]-2-[3-(2-pyridinyl)-1,2,4-oxadiazol-5-yl]cyclopropanecarboxamide Step i: Cis-2-[3-(2-pyridinyl)-1,2,4-oxadiazol-5-yl]cyclopropanecarboxylic acid N'-hydroxy-2-pyridinecarboximidamide (0.137 g) with 3-oxabicyclo[3.1.0]hexane-2,4-dione (0.112 g) in dimethylformamide (2 drops) was heated for 4 times 30 seconds in a CEM MARS 5 microwave at 100% of 300 W to leave a fused mass. The reaction was allowed to cool and triturated with diethyl ether and filtered to leave cis-2-[3-(2-pyridinyl)-1,2,4-oxadiazol-5-yl]cyclopropanecarboxylic acid (0.200 g).

MS (+veES) 232 ((M+H)$^+$)

Step ii: Cis-N-[1-(3,4-dichlorobenzyl)-4-piperidinyl]-2-[3-(2-pyridinyl)-1,2,4-oxadiazol-5-yl]cyclopropanecarboxamide Cis-2-[3-(2-pyridinyl)-1,2,4-oxadiazol-5-yl]cyclopropanecarboxylic acid (0.139 g) and N,N'-carbonyldiimidazole (0.110 g) in dichloromethane was stirred under nitrogen for 1 hour. 1-(3,4-dichlorobenzyl)-4-piperidinamine hydrochloride (0.198 g), and triethylamine (0.121 g) was then added and allowed to stir for 24 hours under nitrogen. Saturated sodium hydrogen carbonate was added to the reaction with the resulting solution being extracted three times with dichloromethane. The pooled organic phases were washed once with water, once with brine, dried over magnesium sulfate, filtered and the solvent removed under reduced pressure to leave an oil. This oil was purified by RPHPLC (75%–5%, 0.1% ammonium acetate/acetonitrile). The solvent was removed under reduced pressure to leave Cis-N-[1-(3,4-dichlorobenzyl)-4-piperidinyl]-2-[3-(2-pyridinyl)-1,2,4-oxadiazol-5-yl]cyclopropanecarboxamide (0.054 g) as a white solid.

MS (+veES) 472 ((M+H)$^+$)

$^1$H NMR (DMSO) δ 8.74–8.73(1H, m); 8.26–8.24(1H, m); 8.03–7.98(2H, m); 7.59–7.55(2H, m); 7.51(1H, s); 7.27–7.25(1H, m); 3.44–3.37(3H, m); 2.67–2.63(3H, m); 2.27–2.21(1H, m); 2.00–1.89(2H, m); 1.66–1.65(2H, m); 1.59–1.56(1H, m); 1.48–1.43(1H, m); 1.37–1.32(2H, m).

Example 356

Cis-N-[1-(3,4-Dichlorobenzyl)-4-piperidinyl]-3-[3-(2-pyridinyl)-1H-1,2,4-triazol-5-yl]propanamide Step i: 3-[3-(2-Pyridinyl)-1H-1,2,4-triazol-5-yl]propanoic acid 2-Pyridinecarbohydrazonamide (0.136 g) and dihydro-2,5-furandione (0.100 g) in 1 ml of dimethylacetamide was heated for 10 times 30 seconds in a CEM MARS 5 microwave at 100% of 300 W under nitrogen to leave 3-[3-(2- pyridinyl)-1H-1,2,4-triazol-5-yl]propanoic acid in 1 ml of dimethylacetamide.

MS (−veES) 217 ((M−H)+)

Step ii: N-[1-(3,4-Dichlorobenzyl)-4-piperidinyl]-3-[3-(2-pyridinyl)-1,2,4-triazol-5-yl]propanamide 3-[3-(2-Pyridinyl)-1,2,4-triazol-5-yl]propanoic acid (0.218 g) in 1 ml dimethylacetamide) and N,N'-carbonyldiimidazole (0.250 g) in dichloromethane was stirred under nitrogen for 30 minutes. 1-(3,4-Dichlorobenzyl)-4-piperidinamine hydrochloride (0.316 g), and triethylamine (0.218 g) was then added and allowed to stir for 2 hours under nitrogen. 1M sodium hydroxide was added to the reaction with the resulting solution being washed three times with dichloromethane. The aqueous phase was acidified with glacial acetic acid, with the water/acetic acid being removed under reduced pressure. Water was then added and extracted three times with dichloromethane. The pooled organic phases were extracted once with water and the water removed under reduced pressure to leave a white solid. This was then triturated with diethyl ether/dichloromethane, filtered and was purified by RPHPLC (75%–5%, 0.1% ammonium acetate/acetonitrile), solvent removed to leave N-[1-(3,4-dichlorobenzyl)-4-piperidinyl]-3-[3-(2-pyridinyl)-1H-1,2,4-triazol-5-yl]propanamide (0.02 g).

MS (+veES) 459 ((M+H)+)

$^1$H NMR (DMSO) δ 8.66–8.65(1H, m); 8.03–8.01(1H, m); 7.95–7.91(1H, m); 7.83–7.81(1H, m); 7.58–7.56(1H, m); 7.52(1H, m); 7.47–7.44(1H, m); 7.29–7.27(1H, m); 3.55–3.50(1H, m); 3.43(2H, s); 2.93–2.89(2H, m); 2.68–2.67(2H, m); 2.55–2.49(2H, m); 2.04–1.98(2H, m); 1.70–1.68(2H, m); 1.42–1.32(2H, m).

Example 357

N-[1-(3,4-Dichlorobenzyl)-4-piperidinyl]-2-(3-phenyl-1H-1,2,4-triazol-5-yl)acetamide (3-Phenyl-1H-1,2,4-triazol-5-yl)acetic acid (0.020 g) and N,N'-carbonyl diimidazole (0.016 g) in dichloromethane was stirred under nitrogen for 3 minutes. 1-(3,4-Dichlorobenzyl)-4-piperidinamine hydrochloride (0.031 g) and triethylamine (0.036 g) was then added and allowed to stir for 1 hour under nitrogen. Saturated sodium hydrogen carbonate was added to the reaction with the resulting solution being extracted three times with dichloromethane. The pooled organic phases were washed once with water, once with brine, dried over magnesium sulfate, filtered and the solvent removed under reduced pressure to a white solid. This was purified by RPHPLC (75%-5%, 0.1% ammonium acetate/acetonitrile). Saturated sodium hydrogen carbonate was added to the pooled collected fractions with the resulting solution being extracted three times with dichloromethane. The pooled organic phases were washed once with water, once with brine, dried over magnesium sulfate, filtered and the solvent removed under reduced pressure to leave N-[1-(3,4-dichlorobenzyl)-4-piperidinyl]-2-(3-phenyl-1H-1,2,4-triazol-5-yl)acetamide(0.031 g).

MS (+veES) 444 ((M+H)+)

$^1$H NMR (DMSO) δ 8.18–8.15(1H, m); 7.98–7.95(2H, m); 7.59–7.54(2H, m); 7.49–7.41(3H, m); 7.31–7.29(1H, m); 3.63(2H, s); 3.57–3.47(1H, m); 3.45(2H, s); 2.74–2.70 (2H, m); 2.08–2.01(2H, m); 1.77–1.74(2H, m); 1.48–1.38 (2H, m).

Example 358

N-[1-(3,4-Dichlorobenzyl)-4-piperidinyl]-2-(5-phenyl-1,3,4-oxadiazol-2-yl)acetamide acetate 3-(5-Phenyl-1,3,4-oxadiazol-2-yl)propanoic acid (0.175 g) and N,N'-carbonyldiimidazole (0.148 g) in dichloromethane was stirred under nitrogen for 30 minutes. 1-(3,4-Dichlorobenzyl)-4-piperidinamine hydrochloride (0.263 g), and triethylamine (0.126 g) was then added and allowed to stir for 2 hours under nitrogen. Saturated sodium hydrogen carbonate was added to the reaction, with the resulting solution being extracted three times with dichloromethane. The pooled organic phases were washed once with water, once with brine, dried over magnesium sulfate, filtered and the solvent removed under reduced pressure to leave a cream solid. This solid was purified by chromatography using 2.5% ethanol/dichloromethane. The solvent was removed under reduced pressure and was purified by RPHPLC (75%–5%, 0.1% ammonium acetate/acetonitrile) followed by 1 ml of glacial acetic acid being added and the solvent removed under reduced pressure to leave N-[1-(3,4-dichlorobenzyl)-4-piperidinyl]-2-(5-phenyl-1,3,4-oxadiazol-2-yl)acetamide acetate (0.024 g).

MS (+veES) 445 ((M+H)+)

$^1$H NMR (DMSO) δ 8.31–8.29(1H, m); 7.98–7.96(2H, m); 7.66–7.54(5H, m); 7.31–7.29(1H, m); 3.92(2H, s); 3.57–3.56(1H, m); 3.46(2H, s); 2.74–2.71(2H, m); 2.07–2.02(2H, m); 1.78–1.75(2H, m); 1.47–1.39(2H, m).

Example 359

N-[1-(3,4-Dichlorobenzyl)-4-piperidinyl]-2-[3-(2-pyridinyl)-1,2,4-oxadiazol-5-yl]acetamide Step i: Lithium [3-(2-pyridinyl)-1,2,4-oxadiazol-5-yl]acetate 2-(5-Methyl-1,2,4-oxadiazol-3-yl)pyridine (0.150 g) was stirred at −78° C. in dry tetrahydrofuran under nitrogen. (1.6M) n-butyl lithium (0.757 ml) was added dropwise so as to maintain the temperature at −78° C. After 30 minutes carbon dioxide was passed through the solution and the reaction was allowed to return to room temperature. Once the reaction had reached room temperature, water (1 ml) was added and all solvents were removed under reduced pressure to leave a yellow solid. This solid was triturated with ethyl acetate and filtered to leave a pale yellow solid (0.150 g).

$^1$H HMR (DMSO+D$_2$O) δ 8.75–8.73(1H, m); 8.12–8.00 (2H, m); 7.65–7.61(1H, m); 3.77(2H, s).

Step ii: N-[1-(3,4-Dichlorobenzyl)-4-piperidinyl]-2-[3-(2-pyridinyl)-1,2,4-oxadiazol-5-yl]acetamide Lithium [3-(2-pyridinyl)-1,2,4-oxadiazol-5-yl]acetate (0.140 g), 1-(3,4-dichlorobenzyl)-4-piperidinamine (0.170 g), PyBroP™ (0.400 g) were stirred under nitrogen in dimethyl formamide (15 ml). N,N-Diisopropylethylamine (0.171 g) was added and left to stir for 2 hours. 1M sodium hydroxide was added to the reaction, with the resulting solution being extracted three times with dichloromethane. The pooled organic phases were washed once with water, once with brine, dried over magnesium sulfate, filtered and the solvent removed under reduced pressure to leave product plus dimethylformamide. Water was added which resulted in precipitation of the product. The product was filtered and was purified by RPHPLC (75%–5%, 0.1% ammonium acetate/acetonitrile). After removal of the solvent under reduced pressure the resulting white solid was triturated with diethyl ether, filtered and dried to leave N-[1-(3,4-dichlorobenyzl)-4-piperidinyl]-2-[3-(2-pyridinyl)-1,2,4-oxadiazol-5-yl]acetamide (0.067 g). m.p. 145° C.

MS (+veES) 446 ((M+H)+)

$^1$H NMR (DMSO) δ 8.77–8.75(1H, m); 8.37–8.35(1H, m); 8.07–8.00(2H, m); 7.62–7.54(3H, m); 7.31–7.30(1H, m); 4.02(2H, s); 3.60–3.55(1H, m); 3.46(2H, s); 2.74–2.67 (2H, m); 2.08–2.03(2H, m); 1.78–1.76(2H, m); 1.48–1.39 (2H, m).

Example 360

N-[1-(4-Bromobenzyl)-4-piperidinyl]-2-(4-fluorophenyl)acetamide

2-(4-Fluorophenyl)-N-(4-piperidinyl)acetamide (WO97/36871; 1.00 g), 1-bromo-4-(bromomethyl)benzene (1.06 g) and potassium carbonate (0.877 g) in dimethylformamide (15 ml) were heated to 70° C., under nitrogen for 1 hour. Water was added to the reaction, with the resulting solution being extracted three times with dichloromethane. The pooled organic phases were washed once with water, once with brine, dried over magnesium sulfate, filtered and the solvent removed under reduced pressure to leave a cream solid. This solid was triturated with diethyl ether, filtered and recrystallised from ethanol/water to give water crystalline needles of N-[1-(4-bromobenzyl)-4-piperidinyl]-2-(4-fluorophenyl)acetamide. m.p. (+veES) 407 ((M+H)$^+$)

$^1$H NMR (DMSO) δ 7.99–7.98(1H, m); 7.51–7.49(2H, m); 7.28–7.24(4H, m); 7.12–7.06(2H, m); 3.51–3.46(1H, m); 3.41(2H, s); 3.36(2H, s); 2.72–2.69(2H, m); 2.01–1.96 (2H, m); 1.70–1.68(2H, m); 1.42–1.34(2H, m).

Example 361

2-(4-Fluorophenyl)-N-[1-(2-quinolinylmethyl)-4-piperidinyl]acetamide

2-(4-Fluorophenyl)-N-(4-piperidinyl)acetamide (WO97/36871; 0.05 g), 2-quinolinecarbaldehyde (0.033 g) and sodium triacetoxyborohydride (0.067 g) in dichloroethane (3 ml) were stirred under nitrogen for 24 hours. Saturated sodium hydrogen carbonate was added to the reaction, with the resulting solution being extracted three times with dichloromethane. The pooled organic phases were washed once with water, once with brine, dried over magnesium sulfate, filtered and the solvent removed under reduced pressure, triturated with diethyl ether/ethyl acetate and filtered to leave 2-(4-fluorophenyl)-N-[1-(2-quinolinylmethyl)-4-piperidinyl]acetamide (0.020 g).

MS (+veES) 378 ((M+H)$^+$)

$^1$H NMR (DMSO) δ 8.34–8.31(1H, m); 8.02–7.94(3H, m); 7.75–7.71(1H, m); 7.63–7.55(2H, m); 7.28–7.25(2H, m); 7.13–7.08(2H, m); 3.74(2H, s); 3.57–3.50(1H, m); 3.30 (2H, s); 2.79–2.76(2H, m); 2.16–2.11(2H, m); 1.73–1.70 (2H, m); 1.48–1.39(2H, m).

Example 362

N-[1-(3-Chloro-4-fluorobenzyl)-4-piperidinyl]-3-[3-(2-pyridinyl)-1,2,4-oxadiazol-5-yl]propanamide

3-[3-(2-Pyridinyl)-1,2,4-oxadiazol-5-yl]propanoic acid (0.218 g) and N,N'-carbonyldiimidazole (0.194 g) were stirred in dichloromethane (10 ml) under nitrogen for 1 hour. 1-(3-Chloro-4-fluorobenzyl)-4-piperidinamine (JP 59101483; 0.242 g) was then added and left to stir for 24 hours. Saturated sodium hydrogen carbonate was added to the reaction, with the resulting solution being extracted three times with dichloromethane. The pooled organic phases were washed once with water, once with brine, dried over magnesium sulfate, filtered and the solvent removed under reduced pressure, triturated with ethyl acetate/ethanol and filtered to leave N-[1-(3-chloro-4-fluorobenzyl)-4-piperidinyl]-3-[3-(2-pyridinyl)-1,2,4-oxadiazol-5-yl]propanamide. m.p. 150° C.

MS (+veAPC) 444 ((M+H)$^+$)

$^1$H NMR (DMSO) δ 8.75–8.74(1H, m); 8.05–7.99(2H, m); 7.95–7.93(1H, m); 7.61–7.58(1H, m); 7.48–7.45(1H, m); 7.37–7.30(1H, m); 7.30–7.26(1H, m); 3.53–3.51(1H, m); 3.42(2H, s); 3.21–3.17(2H, m); 2.71–2.66(4H, m); 2.02–1.96(2H, m); 1.70–1.67(2H, m); 1.42–1.33(2H, m).

Example 363

N-[1-(4-Chloro-3-fluorobenzyl)-4-piperidinyl]-3-[3-(2-pyridinyl)-1,2,4-oxadiazol-5-yl]propanamide

Step i: tert-Butyl 1-(4-chloro-3-fluorobenzyl)-4-piperidinylcarbamate

4-Chloro-3-fluorobenzaldehyde (0.793 g) and tert-butyl 4-piperidinylcarbamate (1.00 g) were stirred under nitrogen in dried tetrahydrofuran (25 ml). Sodium triacetoxyborohydride (1.266 g) was then added and left for 24 hours. Saturated sodium hydrogen carbonate was added to the reaction, with the resulting solution being extracted three times with dichloromethane. The pooled organic phases were washed once with water, once with brine, dried over magnesium sulfate, filtered and the solvent removed under reduced pressure to leave tert-butyl 1-(4-chloro-3-fluorobenzyl)-4-piperidinylcarbamate (1.80 g) as a white solid.

MS (+veAPC) 343 ((M+H)$^+$)

Step ii: 1-(4-Chloro-3-fluorobenzyl)-4-piperidine tert-Butyl 1-(4-chloro-3-fluorobenzyl)-4-piperidinylcarbamate (1.80 g) in dichloromethane (20 ml) was stirred under nitrogen. Trifluoroacetic acid (5 ml) was then added dropwise and the reaction was left to stir for 2 hours. 1M sodium hydroxide was added to the reaction until basic, with the resulting solution being extracted three times with dichloromethane. The pooled organic phases were washed once with water, once with brine, dried over magnesium sulfate, filtered and the solvent removed under reduced pressure. Product purified by chromatography (5% ethanol/dichloromethane to 10% ethanol/dichloromethane) and solvent removed under reduced pressure to leave an oil which crystallised over the period of 48 hours. The resulting solid was triturated with diethyl ether and filtered to leave 1-(4-chloro-3-fluorobenzyl)-4-piperidinamine (0.500 g) as a white solid.

Step iii: N-[1-(4-Chloro-3-fluorobenzyl)-4-piperidinyl]-3-[3-(2-pyridinyl)-1,2,4-oxadiazol-5-yl]propanamide 3-[3-(2-Pyridinyl)-1,2,4-oxadiazol-5-yl]propanoic acid (0.136 g) and N,N'-carbonyldiimidazole (0.114 g) were stirred in dichloromethane (10 ml) under nitrogen for 1 hour. 1-(4-Chloro-3-fluorobenzyl)-4-piperidinamine (0.150 g) was then added and left to stir for 2 hours. Saturated sodium hydrogen carbonate was added to the reaction, with the resulting solution being extracted three times with dichloromethane. The pooled organic phases were washed once with water, once with brine, dried over magnesium sulfate, filtered and the solvent removed under reduced pressure to leave an oil. This was triturated with diethyl ether which caused product the to crystallise. After filtration, the product was washed with diethyl ether and dried to N-[1-(4-chloro-3-fluorobenzyl)-4-piperidinyl]-3-[3-(2-pyridinyl)-1,2,4-oxadiazol-5-yl]propanamide. m.p. 132° C.

MS (+veES) 444 ((M+H)$^+$)

$^1$H NMR (DMSO) δ 8.76–8.74(1H, m); 8.05–7.99(2H, m); 7.95–7.94(1H, m); 7.61–7.58(1H, m); 7.54–7.50(1H, m); 7.32–7.28(1H, m); 7.16–7.14(1H, m); 3.55–3.47 (1H, m); 3.44(2H, s); 3.21–3.17(2H, m); 2.71–2.66(4H, m); 2.03–1.97(2H, m); 1.70–1.67(2H, m); 1.42–1.33(2H, m).

Example 364

2-(4-Chlorophenoxy)-N-[1-[(3,4-dichlorophenyl)methyl]-piperidin-4-yl]-acetamide

The product from Example 1 step (ii) was dissolved in dichloromethane (10 ml) containing triethylamine (0.081 g)

and the solution was cooled to 0° C. 4-Chlorophenoxyacetyl chloride (88 mg) in dichloromethane (3 ml) was added dropwise, the cooling bath was removed and the resulting solution was stirred for 1 hour. Ethyl acetate, water and brine were added and the phases were separated. The organic phase was dried, filtered and evaporated to give an oil which was purified by reverse phase HPLC (with a gradient eluent system (25% MeCN/NH$_4$OAc$_{aq}$ (0.1%) to 95% MeCN/NH$_4$OAc$_{aq}$ (0.1%)) to give the title compound (0.049 g).

$^1$H NMR: (CDCl$_3$): δ 1.51 (2H, ddd), 1.89–1.96 (2H, m), 2.15 (2H, td), 2.77 (2H, d), 3.43 (2H, s), 3.85–3.96 (1H, m), 4.44 (2H, s), 6.37 (1H, d), 6.85 (2H, dt), 7.14 (1H, dd), 7.26–7.29 (2H, m), 7.37 (1H, d), 7.43 (1H, d)

Example 365

N-(1-benzyl-4-piperidinyl)-3-[3-(2-pyridinyl)-1,2,4-oxadiazol-5-yl]propanamide

To a solution of 3-(3-Pyridin-2-yl-[1,2,4]oxadiazol-5-yl)-propionic acid (1 g) in tetrahydrofuran (5 ml), was added carbonyldiimidazole (0.74 g). The mixture was stirred for 10 minutes before addition of 1-benzyl-piperidin-4-ylamine (1 ml) in tetrahydrofuran (5 ml). The reaction mixture was stirred for 15 minutes then partitioned between ethyl acetate (20 ml) and water (20 ml). The organic layer was separated, dried (MgSO$_4$) and solvent removed by evaporation. Purification by Biotage® 40S eluting 3%MeOH/0.5% 880 ammonia/dichloromethane gave the title compound (0.93 g).

MS:ESI 392 (+H)

$^1$H NMR (CDCl$_3$): δ 1.44 (2H, ddd), 1.88 (2H, d), 2.10 (2H, t), 2.73–2.78 (2H, m), 2.80 (2H, t), 3.33 (2H, t), 3.46 (2H, s), 3.75–3.86 (1H, m), 5.57 (1H, d), 7.23–7.32 (5H, m), 7.42 (1H, ddt), 7.84 (1H, tt), 8.10 (1H, dd), 8.79 (1H, td).

Example 366

N-(2-{[1-(3,4-Dichloro-benzyl)-piperidin-4-yl]-methyl-amino}-ethyl)-2-(2-fluoro-phenyl)-acetamide Step i: (2-Methylamino-ethyl)-carbamic acid tert-butyl ester To a solution of (2-amino-ethyl)-carbamic acid-tert-butyl ester (5 g) and triethylamine (6.5 ml) in tetrahydrofuran (1000 ml) at 0° C. was added methyliodide (1.94 ml) dropwise over a period of 1 hour. The mixture was allowed to warm to ambient temperature and stirred for 72 hours before removal of solvents by evaporation. The residue was partitioned between ethyl acetate and water. The organic layer was separated, dried (MgSO$_4$) and solvent removed by evaporation to give the title compound (3.7 g).

MS: ESI 57((CH$_3$)$_4$C+), 118 (M+H–(CH$_3$)$_4$C)

Step ii: (2-{[1-(3,4-Dichloro-benzyl)-piperidin-4-yl]-methyl-amino}-ethyl)-carbamic acid tert-butyl ester To a solution of dichlorobenzyl-piperidin-4-one (Example 74, step (i), 4.8 g) and acetic acid (1 ml) in dichloromethane (100 ml) was added (2-methylamino-ethyl)-carbamic acid tert-butyl ester (3.26 g) and the mixture was stirred for 5 minutes before addition of sodium triacetoxyborohydride (7.9 g). The reaction mixture was stirred for 12 hours before addition of sodium bicarbonate solution. The mixture was stirred for ½ hour and then partitioned between water and dichloromethane. The organic layer was separated, dried (MgSO$_4$) and solvent removed by evaporation. Purification by Biotage® 40S eluting 10%MeOH/2% triethylamine/dichloromethane gave the title compound (1.7 g).

MS: ESI 316/318 (+H–(CH$_3$)$_4$COCO)

$^1$H NMR: (CDCl$_3$): δ 1.44 (9H, s), 1.50–1.60 (4H, m), 1.65–1.72 (2H, m), 1.95 (2H, td), 2.23 (3H, s), 2.34 (1H, tt), 2.88 (2H, d), 3.14–3.20 (2H, m), 3.41 (2H, s), 4.95–5.01 (1H, m), 7.13–7.15 (1H, m), 7.37 (1H, d), 7.42 (1H, d).

Step iii: N$^1$-[1-(3,4-Dichloro-benzyl)-piperidin-4-yl]-N$^1$-methyl-ethane-1,2-diamine (2-{[1-(3,4-Dichloro-benzyl)-piperidin-4-yl]-methyl-amino}-ethyl)-carbamic acid tert-butyl ester (1.7 g) was dissolved in 6M HCl (20 ml) and stirred for 12 hours. The solvent was evaporated and the residue was azeotroped with toluene and then sodium bicarbonate solution was added. The mixture was stirred for 10 minutes and the product was extracted with dichloromethane. The solvent was removed by evaporation to give the title compound (0.75 g).

MS: ESI 316/318 (+H)

Step iv: N-(2-{[1-(3,4-Dichloro-benzyl)-piperidin-4-yl]-methyl-amino}-ethyl)-2-(2-fluoro-phenyl)-acetamide Prepared by the method of Example 359 step (ii) using N$^1$-[1-(3,4-Dichloro-benzyl)-piperidin-4-yl]-N$^1$-methyl-ethane-1,2-diamine and 2-fluorophenylacetic acid.

MS: ESI 452/454 (+H)

$^1$H NMR: (CDCl$_3$): δ 2.08–1.94 (2H, m), 2.37–2.33 (2H, m), 2.95 (3H, s), 3.18 (2H, t), 3.41 (2H, m), 3.66–3.78(4H, m), 3.75 (2H, s), 3.84 (1H, m), 4.38 (2H, s), 7.16–7.28 (2H, m), 7.36–7.42 (2H, m), 7.45 (1H, d), 7.22 (1H, d).

Example 367

N-[1-(3,4-dichlorobenzyl)-4-piperidinyl]-N-methyl-2-(4-fluorophenyl)acetamide

Step i: [1-(3,4-Dichlorobenzyl)-piperidin-4-yl]-methyl-amine

To a solution of 1-(3,4-Dichloro-benzyl)-piperidin-4-one (3.1 g) in dichloromethane (50 ml) and acetic acid (0.69 ml) was added methylamine (6 ml of a 1M solution in tetrahydrofuran). The mixture was stirred for 5 minutes before the addition of sodium triacetoxyborohydride (3 g) and the resulting mixture stirred for 72 hours. Sodium bicarbonate solution (100 ml) added and the mixture stirred vigorously for 5 minutes before extraction of the product with dichloromethane (2×200 ml). The organics were separated, bulked and dried, (MgSO$_4$). Purification by Biotage® 40S eluting 10%MeOH/0.5% 800 ammonia/dichloromethane gave the sub-title compound (1.8 g).

MS: ESI 273/275 (+H)

$^1$H NMR: (CDCl$_3$): δ 1.36 (2H, qd), 1.82–1.91 (2H, m), 2.03 (2H, td), 2.36 (1H, tt), 2.43 (3H, s), 2.76–2.83 (2H, m), 3.43 (2H, s), 7.15 (1H, dd), 7.37 (1H, d), 7.42 (1H, d).

Step ii: N-[1-(3,4-dichlorobenzyl)-4-piperidinyl]-2-(4-fluorophenyl)acetamide

To a solution of 4-fluorophenylacetic acid (100 mg) in tetrahydrofuran (3 ml) was added carbonyldiimidazole (105 mg). The mixture was stirred for 10 minutes before addition of [1-(3,4-dichlorobenzyl)-piperidin-4-yl]-methyl-amine (177 mg) in tetrahydrofuran (2 ml). Stirring was continued for 1 hour then solvent removed by evaporation. Purification by Biotage® 40S eluting 2%MeOH/0.5% 880 ammonia/dichloromethane gave the title compound (166 mg).

MS: ESI 273/275 (M+H)

$^1$H NMR: (CDCl$_3$) δ 1.57 (1H, d), 1.69 (1H, qd), 1.76–1.84 (1H, m), 1.88 (1H, q), 2.10 (2H, td), 2.85–2.90 (1H, m), 2.85 (3H, s), 3.42 (2H, s), 3.58 (1H, tt), 3.67 (2H, s), 4.51 (1H, tt), 7.00 (2H, t), 7.11–7.15 (1H, m), 7.18–7.23 (2H, m), 7.37 (1H, d), 7.41 (1H, dd).

Example 368

N-[1-[(3,4-dichlorophenyl)methyl]-4-piperidinyl]-2-(2-pyrimidinyloxy)-acetamide

Step i: Ethyl 2-pyrimidinyloxyacetate

Ethyl glycolate (1.04 g) was dissolved in tetrahydrofuran (10 ml) and the solution was cooled to 0° C. Sodium hydride (60% suspension in oil, 0.43 g) was added and the suspension was stirred and then sonicated in an ultrasonic bath. 2-Chloropyrimidine (1.14 g) was added and the mixture was sonicated for a further 110 min. Ammonium chloride solution was added and the mixture was extracted thrice with ethyl acetate, the organic phases were washed with brine and dried, filtered and evaporated. The residue was purified by chromatography eluting with iso-hexane:ethyl acetate (13:7) to give the subtitle compound (1.40 g) as an oil.

$^1$H NMR (299.944 MHz, CDCl$_3$) δ 1.26 (t, J=6.8 Hz, 3H), 4.24 (q, J=7.1 Hz, 2H), 4.93 (s, 2H), 6.98 (t, J=4.8 Hz, 1H), 8.53 (d, J=4.8 Hz, 2H).

Step ii: 2-Pyrimidinyloxyacetic acid

Ethyl 2-pyrimidinyloxyacetate (1.4 g) was dissolved in ethanol (10 ml). Sodium hydroxide (2M aq) was added and the mixture was stirred for 64 h. The solvent was evaporated and the residue was dissolved in water, filtered and the acidified with concentrated hydrochloric acid. The resulting precipitate was collected and dried to give the subtitle compound (0.698 g).

$^1$H NMR (399.98 MHz, DMSO) δ 4.85 (s, 2H), 7.09 (t, J=4.9 Hz, 1H), 8.56 (d, J=4.8 Hz, 2H).

Step iii: N-[1-[(3,4-dichlorophenyl)methyl]-4-piperidinyl]-2-(2-pyrimidinyloxy)-acetamide The title compound was prepared from the product of Example 1 step (ii) (hydrochloride salt, 335 mg) and 2-pyrimidinyloxyacetic acid (170 mg) using the method of Example 94. Yield 140 mg. m.p. 120–122° C.

$^1$H NMR (399.978 MHz, CDCl$_3$) δ 1.50 (q, J=11.6 Hz, 2H), 1.91 (d, J=11.9 Hz, 2H), 2.13 (t, J=11.1 Hz, 2H), 2.77 (d, J=11.4 Hz, 2H), 3.42 (s, 2H), 3.86–3.95 (m ,1H), 4.87 (s, 2H), 6.49 (d, J=6.9 Hz, 1H), 7.05 (t, J=4.9 Hz, 1H), 7.14 (m, 1H), 7.37 (d, J=8.3 Hz, 1H), 7.42 (s, 1H), 8.57 (d, J=4.8 Hz, 2H).

Example 369

N-[2-[[8-[(3,4-Dichlorophenyl)methyl]-8-azabicyclo[3.2.1]oct-3-yl]amino]ethyl]-3-methoxy-benzamide, bis toluene sulfonic acid salt

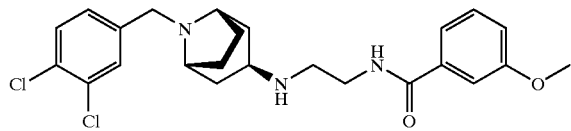

Step i: 8-[(3,4-Dichlorophenyl)methyl]-8-azabicyclo[3.2.1]octan-3-one 2,5-Dimethoxytetrahydrofuran (4.92 g) was stirred in hydrochloric acid (1M, 25 ml) for 1 hour. 3,4-Dichlorobenzylamine (5 ml) was added to hydrochloric acid (1M, 15 ml) and the resulting suspension was added to the first solution. Phosphate buffer solution (pH 5.5, 250 ml) was added followed by sodium hydroxide (1.6 g). A solution of acetone dicarboxylic acid (4.77 g) in phosphate buffer solution (pH 5.5, 90 ml) was added to the mixture and the solution was stirred. A yellow solid formed and the mixture was left to stand for 64 h. The aqueous supernatant was decanted and hydrochloric acid (2.5M) was added to the solid along with ethyl acetate. The layers were separated and the aqueous phase was extracted twice with dichloromethane containing a little methanol. The organic layers were combined and evaporated to give a crude oil (ca 7 g). A portion of the product (ca 2.5 g) was purified by chromatography eluting with dichloromethane:methanol (19:1) to give the subtitle compound (1.62 g) as a yellow oil.

$^1$H NMR (299.944 MHz, CDCl$_3$) δ 1.62–1.70 (m, 2H), 2.09–2.15 (m, 2H), 2.23 (d, J=15.9 Hz, 2H), 2.67 (d, J=16.7 Hz, 2H), 3.43–3.49 (m, 2H), 3.68 (s, 2H), 7.26 (d, J=8.7 Hz, 1H), 7.41 (d, J=7.5 Hz, 1H), 7.54 (s, 1H)

Step ii: Carbamic acid, Endo-[2-[[8-[(3,4-dichlorophenyl)methyl]-8-azabicyclo[3.2.1]oct-3-yl]amino]ethyl]-1,1-dimethylethyl ester 8-[(3,4-Dichlorophenyl)methyl]-8-azabicyclo[3.2.1]octan-3-one (751 mg) and carbamic acid, (2-aminoethyl)-1,1-dimethylethyl ester (520 mg) were dissolved in dichloroethane (23 ml). Sodium triacetoxyborohydride (697 mg) was added and the suspension was stirred at room temperature for 20 hours. Dichloromethane was added and the solution was washed with sodium bicarbonate solution, then with water and then with brine. Chromatography of the residue eluting with ethyl acetate:methanol:triethylamine (80:19:1) gave the subtitle compound (688 mg) as an oil.

$^1$H NMR (399.978 MHz, CDCl$_3$) δ 1.45 (s, 9H), 1.52 (d, J=14.4 Hz, 2H), 1.96–2.09 (m, 6H), 2.67 (t, J=5.8 Hz, 2H), 2.88 (t, J=6.4 Hz, 1H), 3.08–3.12 (m, 2H), 3.21 (q, J=5.7 Hz, 2H), 3.48 (s, 2H), 4.80–4.95 (m, 1H), 7.22 (dd, J=8.3, 2.0 Hz, 1H), 7.37 (d, J=7.9 Hz, 1H), 7.49 (d, J=2.0 Hz, 1H)

Step iii: N-[2-[[8-[(3,4-Dichlorophenyl)methyl]-8-azabicyclo[3.2.1]oct-3-yl]amino]ethyl]-3-methoxy-benzamide, bis toluene sulfonic acid salt Carbamic acid, [2-[[8-[(3,4-dichlorophenyl)methyl]-8-azabicyclo[3.2.1]oct-3-yl]amino]ethyl]-,1,1-dimethylethyl ester (337 mg) was dissolved in dichloromethane (3 ml) and trifluoroacetic acid (3 ml) was added. The resulting solution was stirred for 1 hour then the volatiles were evaporated. The residue was dissolved in dichloromethane (3 ml) and triethylamine (1 ml) was added followed by 3-methoxybenzoyl chloride (120 μl). The solution was stirred overnight. The solvent was evaporated and the residue was purified by RPHPLC (gradient ammonium acetate 1% aqueous:acetonitrile (25% acetonitrile to 95% acetonitrile)). Excess tosic acid in ether was added to the residue and the resultant salt was recrystallised from a mixture of ethyl acetate-ethanol with a little cyclohexane to give the title compound (77 mg). m.p. 180–182.5° C.

$^1$H NMR (399.98 MHz, DMSO) δ 2.10–2.24 (m, 4H), 2.29 (s, 6H), 2.39–2.47 (m, 4H), 3.21–3.28 (m, 2H), 3.52–3.57 (m, 1H), 3.57–3.63 (m, 2H), 3.80 (s, 3H), 3.85–3.91 (m, 2H), 4.21 (d, J=5.4 Hz, 2H), 7.11 (d, J=9.4 Hz, 4H), 7.13–7.18 (m, 1H), 7.38–7.45 m, 3H), 7.48 (d, J=7.9 Hz, 4H), 7.56 (d, J=6.7 Hz, 1H), 7.78 (d, J=8.2 Hz, 1H), 7.84–7.90 (m, 1H), 8.38–8.52 (m, 2H), 8.81–8.87 (m, 1H), 9.44–9.51 (m, 1H).

Example 370

Endo-N-[8-[(3,4-dichlorophenyl)methyl]-8-azabicyclo[3.2.1]oct-3-yl]-3-(2-pyridinyl)-1,2,4-oxadiazole-5-propanamide hydrochloride Step i: Endo-8-[(3,4-dichlorophenyl)methyl]-8-azabicyclo[3.2.1]octan-3-amine 8-[(3,4-Dichlorophenyl)methyl]-8-azabicyclo[3.2.1]octan-3-one (350 mg) was dissolved in dry methanol (12 ml) and ammonium acetate (1 g) was added. The mixture was stirred to get partial solution and then sodium cyanoborohydride (106 mg) was added. The mixture was heated under reflux for 150 minutes, then allowed to cool to room temperature. The methanol was evaporated, the residue was partitioned between sodium hydroxide and dichloromethane, and the aqueous phase was extracted twice with dichloromethane. The organic phases were combined, dried, filtered and evaporated to give the subtitle compound. [M+H]$^+$ (ES+) 285

Step ii: Endo-N-[8-[(3,4-dichlorophenyl)methyl]-8-azabicyclo[3.2.1]oct-3-yl]-3-(2-pyridinyl)-1,2,4-oxadiazole-5-propanamide hydrochloride 3-(2-Pyridinyl)-1,2,4-oxadiazole-5-propanoic acid (305 mg) was suspended in dichloromethane (6 ml) and oxalyl chloride (0.5 ml) was added. The mixture was stirred overnight. Toluene (1 ml) was added to the solution, the volatiles were evaporated, then the residue was redissolved in dichloromethane (2 ml). Endo-8-[(3,4-dichlorophenyl)methyl]-8-azabicyclo[3.2.1]octan-3-amine (all from step(i)) was dissolved in dichloromethane (4 ml) containing triethylamine (0.5 ml) and then cooled in an ice bath. The acid chloride solution was added to the amine and the mixture was stirred for 1 hour. Water was added to the reaction mixture and the phases were separated. The aqueous phase was extracted twice with dichloromethane, the organic phases were dried, filtered and evaporated. The residue was purified by RPHPLC (gradient ammonium acetate 1% aqueous:acetonitrile (25% acetonitrile to 95% acetonitrile)). The product was suspended in ether and the ethereal hydrochloric acid was added, the suspension was stirred and then the diethyl ether was evaporated. The residue was dissolved in hot ethyl acetate containing ethanol and crystallisation was induced by adding iso-hexane to give the title compound (47 mg).

$^1$H NMR (399.98 MHz, DMSO) δ 1.99–1.90 (m, 2H), 2.41–2.20 (m, 6H), 2.77 (t, J=6.8 Hz, 2H), 3.23 (t, J=6.9 Hz, 2H), 3.81–3.72 (m, 3H), 4.15 (d, J=6.2 Hz, 2H), 7.63–7.58 (m, 1H, 7.67 (dd, J=7.6, 2.3 Hz, 2H), 7.76 (d, J=9.3 Hz, 1H), 8.06–7.99 (m, 3H), 8.11 (d, J=4.1 Hz, 1H), 8.75 (d, J=4.6 Hz, 1H), 10.13 (t, J=5.6 Hz, 1H).

Example 371

2-[4-(acetylamino)phenoxy]-N-[1-[(3,4-dichlorophenyl)methyl]-4-piperidinyl]-acetamide Step i: Methyl (4-acetaminophenoxy)acetate 4-Acetaminophenol (1.51 g), potassium carbonate (1.38 g) and methyl bromoacetate (1.0 ml) were combined in acetone (40 ml) and heated to reflux for 5 hours. The mixture was allowed to cool to room temperature, filtered and evaporated. The residue was dissolved in ethyl acetate, washed with water and then with brine then dried, filtered and evaporated to give the subtitle compound (2.32 g).

$^1$H NMR (399.978 MHz, CDCl$_3$) δ 2.16 (s, 3H), 3.80 (s, 3H), 4.62 (s, 2H), 6.87 (d, J=9.1 Hz, 2H), 7.07 (br s, 1H), 7.40 (d, J=9.0 Hz, 2H)

Step ii: (4-Acetaminophenoxy)acetic acid

Methyl (4-acetaminophenoxy)acetate was hydrolysed following the method of Example 368 step (ii) to give the subtitle compound (1.85 g).

$^1$H NMR (399.98 MHz, DMSO) δ 2.00 (s, 3H), 4.61 (s, 2H), 6.84 (d, J=9.0 Hz, 2H), 7.46 (d, J=9.0 Hz, 2H), 9.80 (s, 1H).

Step iii: 2-[4-(acetylamino)phenoxy]-N-[1-[(3,4-dichlorophenyl)methyl]-4-piperidinyl]-acetamide The title compound was prepared from the product of Example 1 step (ii) (free base, 281 mg) and (4-acetaminophenoxy)acetic acid (229 mg) using a method hereinbefore described (yield 40 mg). m.p. 177–178.5° C.

$^1$H NMR (299.946 MHz, DMSO) δ 1.51 (qd, J=10.5, 3.7 Hz, 2H), 1.72–1.63 (m, 2H), 2.00 (s, 3H), 2.05 (t, J=3.7 Hz, 2H), 2.77–2.68 (m, 2H), 3.45 (s, 2H), 3.70–3.57 (m, 1H), 4.39 (s, 2H), 6.88 (d, J=9.0 Hz, 2H), 7.29 (dd, J=8.1, 1.7 Hz, 1H), 7.47 (d, J=8.8 Hz, 2H), 7.54 (d, J=1.5 Hz, 1H), 7.58 (d, J=8.1 Hz, 1H), 7.89 (d, J=8.1 Hz, 1H), 9.79 (s, 1H).

Example 372

N-[1-[(3,4-dichlorophenyl)methyl]-4-piperidinyl]-4-hydroxy-benzeneacetamide

The title compound was prepared from the product of Example 1 step (ii) (free base, 172 mg) and 4-hydroxyphenylacetic acid (135 mg) using a method hereinbefore described (yield 57 mg). m.p. 72–97° C.

$^1$H NMR (399.98 MHz, DMSO) δ 1.37 (q, J=7.0 Hz, 2H), 1.69 (d, J=11.3 Hz, 2H), 2.02 (t, J=5.3 Hz, 2H), 2.71 (d, J=11.3 Hz, 2H), 3.23 (s, 2H), 3.44 (s, 2H), 3.55–3.42 (m, 1H), 6.66 (d, J=8.5 Hz, 2H), 7.02 (d, J=8.5 Hz, 2H), 7.29 (d, J=8.2 Hz, 1H), 7.53 (s, 1H), 7.58 (d, J=8.2 Hz, 1H), 7.87 (d, J=7.9 Hz, 1H), 9.18 (s, 1H).

Example 373

Exo-N-[8-[(3,4-dichlorophenyl)methyl]-8-azabicyclo[3.2.1]oct-3-yl]-3-(2-pyridinyl)-1,2,4-oxadiazole-5-propanamide Step i: Endo-8-[(3,4-dichlorophenyl)methyl]-8-azabicyclo[3.2.1]octan-3-ol 8-[(3,4-Dichlorophenyl)methyl]-8-azabicyclo[3.2.1]octan-3-one (330 mg) was dissolved in tetrahydrofuran (5 ml) and cooled to 0° C. Lithium tris (3-ethylpentyl-3-oxy) aluminohydride solution (0.5M, 2.5 ml) was added dropwise and the mixture was allowed to attain room temperature overnight. Sodium sulfate decahydrate (ca 2 g) was added and the suspension was stirred for 1 hour. The reaction mixture was diluted with ethyl acetate, filtered through kieselguhr and evaporated. The residue was purified by chromatography eluting with dichloromethane:methanol (9:1) to give the subtitle compound 161 mg.

$^1$H NMR (399.978 MHz, CDCl$_3$) δ 1.59 (d, J=8.1 Hz, 2H), 1.64 (t, J=11.4 Hz, 2H), 1.86–1.81 (m, 2H), 2.00–1.97 (m, 2H), 3.21–3.18 (m, 2H), 3.55 (s, 2H), 3.95 (septet, J=5.6 Hz, 1H), 7.21 (d, J=8.2 Hz, 1H), 7.37 (d, J=7.4 Hz, 1H), 7.50 (s, 1H).

Step ii: Exo-2-[8-[(3,4-dichlorophenyl)methyl]-8-azabicyclo[3.2.1]oct-3-yl]-1H-isoindole-1,3(2H)-dione Endo-8-[(3,4-dichlorophenyl)methyl]-8-azabicyclo[3.2.1]octan-3-ol (556 mg), phthalimide (321 mg) and polymer bound triphenylphosphine (821 mg) were combined in tetrahydrofuran (10 ml). Diethylazodicaboxylate (330 μl) was added and the mixture was stirred gently overnight. Additional phosphine (0.5 g) and diethylazodicaboxylate (200 μl) were added and the mixture was stirred for an additional 5 days. The reaction mixture was diluted with ethyl acetate and filtered; the residue was washed with ethyl acetate and methanol. The filtrate was evaporated, and chromatographed eluting with 9:1 ethyl acetate:methanol. RPHPLC of the product (gradient ammonium acetate 1% aqueous:acetonitrile (25% acetonitrile to 100% acetonitrile)) gave the subtitle compound (90 mg).

$^1$H NMR (399.978 MHz, CDCl$_3$) δ 1.47–1.39 (m, 2H), 1.78 (d, J=7.7 Hz, 2H), 2.14–2.02 (m, 2H), 2.64 (t, J=11.8 Hz, 2H), 3.36–3.25 (m, 2H), 3.92–3.81 (m, 2H), 4.56 (septet, J=6.1 Hz, 1H), 7.41–7.32 (m, 2H), 7.59–7.55 (m, 1H), 7.74–7.69 (m, 2H), 7.86–7.82 (m, 2H).

Step iii: Exo-8-[(3,4-dichlorophenyl)methyl]-8-azabicyclo[3.2.1]octan-3-amine

Exo-2-[8-[(3,4-dichlorophenyl)methyl]-8-azabicyclo[3.2.1]oct-3-yl]-1H-isoindole-1,3(2H)-dione (90 mg) was dissolved in ethanol (6 ml) containing dichloromethane (3 ml); hydrazine hydrate (0.2 ml) was added and the resulting solution was stirred at room temperature for 26 hours. The suspension was filtered and the filtrate was evaporated to give the subtitle compound (55 mg).

$^1$H NMR (399.978 MHz, CDCl$_3$) δ 1.51–1.43 (m, 2H), 1.59 (q, J=4.9 Hz, 2H), 1.75–1.67 (m, 2H), 2.00–1.94 (m, 2H), 3.02–2.92 (m, 1H), 3.18–3.12 (m, 2H), 3.50 (s, 3H), 7.21 (d, J=8.2 Hz, 1H), 7.37 (d, J=8.2 Hz, 1H), 7.50 (s, 1H).

Step iv: Exo-N-[8-[(3,4-dichlorophenyl)methyl]-8-azabicyclo[3.2.1]oct-3-yl]-3-(2-pyridinyl)-1,2,4-oxadiazole-5-propanamide Prepared following the method of Example 370 step (iii) but without salt formation to give the title compound (15 mg). m.p. 177.5–178° C.

$^1$H NMR (299.946 MHz, DMSO): δ 1.63–1.43 (m, 6H), 1.99–1.90 (m, 2H), 2.64 (t, J=7.1 Hz, 2H), 3.11–3.06 (m, 2H), 3.18 (t, J=6.2 Hz, 2H), 3.49 (s, 2H), 3.97–3.83 (m, 1H), 7.32 (dd, J=8.3, 1.9 Hz, 1H), 7.62–7.56 (m, 3H), 7.87 (d, J=8.1 Hz, 1H), 8.06–7.97 (m, 2H), 8.75 (dt, J=3.7, 0.8 Hz, 1H).

Example 374

(R) N-[1-[1-(4-bromophenyl)ethyl]-4-piperidinyl]-3-(2-pyridinyl)-1,2,4-oxadiazole-5-propanamide Step i: (R)-1-[1-(4-Bromophenyl)ethyl]-4-piperidinone (R)-(4-Bromophenyl)ethylamine (1.01 g) and potassium carbonate (1.45 g) were dissolved in a mixture of ethanol (13 ml) and water (6 ml) and then heated to a vigorous reflux. A solution of 4-hydroxy-4-methoxy-1,1-dimethyl-piperidinium iodide (J. Chem. Soc. Perkin Trans. 2, (1984) 1647) (1.47 g) in warm water (6 ml) was added dropwise over 40 minutes; reflux was maintained for a further 12 hours, then the reaction was allowed to cool to room temperature. The mixture was evaporated and ethyl acetate and water were added and the phases were separated. The aqueous phase was extracted twice with ethyl acetate, the organic layer was washed with brine, dried, filtered and evaporated. Chromatography of the residue eluting with iso-hexane:ethyl acetate (3:2) gave the subtitle compound (804 mg).

$^1$H NMR (399.978 MHz, CDCl$_3$) δ 2.66–2.80 (m, 4H), 1.38 (d, J=6.9 Hz, 3H), 2.42 (t, J=6.2 Hz, 4H), 3.58 (q, J=6.7 Hz, 1H), 7.24 (d, J=8.5 Hz, 2H), 7.46 (d, J=9.0 Hz, 4H).

Step ii: (R)-1-[1-(4-Bromophenyl)ethyl]-4-piperidinamine

Prepared following the general method of Example 370 step (i) (R)-1-[1-(4-bromophenyl)ethyl]-4-piperidinone (420 mg) ammonium acetate (0.80 g) and sodium cyanoborohydride (120 mg) to give the subtitle compound (449 mg).

$^1$H NMR (399.978 MHz, CDCl$_3$) δ 1.33 (d, J=6.9 Hz, 3H), 1.43–1.26 (m, 2H), 1.73 (d, J=12.3 Hz, 1H), 1.81 (d, J=12.6 Hz, 1H), 2.03–1.90 (m, 2H), 2.60 (tt, J=10.6, 5.1 Hz, 1H), 2.71 (d, J=13.6 Hz, 1H), 2.94 (d, J=11.3 Hz, 1H), 3.37 (q, J=6.7 Hz, 1H), 7.18 (d, J=8.5 Hz, 2H), 7.43 (d, J=8.2 Hz, 2H)

Step iii: (R) N-[1-[1-(4-bromophenyl)ethyl]-4-piperidinyl]-3-(2-pyridinyl)-1,2,4-oxadiazole-5-propanamide Prepared following a method as hereinbefore described using (R)-1-[1-(4-bromophenyl)ethyl]-4-piperidinamine (449 mg), 3-(2-pyridinyl)-1,2,4-oxadiazole-5-propanoic acid (0.31 g), 1-hydroxybenzotriazole (0.20 g), 4-(N,N-dimethylamino)-pyridine (0.13 g) and 1-ethyl-3-[3-(dimethylamino)-propyl]carbodiimide hydrochloride (0.30 g) to give the title compound (40 mg). m.p. 153–155° C.

$^1$H NMR (399.98 MHz, DMSO) δ 1.23 (d, J=6.7 Hz, 3H), 1.40–1.26 (m, 2H), 1.66–1.61 (m, 1H), 1.73–1.67 (m, 1H), 1.97–1.86 (m, 2H), 2.64–2.59 (m, 1H), 2.66 (t, J=7.2 Hz, 2H), 2.84–2.79 (m, 1H), 3.18 (t, J=7.2 Hz, 2H), 3.42 (q, J=6.4 Hz, 1H), 3.48–3.39 (m, 1H), 7.25 (d, J=8.5 Hz, 2H), 7.49 (d, J=8.5 Hz, 2H), 7.59 (ddd, J=6.7, 4.6, 2.1 Hz, 1H), 7.91 (d, J=7.4 Hz, 1H), 8.04–7.99 (m, 2H), 8.75 (dt, J=4.4, 1.4 Hz, 1H).

Example 375

(S) N-[1-[1-(4-bromophenyl)ethyl]-4-piperidinyl]-3-(2-pyridinyl)-1,2,4-oxadiazole-5-propanamide Prepared following an analogous series of steps to example 374 but using (S)-(4-bromophenyl)ethylamine to give the title compound. m.p. 141.5–143° C. α$_D$ _29.55° (c=0.13, methanol, 21° C.)

$^1$H NMR (299.946 MHz, DMSO) δ 1.23 (d, J=6.7 Hz, 3H), 1.26–1.41 (m, 2H), 1.64 (t, J=8.1 Hz, 2H), 1.92 (q, J=11.2 Hz, 2H), 2.58–2.67 (m, 1H), 2.67 (t, J=7.2 Hz, 2H), 2.78–2.85 (m, 1H), 3.18 (t, J=7.1 Hz, 2H), 3.37–3.46 (m, 1H), 3.42 (q, J=6.7 Hz, 1H), 7.25 (d, J=6.7 Hz, 2H), 7.49 (d, J=8.5 Hz, 2H), 7.57–7.62 (m, 1H), 7.91 (d, J=7.7 Hz, 1H), 7.98–8.05 (m, 2H), 8.75 (d, J=7.5 Hz, 1H).

Example 385

1-[3,4-Dichlorobenzyl]-N-[3-(3-pyridinyl)propyl]-4-piperidinamine

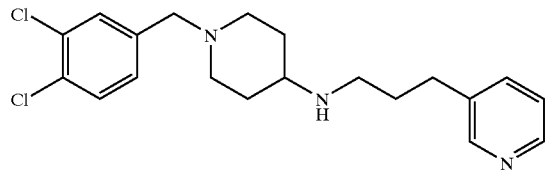

The title compound was prepared from 1-(3,4-dichlorobenzyl)piperidine-4-amine (free base 187 mg), 3-(3-pyridinyl)propanal (125 mg), sodium triacetoxyborohydride (70 mg), and 0.02 ml acetic acid, stirred together for 2 hrs in dichloromethane (10 ml). Water was added, the mixture neutralised with sodium bicarbonate and the organic phase separated, dried and chromatographed on silica with ethyl acetate/methanol (9:1) as eluant, to give the title compound (70 mg) as a colourless oil.

MS [M+H]$^+$ (ES+) 378 $^1$H NMR: (CDCl$_3$) δ 1.36–1.40 (2H, m), 1.75–1.85 (4H m), 2.0 (2H, t), 2.1–2.2 (2H, m), 2.4–2.45 (1H m), 2.6–2.7 (3H, m), 2.75–2.79 (2H, m), 3.4 (2H, s), 7.1–7.54 (5H, d), 8.44 (2H, m).

Example 386

2-[(1,1'-Biphenyl)-4-yloxy]-N-[1-(3,4-dichlorobenzyl)-4-piperidinyl]acetamide

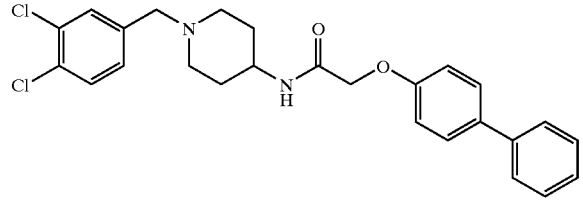

MS [M+H]$^+$ (ES+) 469 $^1$H NMR: (CDCl$_3$) δ 1.46–1.50 (2H, m), 1.7–1.8 (2H, m), 2.0–2.1 (2H, m), 2.5–2.6 (2H, m), 3.45 (2H, s), 3.65–3.7 (1H, m), 4.5 (2H, s), 7.25–7.3 (2H, m), 7.27–7.63 (9H, m), 8.0 (1H, d).

Example 387

N-[1-(3,4-dichlorobenzyl)-4-piperidinyl]-4-phenyl-3-butenamide

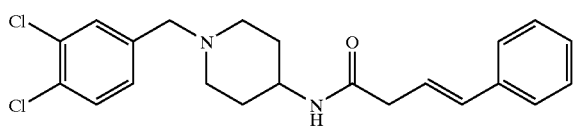

MS [M+H]+ (ES+) 403 ¹H NMR: (CDCl₃) δ 1.46–1.40 (2H, m), 1.85–1.95 (2H, d), 2.05–2.15 (2H, t), 2.75–2.79 (2H, d), 3.1 (2H, d), 3.4 (2H, s), 3.85–3.95 (1H, m), 5.45 (1H, m), 6.3 (1H, m), 6.5 (1H, d), 7.07–7.43 (8H, m).

Example 388

N-[1-(3,4-dichlorobenzyl)-4-piperidinyl]-3-(3-methoxyphenyl)-2-propenamide.

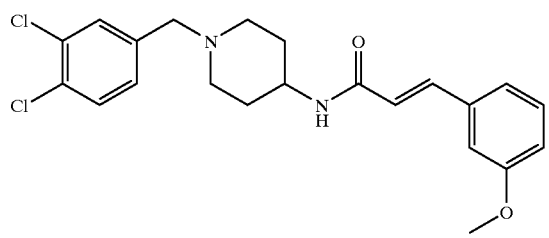

MS [M+H]+ (ES+) 419 ¹H NMR: (CDCl₃) δ 1.46–1.50 (2H, m), 2.0 (2H, m), 2.15–2.25 (2H, m), 2.75–2.85 (2H, m), 3.4 (2H, s), 3.8 (3H, s), 3.94–4.05 (1H, m), 5.5 (1H, d), 6.35–6.4 (1H, d), 6.9–7.5 (7H, m), 7.6 (1H, d).

Example 389

N-[1-(3,4-dichlorobenzyl)-4-piperidinyl]-3-(4-iodophenoxy)propanamide.

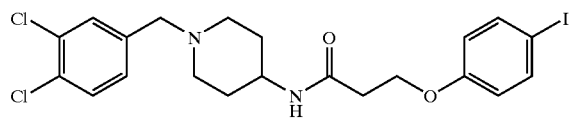

MS [M+H]+ (ES+) 533 ¹H NMR: (CDCl₃) δ 1.46–1.50 (2H, m), 1.9 (2H, d), 2.1–2.2 (2H, t), 2.6 (2H, m), 2.75–2.85 (2H, d), 3.4 (2H, d), 3.8–3.9 (1H, m), 4.20 (2H, m), 6.65–6.7 (2H m), 7.1–7.2 (1H, d), 7.35–7.45 (2H, m), 7.54–7.6 (2H, m).

Example 390

N-[1-(3,4-dichlorobenzyl)-4-piperidinyl]-N'-(4-methoxyphenyl)succinamide

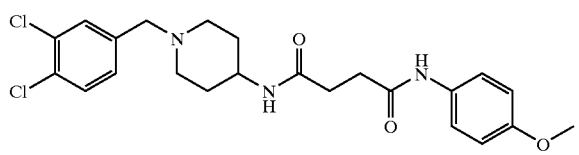

MS [M+H]+ (ES+) 464 ¹H NMR: (CDCl₃) δ 1.4 (2H, m), 1.6–1.65 (2H, m), 2.05 (2H, m), 2.45 (2H, m), 2.65–275 (2H, m), 3.0 (2H, m) 3.45 (2H, s), 3.5 (1H, m), 3.7 (3H, s), 5.9 (1H, m), 6.85 (2H, d), 7.3–7.6 (4H, m), 7.7 (1H, d), 9.7 (1H, s).

Example 391

N-[1-(3,4-dichlorobenzyl)-4-piperidinyl]-2-[(5-phenyl-2-pyrimidinyl)oxy] acetamide

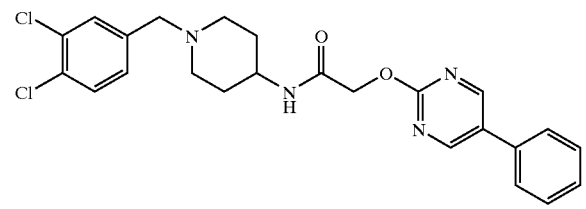

MS [M+H]+ (ES+) 471 ¹H NMR: (CDCl₃) δ 1.46–1.50 (2H, m), 1.9–2.0 (2H, m), 2.0–2.1 (2H, m), 2.75–2.85 (2H, m), 3.4 (2H, s), 3.9–4.0 (1H, m), 4.92 (2H, s), 6.53 (1H, d), 7.1–7.6 (7H, m), 7.7 (1H, s), 8.76 (2H, s).

Example 392

N-[1-(4-iodobenzyl)-4-piperidinyl]-2-(5-phenyl-2-pyrimidinyl)thio]acetamide

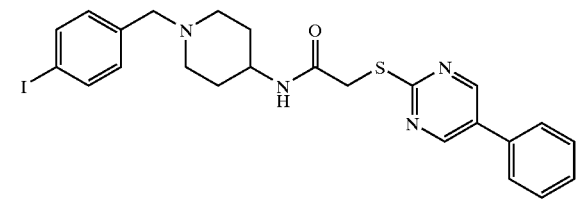

MS [M+H]+ (ES+) 545 ¹H NMR: (CDCl₃) δ 1.46–1.50 (2H, m), 1.8 (2H, m), 2.1–2.2 (2H, t), 2.65 (2H, m), 3.4 (2H, s), 3.9 (3H, m), 6.8 (1h, d), 7.0 (2H, m), 7.5–7.7 (7H, m), 8.8 (2H, d).

Example 393

N-[1-(3,4-dichlorobenzy)-4-piperidinyl]-2-[(2-pyrimidinyl)thio]acetamide

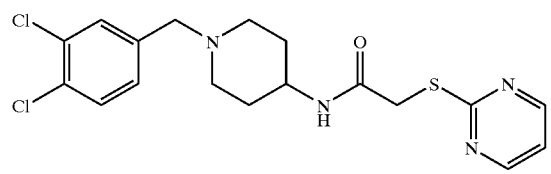

MS [M+H]+ (ES+) 412 ¹H NMR: (CDCl₃) δ 1.46–1.50 (2H, m), 1.8 (2H, m), 2.1 (2H, m), 2.65 (2H, m), 3.4 (2H, s), 3.8 (3H, m), 6.90 (1H m), 7.05–7.2 (4H, m), 8.58 (2H, d).

Example 394

2-[(5-Bromo-2-pyrimidinyl)thio]-N-[1-(3,4-dichlorobenzy)-4-piperidinyl]acetamide

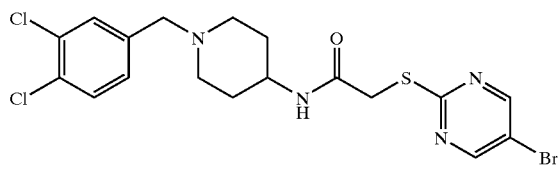

MS [M+H]+ (ES+) 491 $^1$H NMR: (CDCl$_3$) δ 1.46–1.50 (2H, m), 1.8 (2H, m), 2.15 (2H, m), 2.6 (2H, m), 3.4 (2H, s), 3.8 (3H, m), 6.6 (1H, d), 7.1 (1H m), 7.3–7.4 (2H, m) 8.58 (2H, d).

Example 395

N-[1-(3,4-difluororobenzyl)-4-piperidinyl]-2-(4-pyridinylthio)acetamide

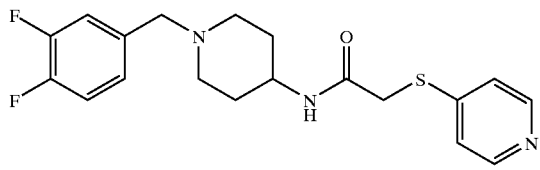

MS [M+H]+ (ES+) 378 $^1$H NMR: (CDCl$_3$) δ 1.36–1.40 (2H, m), 1.8 (2H, m), 2.05 (2H m), 2.65 (2H, m), 3.4 (2H, m), 3.67 (2H, s), 3.8 (1H, m), 6.5 (1H, m), 6.9–7.24 (4H, m) 8.48 (2H, d).

Example 396

N-[1-(3,4-dichlorobenzy)-4-piperidinyl]-3-(5-phenyl-1H-pyrrol-2-yl)propanamide

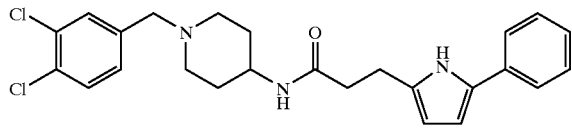

MS [M+H]+ (ES+) 454 $^1$H NMR: (CDCl$_3$) δ 1.36–1.40 (2H, m), 1.87 (2H, m), 2.05 (2H m), 2.5 (2H, m), 2.65 (2H, m), 2.96 (2H, m), 3.4 (2H, s), 3.8 (1H, m), 5.35 (1H, d), 5.95–6.0 (1H, m) 6.38 (1H, m), 7.1–7.5 (8H, m), 9.5 (1H m).

Example 397

N-[1-(3,4-dichlorobenzy)-4-piperidinyl]-N'-(5-phenyl-2-pyrimidinyl)-1,2-ethandiamine

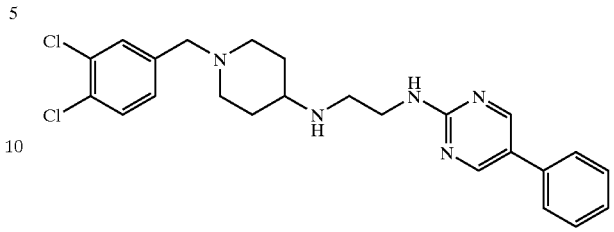

The title compound (20 mg) was prepared by heating at reflux N$^1$-[1-(3,4-dichlorobenzyl)-4-piperidinyl]-1,2-ethanediamine (100 mg) and 2-chloro-5-phenypyrimidine (100 mg) and Hunigs' base (100 mg) in toluene for 8 hours. The mixture was purified by chromatography on silica, with ethyl acetate methanol (9:1) as eluant to give the title compound as a yellow oil. MS [M+h]+ (ES+) 456/8 $^1$H NMR: (CDCl$_3$) δ 1.51 (2H, m), 1.75 (2H, m), 2.15 (2H, td), 2.9 (2H, m), 3.05 (1H, m), 3.15 (2H, m), 3.44 (2H, m), 3.8 (2H, m), 6.65 (1H, m), 7.0–7.4 (8H, m), 8.5 (2H, m).

Example 398

N-[5-bromo-2-pyrimidinyl]-N'-[1-(3,4-dichlorobenzy)-4-piperidinyl]-1,2-ethandiamine

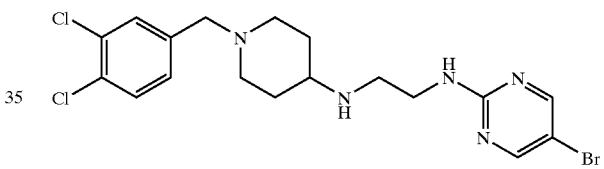

Prepared by the method of Example 397 amine (200 mg), 2-chloro-5-bromopyrimidine (130 mg), Hunigs' base (200 mg) to give the title compound (20 mg). MS [M+H]+ (ES+) 458/60 $^1$H NMR: (CDCl$_3$) δ 1.4 (2H, m), 1.75 (2H, m), 2.05 (2H, td), 2.85 (2H, m), 3.0 (1H, m), 3.15 (2H, m), 3.44 (2H, m), 3.75 (2H, m), 6.8 (1H, m), 7.0–7.4 (3H, m), 8.25 (2H, m).

Example 399

2-[(2-Chloro-4-pyrimidinyl)amino]-N-[1-(3,4-dichlorobenzyl)-4-piperidinyl]acetamide

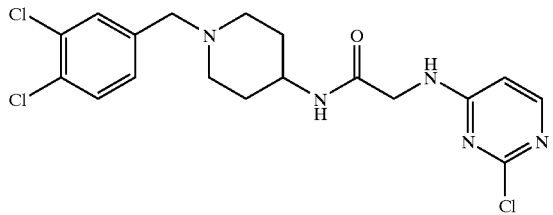

MS [M+H]+ (ES+) 430/32 $^1$H NMR: (CDCl$_3$) δ 1.40–1.45 (2H, m), 1.97 (2H, m), 2.15 (2H m), 2.75 (2H, d), 3.4 (2H, s), 3.8 (1H, m), 4.05 (2H, d), 5.75 (1H, d), 5.84 (1H m), 6.38 (1H, d), 7.1–7.15 (1H d), 7.36–7.42 (2H, m), 8.0 (1H d).

Example 401

2-[(5-Bromo-2-pyrimidinyl)oxy]-N-[1-(3,4-dichlorobenzyl)-4-piperidinyl]-2-acetamide

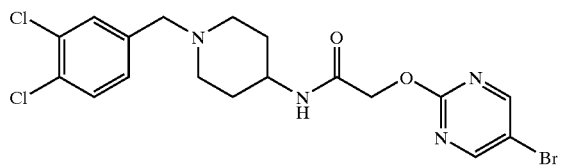

MS [M+H]$^+$ (ES+) 475 $^1$H NMR: (CDCl$_3$) δ 1.46–1.50 (2H, m), 1.87 (2H, m), 2.15 (2H, m), 2.75 (2H, m), 3.4 (2H, s), 3.9 (1H, m) 4.8 (2H, s), 6.38 (1H, d), 7.1–7.15 (1H m), 7.4 (2H, m), 8.6 (2H, s).

Example 402

N-[1-(3,4-dichlor benzy)-4-piperidinyl]-2-(1,3-di x -1,3-dihydro-2H-is indol-2-yl)acetamide

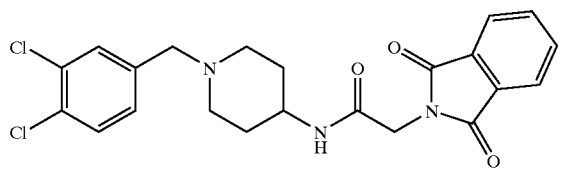

MS [M+H]$^+$ (ES+) 446 $^1$H NMR: (CDCl$_3$) δ 1.46–1.50 (2H, m), 1.87 (2H, m), 2.15 (2H m), 2.75 (2H, m), 3.4 (2H, s), 3.8 (1H, m), 4.3 (2H s), 5.65 (1H, m), 7.1–7.36 (3H, m) 7.38–7.78 (2H, m), 7.87–7.95 (2H, m).

Example 403

N-[1-(3,4-dichlorobenzyl)-4-piperidinyl]-N-[2-(2-pyridinylthio)ethylamine, dihydrochloride

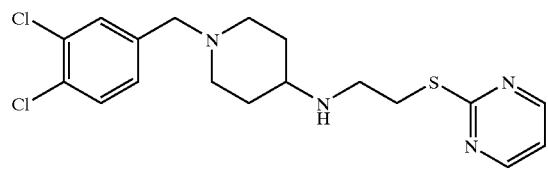

$^1$H NMR: (CDCl$_3$) (of the free base): δ 1.4 (2H, m) 1.85 (2H, m), 2.05 (2H, m) 2.55 (2H, td), 2.8 (2H, m), 3.0 (1H, m), 3.3 (2H, m), 3.42 (2H, s), 6.9–7.5 (4H, m), 8.5 (2H, m).

Example 404

N-[1-(3,4-dichlorobenzyl)-4-piperidinyl]-3-(phenylthio)propanamide

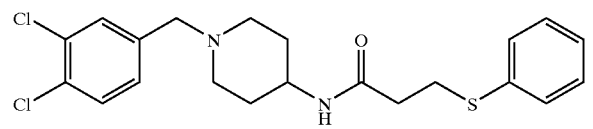

MS [M+h]$^+$ (ES+) 423 $^1$H NMR: (CDCl$_3$) δ 1.36–1.40 (2H, m), 1.87 (2H, m), 2.15 (2H m), 2.45 (2H, m), 2.76 (2H, m), 3.2 (2H, m), 3.4 (2H, s), 3.8 (1H, m), 5.4 (1H, d), 7.1–7.5 (8H m).

Example 405

N'-[1-(3,4-dichlorobenzyl)-4-piperidinyl]-2-[4-(trifluoromethoxy)phenoxy]acetohydrazide

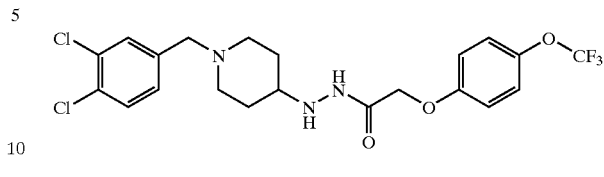

The title compound was prepared from 3,4-dichlorobenzyl-4-piperidone (J. Med. Chem, 1999, 42, 3629; 100 mg), 2-[4(trifluoromethoxy)phenoxy] acetohydrazide (100 mg), sodium triacetoxyborohydride (100 mg), and 0.02 ml acetic acid, stirred together for 2 hours in dichloromethane by the method of Example 369 step ii. MS [M+H]$^+$ (ES+) 492 $^1$H NMR: (CDCl$_3$) δ 1.4–1.6 (3H, m) 1.7 (2H, m), 2.0 (2H, m) 2.7–2.9 (2H, m), 3.4 (2H, m), 4.4 (3H, m), 5.3 (1H, s) 6.9 (2H, m), 7.2–7.5 (4H, m), 7.8 (1H, d).

Example 406

N-[1-(3,4-dichlorobenzyl)-4-piperidinyl]-N-[3-[3-(2-pyridinyl)-1,2,4-oxadiazo-5-yl]propyl]amine

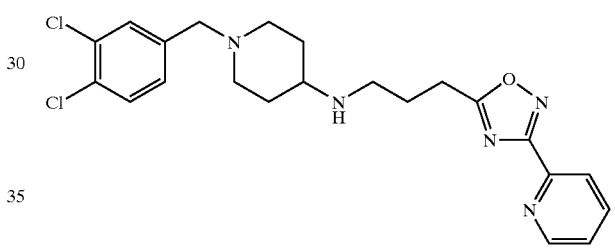

The title compound (29 mg) was prepared from 3,4-dichlorobenzylpiperidine-4-amine (100 mg free base), 2-[5-(3-bromopropyl)-1,2,4-oxadiazol-3-yl]pyridine (100 mg), potassium carbonate (100 mg) in dimethyl formamide (1 ml) were heated together in the microwave for 30 secs, water was added and the product extracted into dichloromethane and chromatographed on silica with ethyl acetate/methanol (9:1) as eluant. MS [M+H]$^+$ (ES+) 446 $^1$H NMR: (CDCl$_3$) δ 1.4 (2H, m) 1.7–1.9 (4H, m), 2.0–2.1 (4H, m) 2.46 (1H, m), 2.75 (2H, m), 3.1 (2H, t), 3.4 (2H, s), 7.15–7.45 (4H, m), 7.85 (1H, t) 8.1 (1H, d) 8.8 (1H, d).

Example 407

N-[2-[1-(3,4-dichlorobenzyl)-4-piperidinyl]amino]ethyl]-3-(methylsulphonyl)benzamide

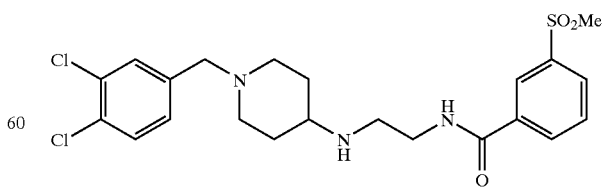

Prepared from N-(2-aminoethyl)-N-[1-(3,4-dichlorobenzyl)-4-piperidinyl]-2,2,2-trifluoroacetamide (100 mg), 3-methylsulphonylbenzoic acid (50 mg) and carbonyldiimidazole (40 mg). The product obtained was stirred together with sodium hydroxide (40 mg) in 50:50 methanol/water for 12 hrs, extracted into dichloromethane and purified by chromatography on silica with ethyl acetate/methanol (9:1) as eluant, to give the title compound (25 mg). MS [M+H]$^+$ (ES+) 485 $^1$H NMR: (CDCl$_3$) δ 1.4 (2H, m) 1.9 (2H, m), 2.0–2.1 (1H, m) 2.6 (1H, m), 2.8 (2H, m), 2.95 (2H, m) 3.1 (3H, m) 3.4 (2H, s), 3.6 (2H, m), 7.15 (2H, m), 7.4 (2H, m), 7.65 (1H, t) 8.1 (2H d) 8.4 (1H, d).

Example 408

3-[5-(4-chlorophenyl-4H-1,2,4-triazol-3-yl]-N-[1-(3,4-dichlorobenzyl)-4-piperidinyl])propanamide

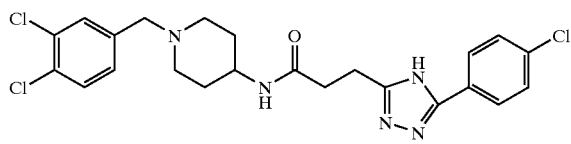

MS [M+H]$^+$ (ES+) 493 $^1$H NMR: (CDCl$_3$) δ 1.6 (2H, m), 1.87 (2H, m), 2.25 (2H m), 2.65 (2H, m), 2.86 (96 (2H, m), 3.14 (2H, m), 3.5 (2H, s), 3.85 (1H, m), 6.0 (1H, m) 7.23 (1H, m), 7.4 (3H m), 7.45 (1H m), 8.0 (2H m).

Example 409

N-[1-(3,4-dichl r benzyl)-4-piperidinyl]-3-(2-pyridinyl)propanamide

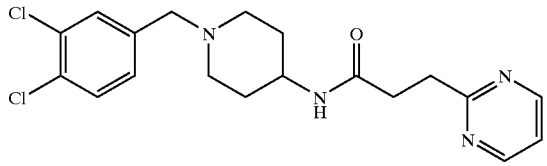

MS [M+H]$^+$ (ES+) 394 $^1$H NMR: (CDCl$_3$) δ 1.46 (2H, m), 1.8 (2H, m), 2.15 (2H m), 2.75 (4H, m), 3.3 (2H m), 3.45 (2H, s), 3.8 (1H, m), 6.05 (1H, m), 7.1 (2H, m) 7.38 (1H, m), 7.45 (1H m), 8.65 (2H m)

Example 410

N-[1-(3,4-dichlorobenzyl)-4-piperidinyl]-4-(4-(methylsulphonyl)phenyl-4-oxobutanamide

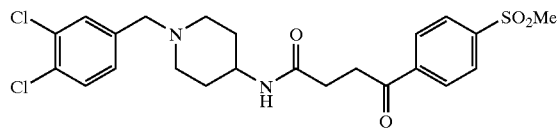

MS [M+H]$^+$ (ES+) 497 $^1$H NMR: (CDCl$_3$) δ 1.4–1.5 (2H, m), 1.9 (2H, m), 2.15 (2H m), 2.65 (2H, m), 2.78 (2H m), 3.1 (3H s), 3.35 (2H m), 3.4 (2H, s), 3.8 (1H, m), 5.55 (1H, m), 7.16 (1H, m) 7.38 (2H, m), 8.05 (2H, m), 8.2 (2H m).

Example 411

N-[1-(3,4-dichlorobenzyl)-4-piperidinyl]-N'-[4-(methylsulphonyl) benzylamine

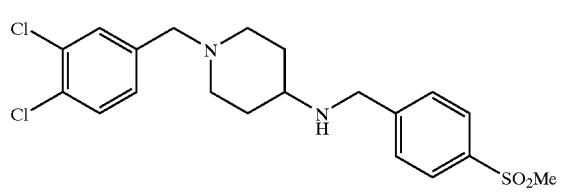

MS [M+H]$^+$ (ES+) 427 $^1$H NMR: (CDCl$_3$) δ 1.4 (2H, m), 1.8–1.9 (2H, m), 2.0 (2H, m), 2.5 (2H, td), 2.8 (2H, m), 3.0 (2H, s), 3.4 (2H, s), 3.94 (2H, s), 7.15 (1H, m), 7.4 (2H, m), 7.55 (2H, d) 7.9 (2H, d).

Example 412

N-[1-(3,4-dichl r benzyl)-4-piperidinyl]-N'-[(2-pyridinyl) succinamide

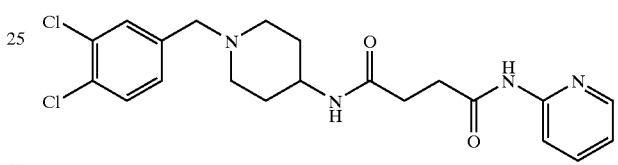

MS [M+H]$^+$ (ES+) 435 $^1$H NMR: (CDCl$_3$) δ 1.6 (2H, m), 1.87 (2H, m), 2.05 (2H m), 2.65 (2H, m), 2.76 (4H m), 3.4 (2H, s), 3.8 (1H, m), 5.65 (1H, m), 7.0 (1H, m), 7.1 (1H, m), 7.38 (2H, d), 7.7 (1H m), 8.2 (1H m), 8.27 (1H m), 8.65 (1H m).

Example 413

N-[1-(3,4-dichlorobenzyl)-4-piperidinyl]-2-(4-phenyl-1,3-thiazol-2-yl))acetamide

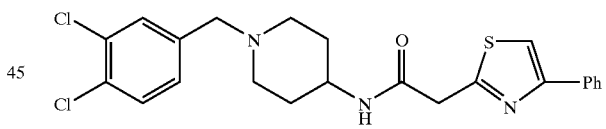

MS [M+H]$^+$ (ES+) 461 $^1$H NMR: (CDCl$_3$) δ 1.50 (2H, m), 1.87 (2H, m), 2.15 (2H m), 2.65 (2H, m), 3.4 (2H, s), 3.85 (1H m), 4.0 (2H, s), 7.15 (1H, d) 7.3–7.5 (6H, m), 7.9 (2H d).

Example 414

N-[1-(3,4-dichlorobenzyl)-4-piperidinyl]-2-(2-phenyl-1,3-thiazol-4-yl))acetamide

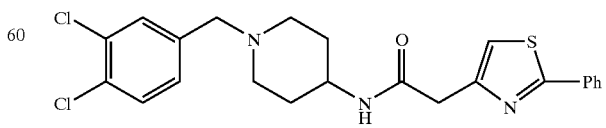

MS [M+H]$^+$ (ES+) 461 $^1$H NMR: (CDCl$_3$): δ 1.45 (2H, m), 1.90 (2H, m), 2.15 (2H, m), 2.65 (2H, m), 3.25 (2H, s), 3.7 (2H, s), 3.85 (1H, m), 7.15 (2H, m) 7.4 (2H, d), 7.5 (3H m), 8.0 (2H m).

Example 415

N-[1-(3,4-difluorobenzyl)-4-piperidinyl]-3-(3-2-pyridinyl-1,2,4-oxadiazol-5-yl]propanamide

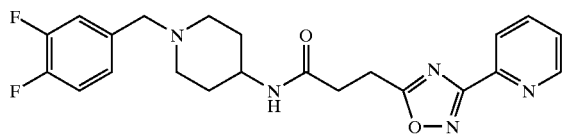

MS [M+H]$^+$ (ES+) 428 $^1$H NMR: (CDCl$_3$) δ 1.36–1.45 (2H, m), 2.0 (2H, m), 2.1–2.2 (2H, t), 2.7–2.85 (4H, m), 3.34 (2H, d), 3.4 (2H, d), 3.8 (1H, m), 5.6 (1H, d), 7.0–7.2 (3H m), 7.4 (1H m), 7.8 (1H, m) 8.1 (1H, d), 8.8 (1H, d)

dryness and dichloromethane (20 ml) and trifluoroacetic acid (2 ml) added, stirred for 3 hrs, then neutralised with aqueous sodium bicarbonate, the organic phase separated, dried and evaporated to give the title compound (250 mg) as a yellow oil. MS [M+H]$^+$ (ES+) 496/8 c) N-trifluoroacetyl-N-[2-[1-(3,4-dichlor benzyl)-4-piperidinyl]amin]ethyl]-3-methoxybenzamide The title compound (30 mg) was prepared from the product above (40 mg) 3-methoxybenzoyl chloride (20 mg) and triethylamine (50 mg) using one of the methods described above. MS [M+H]$^+$ (ES+) 580 $^1$H NMR: (CDCl$_3$) δ 0.9 (6H, m) 1.2–1.4 (6H, m), 1.6–1.85 (4H, m) 2.8 (1H, m), 3.3 (4H, m), 3.6–3.8 (5H, m), 3.8 (2H, s), 7.0 (1H, m), 7.1 (1H, m), 7.35–7.45 (3H, m), 8.25 (1H, t).

Further compounds of formula (I), all according to formula (Ic), are shown in the table below.

(Ic)

$$R^1-(Q)_m-(CR^2R^3)_n-T^1-N(R^*)-\text{piperidine}-N-Z-R^6$$

| Example | R$^1$ | (Q)$_m$ | (CR$^2$R$^3$)$_n$ | T$^1$ | R* | Z | R$^6$ |
|---|---|---|---|---|---|---|---|
| 380 | 4-Cl—C$_6$H$_4$ | O | CH$_2$ | C(O) | H | CH$_2$C(O)NH | 2-Cl-5-CH$_3$—C$_6$H$_3$ |
| 381 | 4-Cl—C$_6$H$_4$ | O | CH$_2$ | C(O) | H | (CH$_2$)$_3$ | C$_6$H$_5$ |
| 382 | 3-(pyridin-2-yl)-1,2,4-oxadiazol-5-yl | O | CH$_2$ | C(O) | H | allyl | C$_6$H$_5$ |
| 383 | 2-(cyclopropyl-NH)-pyrimidin-4-yl | m = 0 | n = 0 | — | CH$_3$ | CH$_2$ | 3,4-Cl$_2$—C$_6$H$_3$ |
| 384 | 2-(pyridin-3-yl)-pyrimidin-4-yl | m = 0 | n = 0 | — | CH$_3$ | CH$_2$ | 3,4-Cl$_2$—C$_6$H$_3$ |
| 400 | pyrimidin-2-yl | S | CH$_2$ | C(O) | H | C(O) | 3,4-Cl$_2$—C$_6$H$_3$ |

Example 416

N-trifluoroacetyl-N-[2-[1-(3,4-dichlorobenzyl)-4-piperidinyl]amino]ethyl]-3-methoxybenzamide

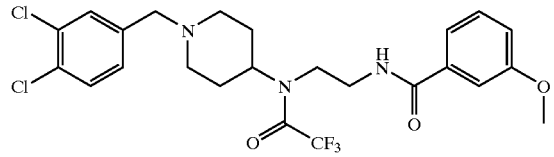

a) tert-butyl 2-{[1-(3,4-dichlorobenzyl)-4-piperidinyl]amino}ethylcarbamate

The sub-title compound (800 mg) was prepared from 3,4-dichlorobenzyl-4-piperidone (1.3 g) tert-butyl 2-aminoethylcarbamate (0.8 g), sodium triacetoxyborohydride (100 mg), and 0.02 ml acetic acid, stirred together for 2 hrs in dichloromethane. The sub-titled compound was isolated by standard procedures. MS [M+H]$^+$ (ES+) 402 b) N-(2-aminoethyl)-N-[1-(3,4-dichlorobenzyl)-4-piperidinyl]-2,2,2-trifluoroacetamide A mixture of the above amine (800 mg), and triethylamine (0.5 ml) in dichloromethane (50 ml), treated with trifluoroacetic anhydride (420 mg) over 30 mins, evaporated to Pharmacological Analysis
Calcium flux [Ca$^{2+}$]$_i$ assay
a) Human eosinophils Human eosinophils were isolated from EDTA anticoagulated peripheral blood as previously described (Hansel et al., J. Immunol. Methods, 1991, 145, 105–110). The cells were resuspended (5×10$^6$ ml$^{-1}$) and loaded with 5 μM FLUO-3/AM+Pluronic F127 2.2 μl/ml (Molecular Probes) in low potassium solution (LKS; NaCl 118 mM, MgSO$_4$ 0.8 mM, glucose 5.5 mM, Na$_2$CO$_3$ 8.5 mM, KCl 5 mM, HEPES 20 mM, CaCl$_2$ 1.8 mM, BSA 0.1%, pH 7.4) for one hour at room temperature. After loading, cells were centrifuged at 200 g for 5 min and resuspended in LKS at 2.5×10$^6$ ml$^{-1}$. The cells were then transferred to 96 well FLIPr plates (Poly-D-Lysine plates from Becton Dickinson pre-incubated with 5 μM fibronectin for two hours) at 100 ml/well. The plate was centrifuged at 200 g for 5 min and the cells were washed twice with LKS (200 μl; room temperature).

A compound of the Examples was pre-dissolved in dimethylsulphoxide and added to a final concentration of 0.1% (v/v) dimethylsulphoxide. Assays were initiated by the addition of an A$_{50}$ concentration of eotaxin and the transient increase in fluo-3 fluorescence (1$_{Ex}$=490 nm and 1$_{Em}$=520 nm) monitored using a FLIPR (Fluorometric Imaging Plate Reader, Molecular Devices, Sunnyvale, U.S.A.).

b) Human monocytes

Human monocytes were isolated from EDTA anticoagulated peripheral blood as previously described (Cunoosamy & Holbrook, J. Leukocyte Biology, 1998, S2, 13). Cells were resuspended ($5\times10^6$ ml$^{-1}$) in LKS and loaded with 5 μM FLUO-3/AM+Pluronic F127 2.2 μl/ml (Molecular Probes) for one hour at room temperature. After loading, cells were centrifuged at 200 g for 5 min and resuspended in LKS at $0.5\times10^6$ ml$^{-1}$. The cells were then transferred to 96 well FLIPr plates (Costar). To each well 100 μl of cells were added at a concentration of $0.5\times10^6$ ml$^{-1}$. The plates were centrifuged (200 g; 5 mins; room temperature) to allow the cells to adhere. After centrifugation the cells were washed twice with LKS (200 μl; room temperature).

A compound of the Examples was pre-dissolved in dimethylsulphoxide and added to a final concentration of 0.1% (v/v) dimethylsulphoxide. Assays were initiated by the addition of an $A_{50}$ concentration of MIP-1α and the transient increase in fluo-3 fluorescence ($1_{Ex}$=490 nm and $1_{Em}$=520 nm) monitored using a FLIPR (Fluorometric Imaging Plate Reader, Molecular Devices, Sunnyvale, U.S.A.).

The compounds of the Examples were found to be antagonists of the eotaxin mediated $[Ca^{2+}]_i$ in human eosinophils and/or antagonists of the MIP-1α mediated $[Ca^{2+}]_i$ in human monocytes.

Human eosinophil chemotaxis

Human eosinophils were isolated from EDTA anticoagulated peripheral blood as previously described (Hansel et al., J. Immunol. Methods, 1991, 145, 105–110). The cells were resuspended at $10\times10^6$ ml$^{-1}$ in RPMI containing 200 IU/ml penicillin, 200 μg/ml streptomycin sulphate and supplemented with 10% HIFCS, at room temperature.

Eosinophils (700 μl) were pre-incubated for 15 mins at 37° C. with 7 μl of either vehicle or compound (100× required final concentration in 10% dimethylsulphoxide). The chemotaxis plate (Chemo Tx, 3 μm pore, Neuroprobe) was loaded by adding 28 μl of a concentration of eotaxin (0.1 to 100 nM) containing a concentration of a compound according to the Examples or solvent to the lower wells of the chemotaxis plate. The filter was then placed over the wells and 25 μl of eosinophil suspension were added to the top of the filter. The plate was incubated for 1 hr at 37° C. in a humidified incubator with a 95% air/5% $CO_2$ atmosphere to allow chemotaxis.

The medium, containing cells that had not migrated, was carefully aspirated from above the filter and discarded. The filter was washed once with phosphate buffered saline (PBS) containing 5 mM EDTA to remove any adherent cells. Cells that had migrated through the filter were pelleted by centrifugation (300×g for 5 mins at room temperature) and the filter removed and the supernatant transferred to each well of a 96-well plate (Costar). The pelleted cells were lysed by the addition of 28 μl of PBS containing 0.5% Triton ×100 followed by two cycles of freeze/thawing. The cell lysate was then added to the supernatant. The number of eosinophils migrating was quantified according to the method of Strath et al., J. Immunol. Methods, 1985, 83, 209 by measuring eosinophil peroxidase activity in the supernatant.

Certain compounds of the Examples were found to be antagonists of the eotaxin mediated human eosinophil chemotaxis.

What is claimed is:

1. A compound of formula (I), or a pharmaceutically acceptable salt thereof, or solvate thereof, or a solvate of a salt thereof:

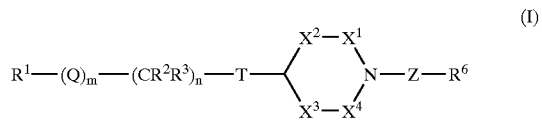

wherein

Z is $CR^4R^5$, wherein $R^4$ and $R^5$ are $CH_2$;

$R^1$ represents a 3- to 14-membered saturated or unsaturated ring system which comprises up to two ring carbon atoms that form carbonyl groups and which further comprises up to 4 ring heteroatoms independently selected from nitrogen, oxygen and sulphur, wherein the ring system is optionally substituted by one or more substituents independently selected from: halogen, cyano, nitro, oxo, hydroxyl, $C_1$-$C_8$ alkyl, $C_1$-$C_6$ hydroxyalkyl, $C_1$-$C_6$ haloalkyl, $C_{1-6}$ alkoxy($C_1$-$C_6$ alkyl), $C_3$-$C_7$ cycloalkyl($C_1$-$C_6$ alkyl), $C_1$-$C_6$ alkylthio ($C_1$-$C_6$ alkyl), $C_1$-$C_6$ alkylcarbonyloxy($C_1$-$C_6$ alkyl), $C_1$-$C_6$ alkylS(O)$_2$($C_1$-$C_6$ alkyl), aryl($C_1$-$C_6$ alkyl), heterocyclyl($C_1$-$C_6$ alkyl), arylS(O)$_2$($C_1$-$C_6$ alkyl), heterocyclylS(O)$_2$($C_1$-$C_6$ alkyl), aryl($C_1$-$C_6$ alkyl)S(O)$_2$, heterocyclyl($C_1$-$C_6$ alkyl(S(O)$_2$, $C_2$-$C_6$ alkenyl, $C_1$-$C_6$ alkoxy, carboxy-substituted $C_1$-$C_6$ alkoxy, $C_1$-$C_6$ haloalkoxy, $C_1$-$C_6$ hydroxyalkoxy, $C_1$-$C_6$ alkylcarboxy-substituted $C_1$-$C_6$ alkoxy, aryloxy, heterocyclyloxy, $C_1$-$C_6$ alkylthio, $C_3$-$C_7$ cycloalkyl ($C_1$-$C_6$ alkylthio), $C_3$-$C_6$ alkynylthio, $C_1$-$C_6$ alkylcarbonylamino, $C_1$-$C_6$ haloalkylcarbonylamino, $SO_3H$, —$NR^7R^8$, —$C(O)NR^{23}R^{24}$, $S(O)_2NR^{18}R^{19}$, $S(O)_2R^{20}$, $R^{25}C(O)$, carboxyl, $C_1$-$C_6$ alkoxycarbonyl, aryl and heterocyclyl; wherein the foregoing aryl and heterocyclyl moieties are optionally substituted by one or more of halogen, oxo, hydroxy, nitro, cyano, $C_1$-$C_6$ alkyl, $C_1$-$C_6$ haloalkyl, phenyl($C_1$-$C_6$ alkyl), $C_1$-$C_6$ alkoxy, $C_1$-$C_6$ haloalkoxy, $S(O)_2$($C_1$-$C_6$ alkyl), $C(O)NH_2$, carboxy or $C_1$-$C_6$ alkoxycarbonyl;

m is 0;

n is 2;

each $R^2$ and $R^3$ independently represents a hydrogen atom or a $C_1$-$C_4$ alkyl group, or $(CR^2R^3)_n$ represents $C_3$-$C_7$ cycloalkyl optionally substituted by $C_1$-$C_4$ alkyl;

T represents a group $C(O)NR^{10}$, wherin $R^{10}$ is H;

$X^1$, $X^2$, $X^3$ and $X^4$ are, independently, $CH_2$;

$R^4$ and $R^5$ each independently represent a hydrogen atom or a $C_1$-$C_4$ alkyl group;

$R^6$ is phenyl, optionally substituted by one or more of: halogen, cyano, nitro, oxo, hydroxyl, $C_1$-$C_8$ alkyl, $C_1$-$C_6$ hydroxyalkyl, $C_1$-$C_6$ haloalkyl, $C_{1-6}$ alkoxy($C_1$-$C_6$ alkyl), $C_3$-$C_7$ cycloalkyl($C_1$-$C_6$ alkyl), $C_1$-$C_6$ alkylthio($C_1$-$C_6$ alkyl), $C_1$-$C_6$ alkylcarbonyloxy($C_1$-$C_6$ alkyl), $C_1$-$C_6$ alkylS(O)$_2$($C_1$-$C_6$ alkyl), aryl($C_1$-$C_6$ alkyl), heterocyclyl($C_1$-$C_6$ alkyl), arylS(O)$_2$($C_1$-$C_6$ alkyl), heterocyclylS(O)$_2$($C_1$-$C_6$ alkyl), aryl($C_1$-$C_6$ alkyl)S(O)$_2$, heterocyclyl($C_1$-$C_6$ alkyl)S(O)$_2$, $C_2$-$C_6$ alkenyl, $C_1$-$C_6$ alkoxy, carboxy-substituted $C_1$-$C_6$ alkoxy, $C_1$-$C_6$ haloalkoxy, $C_1$-$C_6$ hydroxyalkoxy, $C_1$-$C_6$ alkylcarboxy-substituted $C_1$-$C_6$ alkoxy, aryloxy, heterocyclyloxy, $C_1$-$C_6$ alkylthio, $C_3$-$C_7$ cycloalkyl ($C_1$-$C_6$ alkylthio), $C_3$-$C_6$ alkynylthio, $C_1$-$C_6$ alkylcarbonylamino, $C_1$-$C_6$ haloalkylcarbonylamino, $SO_3H$, $-NR^{16}R^{17}$, $-C(O)NR^{21}R^{22}$, $S(O)_2NR^{13}R^{14}$, $S(O)_2R^{15}$, $R^{26}C(O)$, carboxyl, $C_1$-$C_6$ alkoxycarbonyl, aryl and heterocyclyl; wherein the foregoing aryl and heterocyclyl moieties are optionally substituted by one or more of halogen, nitro, cyano, $C_1$-$C_6$ alkyl, $C_1$-$C_6$ haloalkyl, phenyl($C_1$-$C_6$ alkyl), $C_1$-$C_6$ alkoxy, $C_1$-$C_6$ haloalkoxy, $S(O)_2(C_1$-$C_6$ alkyl), $C(O)NH_2$, carboxy or $C_1$-$C_6$ alkoxycarbonyl; $R^7$, $R^8$, $R^9$, $R^{10}$, $R^{11}$, $R^{13}$, $R^{14}$, $R^{16}$, $R^{17}$, $R^{18}$, $R^{19}$, $R^{21}$, $R^{22}$, $R^{23}$ and $R^{24}$ are, independently hydrogen, $C_1$-$C_6$ alkyl, $C_1$-$C_6$ haloalkyl, $C_1$-$C_6$ hydroxyalkyl, $C_3$-$C_7$ cycloalkyl, $C_3$-$C_7$ cycloalkyl($C_1$-$C_4$ alkyl) or phenyl($C_1$-$C_6$ alkyl); and, $R^{15}$ and $R^{20}$ are, independently, $C_1$-$C_6$ alkyl, $C_1$-$C_6$ hydroxyalkyl, $C_3$-$C_6$ cycloalkyl, $C_3$-$C_7$ cycloalkyl($C_1$-$C_4$ alkyl) or $C_1$-$C_6$ alkyl optionally substituted by phenyl;

$R^{25}$ and $R^{26}$ are, independently, $C_1$-$C_6$ alkyl or phenyl (optionally substituted by one or more of halogen, nitro, cyano, $C_1$-$C_6$ alkyl, $C_1$-$C_6$ haloalkyl, phenyl($C_1$-$C_6$ alkyl), $C_1$-$C_6$ alkoxy, $C_1$-$C_6$ haloalkoxy, $S(O)_2(C_1$-$C_6$ alkyl), $C(O)NH_2$, carboxy or $C_1$-$C_6$ alkoxycarbonyl).

2. A compound as defined in any one of Examples 1 to 416.

3. A process for the preparation of a compound of formula (I) as defined in claim 1 which comprises:

(a) when T is $C(O)NR^{10}$, reacting a compound of general formula

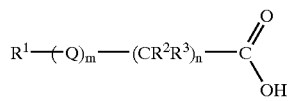

(VI)

wherein $R^1$, $R^2$, $R^3$, Q, m and n are as defined in formula (I), with a compound of formula (III)

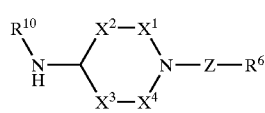

(III)

wherein $X^1$, $X^2$, $X^3$, $X^4$, Z, $R^6$ and $R^{10}$ are as defined in formula (I), or a salt thereof as defined in (a) above; or (b) when at least one of $R^4$ and $R^5$ represents a hydrogen atom, reacting a compound of general formula

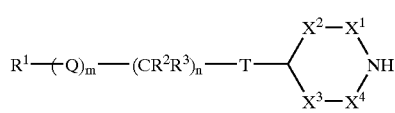

(IX)

or a salt thereof, wherein $R^1$, $R^2$, $R^3$, Q, m, n, $X^1$, $X^2$, $X^3$, $X^4$ and T are as defined in formula (I), with a compound of general formula (X), $R^6$—$C(O)$—$R^{20}$, wherein $R^{20}$ represents a hydrogen atom or a $C_1$-$C_4$ alkyl group and $R^6$ is as defined in formula (I), in the presence of a reducing agent; or (c) reacting a compound of formula (IX) as defined in (b) above, with a compound of general formula

(XI)

wherein $L^2$ represents a leaving group (e.g. a halogen atom) and Z and $R^6$ are as defined in formula (I);

and optionally after (a), (b), or (c) forming a pharmaceutically acceptable salt or solvate of the compound of formula (I) obtained.

4. A pharmaceutical composition comprising a compound of formula (I), or a pharmaceutically acceptable salt or solvate thereof, as in claim 1 in association with a pharmaceutically acceptable adjuvant, diluent or carrier.

5. A process for the preparation of a pharmaceutical composition as claimed in claim 4 which comprises mixing a compound of formula (I), or a pharmaceutically acceptable salt or solvate thereof, as in claim 1 with a pharmaceutically acceptable adjuvant, diluent or carrier.

6. A method of treating asthma in a patient suffering from, or at risk of, said disease, which comprises administering to the patient a therapeutically effective amount of a compound of formula (I), or a pharmaceutically acceptable salt thereof, or solvate thereof, or a solvate of a salt thereof,

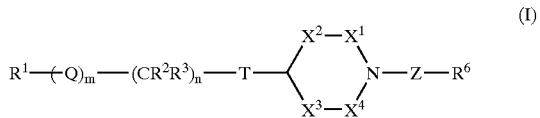

(I)

wherein

Z is $CR^4R^5$, wherein $R^4$ and $R^5$ are $CH_2$;

$R^1$ represents a 3- to 14-membered saturated or unsaturated ring system which comprises up to two ring carbon atoms that form carbonyl groups and which further comprises up to 4 ring heteroatoms independently selected from nitrogen, oxygen and sulphur, wherein the ring system is optionally substituted by one or more substituents independently selected from: halogen, cyano, nitro, oxo, hydroxyl, $C_1$-$C_8$ alkyl, $C_1$-$C_6$ hydroxyalkyl, $C_1$-$C_6$ haloalkyl, $C_{1-6}$ alkoxy($C_2$-$C_6$ alkyl), $C_3$-$C_7$ cycloalkyl($C_1$-$C_6$ alkyl), $C_1$-$C_6$ alkylthio ($C_1$-$C_6$ alkyl), $C_1$-$C_6$ alkylcarbonyloxy($C_1$-$C_6$ alkyl), $C_1$-$C_6$ alkylS(O)$_2$($C_1$-$C_6$ alkyl), aryl($C_1$-$C_6$ alkyl), heterocyclyl($C_1$-$C_6$ alkyl), arylS(O)$_2$($C_1$-$C_6$ alkyl), heterocyclylS(O)$_2$($C_1$-$C_6$ alkyl), aryl($C_1$-$C_6$ alkyl) S(O)$_2$, heterocyclyl($C_1$-$C_6$ alkyl)S(O)$_2$, $C_2$-$C_6$ alkenyl, $C_1$-$C_6$ alkoxy, carboxy-substituted $C_1$-$C_6$ alkoxy, $C_1$-$C_6$ haloalkoxy, $C_1$-$C_6$ hydroxyalkoxy, $C_1$-$C_6$ alkylcarboxy-substituted $C_1$-$C_6$ alkoxy, aryloxy, heterocyclyloxy, $C_1$-$C_6$ alkylthio, $C_3$-$C_7$ cycloalkyl ($C_1$-$C_6$ alkylthio), $C_3$-$C_6$ alkynylthio, $C_1$-$C_6$ alkylcarbonylamino, $C_1$-$C_6$ haloalkylcarbonylamino, $SO_3H$, $-NR^7R^8$, $-C(O)NR^{23}R^{24}$, $S(O)_2NR^{18}R^{19}$, $S(O)_2R^{20}$, $R^{25}C(O)$, carboxyl, $C_1$-$C_6$ alkoxycrbonyl, aryl and heterocyclyl; wherein the foregoing aryl and heterocyclyl moieties are optionally substituted by one or more of halogen, oxo, hydroxy, nitro, cyano, $C_1$-$C_6$ alkyl, $C_1$-$C_6$ haloalkyl, phenyl($C_1$-$C_6$ alkyl), $C_1$-$C_6$ alkoxy, $C_1$-$C_6$ haloalkoxy, $S(O)_2(C_1$-$C_6$ alkyl), $C(O)$ $NH_2$, carboxy or $C_1$-$C_6$ alkoxycarbonyl;

m is 0;

n is 2;

each $R^2$ and $R^3$ independently represents a hydrogen atom or a $C_1$-$C_4$ alkyl group, or $(CR^2R^3)_n$ represents $C_3$-$C_7$ cycloalkyl optionally substituted by $C_1$-$C_4$ alkyl;

T represents a group $C(O)NR^{10}$;

$X^1$, $X^2$, $X^3$ and $X^4$ are, independently, $CH_2$;

$R^4$ and $R^5$ each independently represent a hydrogen atom or a $C_1$-$C_4$ alkyl group;

$R^6$ is phenyl optionally substituted by one or more of: halogen, cyano, nitro, oxo, hydroxyl, $C_1$-$C_8$ alkyl, $C_1$-$C_6$ hydroxyalkyl, $C_1$-$C_6$ haloalkyl, $C_{1-6}$ alkoxy($C_1$-$C_6$ alkyl), $C_3$-$C_7$ cycloalkyl($C_1$-$C_6$ alkyl), $C_1$-$C_6$ alkylthio($C_3$-$C_6$ alkyl), $C_1$-$C_6$ alkylcarbonyloxy($C_1$-$C_6$ alkyl), $C_1$-$C_6$ alkylS(O)$_2$($C_1$-$C_6$ alkyl), aryl($C_1$-$C_6$ alkyl), heterocyclyl($C_1$-$C_6$ alkyl), arylS(O)$_2$($C_1$-$C_6$ alkyl), heterocyclylS(O)$_2$($C_1$-$C_6$ alkyl), aryl($C_1$-$C_6$ alkyl)S(O)$_2$, heterocyclyl($C_1$-$C_6$ alkyl)S(O)$_2$, $C_2$-$C_6$ alkenyl, $C_1$-$C_6$ alkoxy, carboxy-substituted $C_1$-$C_6$ alkoxy, $C_1$-$C_6$ haloalkoxy, $C_1$-$C_6$ hydroxyalkoxy, $C_1$-$C_6$ alkylcarboxy-substituted $C_1$-$C_6$ alkoxy, aryloxy, heterocyclyloxy, $C_1$-$C_6$ alkylthio, $C_3$-$C_7$ cycloalkyl ($C_1$-$C_6$ alkylthio), $C_3$-$C_6$ alkynylthio, $C_1$-$C_6$ alkylcarbonylamino, $C_1$-$C_6$ haloalkylcarbonylamino, $SO_3H$, —$NR^{16}R^{17}$, —$C(O)NR^{21}R^{22}$, $S(O)_2NR^{13}R^{14}$, $S(O)_2R^{15}$, $R^{26}C(O)$, carboxyl, $C_1$-$C_6$ alkoxycarbonyl, aryl and heterocyclyl; wherein the foregoing aryl and heterocyclyl moieties are optionally substituted by one or more of halogen, nitro, cyano, $C_1$-$C_6$ alkyl, $C_1$-$C_6$ haloalkyl, phenyl($C_1$-$C_6$ alkyl), $C_1$-$C_6$ alkoxy, $C_1$-$C_6$ haloalkoxy, $S(O)_2$($C_1$-$C_6$ alkyl), $C(O)NH_2$, carboxy or $C_1$-$C_6$ alkoxycarbonyl;

$R^7$, $R^8$, $R^9$, $R^{10}$, $R^{13}$, $R^{14}$, $R^{16}$, $R^{17}$, $R^{18}$, $R^{19}$, $R^{21}$, $R^{22}$, $R^{23}$ and $R^{24}$ are, independently hydrogen, $C_1$-$C_6$ alkyl, $C_1$-$C_6$ haloalkyl, $C_1$-$C_6$ hydroxyalkyl, $C_3$-$C_7$ cycloalkyl, $C_3$-$C_7$ cycloalkyl($C_1$-$C_4$ alkyl) or phenyl ($C_1$-$C_6$ alkyl); and, $R^{15}$ $R^{20}$ are, independently, $C_1$-$C_6$ alkyl, $C_1$-$C_6$ hydroxyalkyl, $C_3$-$C_6$ cycloalkyl, $C_3$-$C_7$ cycloalkyl($C_1$-$C_4$ alkyl) or $C_1$-$C_6$ alkyl optionally substituted by phenyl;

$R^{25}$ and $R^{26}$ are, independently, $C_1$-$C_6$ alkyl or phenyl (optionally substituted by one or more of halogen, nitro, cyano, $C_1$-$C_6$ alkyl, $C_1$-$C_6$ haloalkyl, phenyl($C_1$-$C_6$ alkyl), $C_1$-$C_6$ alkoxy, $C_1$-$C_6$ haloalkoxy, $S(O)_2$($C_1$-$C_6$ alkyl), $C(O)NH_2$, carboxy or $C_1$-$C_6$ alkoxycarbonyl).

\* \* \* \* \*

UNITED STATES PATENT AND TRADEMARK OFFICE
CERTIFICATE OF CORRECTION

PATENT NO. : 6,903,085 B1
DATED : June 7, 2005
INVENTOR(S) : Stephen Thom et al.

It is certified that error appears in the above-identified patent and that said Letters Patent is hereby corrected as shown below:

Title page,
Item [75], Inventors, replace "Nicholas Kindor" with -- Nicholas Kindon --.
Item [56], References Cited, OTHER PUBLICATIONS,
"J. Hesselgesser" reference, replace "Funtional" with -- Functional --.
"Friebe" reference, replace "dervatives" with -- derivatives --.
"Navas III..." reference, replace "Haupten" with -- Hapten for -- and replace "Antopsychotic" with -- Antipsychotic --.
"Rubini" reference, replace "Ony" with -- Oxy --.

Column 96,
Line 26, replace "$(C_1-C_6alkyl(S(O)_2$" with -- $(C_1-C_6alkyl)S(O)_2$ --.

Column 98,
Line 61, replace "alkoxycrbonyl" with -- alkoxycarbonyl --.

Column 100,
Line 8, insert -- $R^{11}$, -- between "$R^{10}$," and "$R^{13}$".

Signed and Sealed this

Sixth Day of December, 2005

JON W. DUDAS
*Director of the United States Patent and Trademark Office*